US008729258B2

(12) United States Patent
Raymond et al.

(10) Patent No.: US 8,729,258 B2
(45) Date of Patent: **\*May 20, 2014**

(54) LUMINESCENT MACROCYCLIC LANTHANIDE COMPLEXES

(75) Inventors: Kenneth N. Raymond, Berkeley, CA (US); Todd M. Corneillie, Campbell, CA (US); Jide Xu, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/460,120

(22) Filed: Apr. 30, 2012

(65) Prior Publication Data

US 2012/0329174 A1    Dec. 27, 2012

Related U.S. Application Data

(63) Continuation of application No. 11/839,509, filed on Aug. 15, 2007, now Pat. No. 8,173,800.

(60) Provisional application No. 60/822,482, filed on Aug. 15, 2006.

(51) Int. Cl.
| | | |
|---|---|---|
| A01N 55/02 | (2006.01) | |
| A61K 31/40 | (2006.01) | |
| C07B 47/00 | (2006.01) | |
| C07D 487/22 | (2006.01) | |

(52) U.S. Cl.
USPC ........ 540/145; 540/460; 530/391.3; 564/152; 436/546; 435/24

(58) Field of Classification Search
USPC ................ 540/145, 460; 530/391.3; 564/152; 436/546; 435/24
See application file for complete search history.

(56) References Cited

U.S. PATENT DOCUMENTS

| | | | |
|---|---|---|---|
| 2,977,332 | A | 3/1961 | Zumstein |
| 4,748,184 | A | 5/1988 | Stout et al. |
| 4,855,225 | A | 8/1989 | Fung et al. |
| 5,047,519 | A | 9/1991 | Hobbs, Jr. et al. |
| 5,049,280 | A | 9/1991 | Raymond et al. |
| 5,252,462 | A | 10/1993 | Drevin et al. |
| 5,470,896 | A | 11/1995 | Wegmann et al. |
| 5,820,849 | A | 10/1998 | Schmitt-Willich et al. |
| 5,989,823 | A | 11/1999 | Jayasena et al. |
| 6,406,297 | B1 | 6/2002 | Raymond et al. |
| 6,515,113 | B2 | 2/2003 | Raymond et al. |
| 6,864,103 | B2 | 3/2005 | Raymond et al. |
| 7,018,850 | B2 | 3/2006 | Raymond et al. |
| 7,442,558 | B2 | 10/2008 | Raymond et al. |
| 8,173,800 | B2 * | 5/2012 | Raymond et al. ............ 540/145 |
| 2002/0128451 | A1 | 9/2002 | Raymond et al. |
| 2002/0188111 | A1 | 12/2002 | Raymond et al. |
| 2003/0199688 | A1 | 10/2003 | Kriesel et al. |
| 2005/0058604 | A1 | 3/2005 | Raymond et al. |
| 2007/0134160 | A1 | 6/2007 | Leif et al. |
| 2008/0213780 | A1 | 9/2008 | Butlin et al. |
| 2008/0213917 | A1 | 9/2008 | Raymond et al. |
| 2009/0023928 | A1 | 1/2009 | Raymond et al. |
| 2009/0036537 | A1 | 2/2009 | Raymond et al. |
| 2010/0151591 | A1 | 6/2010 | Butlin et al. |
| 2010/0167289 | A1 | 7/2010 | Butlin et al. |

FOREIGN PATENT DOCUMENTS

| | | |
|---|---|---|
| CA | 2099542 | 7/1993 |
| EP | 0578067 | 6/1993 |
| WO | WO/89/11475 | 11/1989 |
| WO | WO 91/12530 | 8/1991 |
| WO | WO 92/11039 | 7/1992 |
| WO | WO 97/45539 | 4/1997 |
| WO | WO 00/48991 | 8/2000 |
| WO | WO 2005/030711 | 4/2005 |
| WO | WO 2008/063721 | 5/2008 |
| WO | WO 2008/092120 | 7/2008 |
| WO | WO 2010/051544 | 5/2010 |

OTHER PUBLICATIONS

Arnaud et al., "Synthesis of macrocyclic tetralactams from L-tataric acid and beta-hydroxyglutaric acid", *Tetrahedron*, 53(40): 13757-13768, XP002537292 (1997).

Blomberg, et al., "Terbium and rhodamine as labels in a homogeneous time resolved fluorometric energy transfer assay of the β subunit of human chorionic gonadotropin in serum", *Clinical Cehmistry*, 45(6):855-861 (1999).

Brooker, S. et al., Chemical Abstract 2002: 593344 (2002).

Bünzli, et al., "Towards materials with planned properties : dinuclear f-f helicates and d-f nonconvalent podates based on benzimidazole-pyridine binding units", *Journal of Alloys and Compounds*, 249:14-24 (1997).

Cardullo, R. et al., "Detection of nucleic acid hybridization by nonradiative fluorescence resonance energy transfer", *Proc. Natl. Acad. Sci. USA* 85:8790-8794 (1988).

Chen, et al., "Lifetime- and color-tailored fluorophores in the micro-to-millisecond time regime", *J. Am. Chem. Soc.*, 122(4):657-660 (2000).

Cohen et al., "A Novel Salicylate-Based Macrobicycle with a 'Split Personality'", *Inorg. Chem.*, 38(20):4522-4529, XP002537288 (1999).

Dahlén "Detection of Biotinylated DNA Probes by Using Eu-Labeled Streptavidin and Time-Resolved Fluorometry" *Anal. Biochem.*, 164:78-83 (1987).

De Sá, et al., "Spectroscopic properties and design of highly luminescent lanthanide coordination complexes", *Coordination Chemistry Reviews*, 196:165-195 (2000).

Dexter, D.L., "A Theory of Sensitized Luminescence in Solids", *Journal of Chemical Physics* 21: 836-850 (1953).

(Continued)

*Primary Examiner* — Paul V. Ward
(74) *Attorney, Agent, or Firm* — Morgan, Lewis & Bockius LLP; Jeffry S. Mann; Todd Esker

(57) ABSTRACT

The present invention provides a novel class of macrocyclic compounds as well as complexes formed between a metal (e.g., lanthanide) ion and the compounds of the invention. Preferred complexes exhibit high stability as well as high quantum yields of lanthanide ion luminescence in aqueous media without the need for secondary activating agents. Preferred compounds incorporate hydroxy-isophthalamide moieties within their macrocyclic structure and are characterized by surprisingly low, non-specific binding to a variety of polypeptides such as antibodies and proteins as well as high kinetic stability. These characteristics distinguish them from known, open-structured ligands.

17 Claims, 6 Drawing Sheets

(56) References Cited

OTHER PUBLICATIONS

Dickins, et al., "Synthesis, time-resolved luminescence, NMR spectroscopy, circular dichroism and circularly polarised luminescence studies f enantiopure macrocyclic lanthanide tetraamide complexes", *Chem. Eur. J.*, 5(3):1095-1105 (1999).

Dickson, et al., "Time-resolved detection of lanthanide luminescence of ultrasensitive bioanalytical assays", *Journal of Photochemistry and Photobiology, B: Biology*, 27:3-19 (1995).

Galaup, et al., "Mono(di)nuclear eropium(III) complexes of macrobi(tri)cyclic cryptands derived from diazatetralactams as luminophores in aqueous solutions", *Helvetica Chimica Acta*, 82:543-560 (1999).

Gong, B., "Crescent oligoamides: From acyclic "Macrocycles" to folding nanotubes", *Chem. Eur. J.*, 7(20): 4336-4342, XP002537290 (2001).

Heid, C. et al., "Real time quantitative PCR", *Genome Res.* 6:986-994 (1996).

Hemmilä, et al., "Development of luminescent lanthanide chelate labels for diagnostic assays", *Journal of Alloys and Compounds*, 249:158-162 (1997).

Higuchi, R. et al., "Simultaneous Amplification and Detection of Specific DNA Sequences", *Bio/Technology* 10:413-417 (1992).

Hochstrasser, R. et al., "Distance distribution in a dye-linked oligonucleotide dtermined by time-resolved fluorescence energy transfer", *Biophysical Chemistry* 45:133-141 (1992).

Holland, P. et al., "Detection of specific polymerase chain reaction product by utilizing the 5'-→ 3' exonuclease activity of *Thermus aquaticus* DNA polymerase", *Proc. Nat. Acad. Sci. USA*, 88:7276-7280 (1991).

Johansson et al., "Time Gating Improves Sensitivity in Energy Transfer Assays with Terbium Chelate/Dark Quencher Oligonucleotide Probes" *J. Am. Chem. Soc.*, 126(50): 16451-16455 (2004).

Knight, C.G., "Fluorimetric Assays of Proteolytic Enzymes", *Methods in Enzymology* 248: 18-34 (1995).

Kostrikis, L. et al., "Spectral Genotyping of Human Alleles", *Science* 279:1228-1229 (1998).

Lee, L. et al., "Allelic discrimination by nick-translation PCR with fluorogenic probes", *Nucleic Acids Res.* 21:3761-3766 (1993).

Lee, L. G. et al., "Seven-Color, Homogeneous Detection of Six PCR Products" *BioTechniques* 27:342-349 (1999).

Li et al., "Shape-persistant aromatic amide oligomers: New tools for supramolecular chemistry", *Chem. Asian J.*, 1:766-778, XP002537289 (2006).

Momany et al., "Crystal structure of dimeric HIV-1 capsid protein", *Nature Structural Biology*, vol. 3, No. 9, pp. 763-770 (1996).

Nazarenko, I.A. et al., "A closed tube format for amplification and detection of DNA based on energy transfer", *Nucleic Acids Res.* 25:2516-2521 (1997).

Okawa et al., "Binuclear metal complexes. V. Template synthesis of a binuclear copper(II) complex of a macrocycle containing amino groups", *Chem. Lett.*, 1027-1030. (1972).

Petoud et al., "Stable Lanthanide Luminescence Agents Highly Emissive in Aqueous Solution: Multidentate 2-Hydroxyisophthalamide Complexes of $Sm^{3+}$, $Eu^{3+}$, $Tb^{3+}$, $Dy^{3+}$" *J. Am. Chem. Soc.*, 125: 13354-13325 (2003).

Sabbatini, et al., "Luminescent lanthanide complexes as photochemical supramolecular devices", *Coordination Chemistry Reviews*, 123:201-228 (1993).

Saha, et al., "Time-resolved fluorescence of a new europium chelate complex: Demonstration of highly sensitive detection of protein and DNA samples", *J. Am. Chem. Soc.*, 115:11032-11032 (1993).

Selvin, P., "Fluorescence Resonance Energy Transfer", *Methods in Enzymology* 246:300-334 (1995).

Sequoia, E., "Complexes of Lanthanide Perchlorates", *Inorganica Chimica Acta*, 37:1 L-449-L451 (1979).

Soini, et al., "Time-resolved fluorescence of lanthanide probes and applications in biotechnology", *CRC Critical Reviews in Analytical Chemistry*, 18(2):105-154 (1987).

Steemers, et al., "Water-soluble neutral calix[4]arene-lathanide complexes: Synthesis and luminescence properties", *J. Org. Chem.*, 62:4229-4235 (1997).

Steinberg, I., "Long-Range Nonradiative Transfer of Electronic Excitation Energy in Proteins and Polypeptides", *Ann. Rev. Biochem.* 40:83-114 (1971).

Stenroos, et al., "Homogeneous time-resolved IL-2IL-Rα assay using fluorescence resonance energy transfere", *Cytokine* 10(7):495-499 (Jul. 1998).

Stryer, L., "Fluorescence Energy Transfer as a Spectroscopic Ruler", Ann. Rev. Biochem. 47:819-846 (1978).

Syvänen et al., "Time-resolved fluorometry: a sensitive method to quantify DNA-hybrids" *Nucleic Acids Research*, 14:1017-1028 (1986).

Tyagi, S. et al., "Molecular Beacons: Probes that Fluoresce upon Hybridization", *Nature Biotechnology* 14: 303-308 (1996).

Tyagi, S. et al., "Multicolor molecular beacons for allele discrimination", *Nature Biotechnology* 16:49-53 (1998).

Veiopoulou, et al., "Comparative study of fluorescent ternary terbium complexes. Application in enzyme amplified fluorimetric immunoassay for a-fetoprotein", *Analytica Chimica Acta*, 335:177-184 1996).

Vicentini, et al., "Luminescence and structure of europium compounds", *Coordination Chemistry Reviews*, 196:353-382 (2000).

Voss, H. et al., "Direct genomic fluorescent on-line sequencing and analysis using in vivo amplification of DNA", *Nucleic Acids Research* 17:2517 (1989).

Wang, G. et al., "Design and Synthesis of New Fluorogenic HIV Protease Substrates Based on Resonance Energy Transfer", *Tetrahedron Letters* 31: 6493-6496 (1990).

Wang, Y. et al., "Rapid Sizing of Short Tandem Repeat Alleles Using Capillary Array Electrophoresis and Energy-Transfer Fluorescent Primers", *Anal. Chem.* 67:1197-1203 (1995).

Whitcombe, D. et al., "Detection of PCR products using self-probing amplicons and fluorescence", *Nature Biotechnology* 17:804-807 (1999).

\* cited by examiner

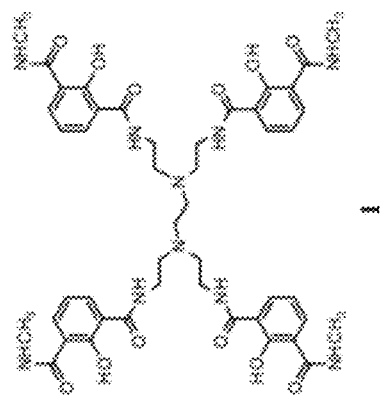
FIG. 1
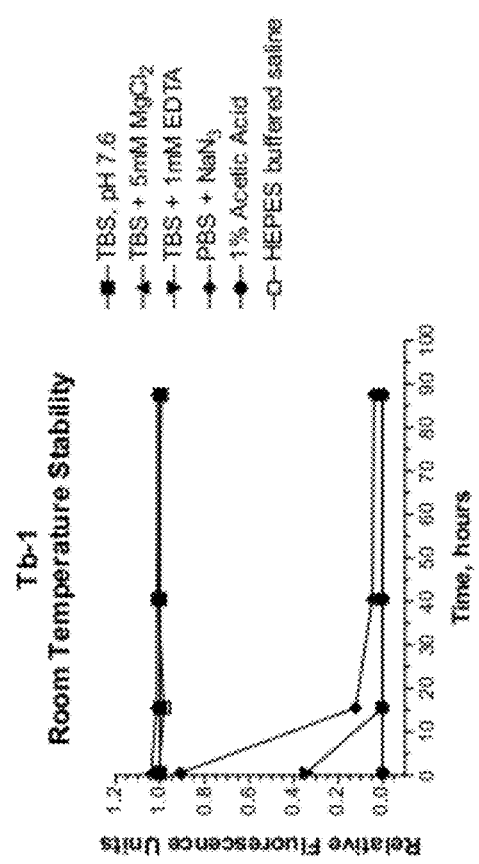

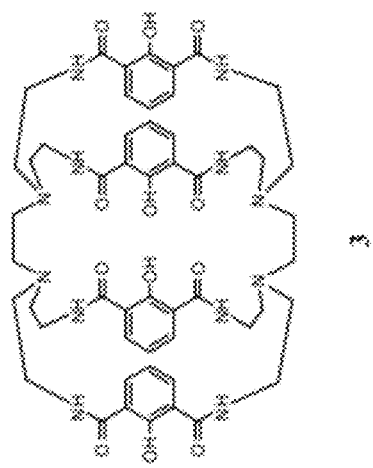
FIG. 2
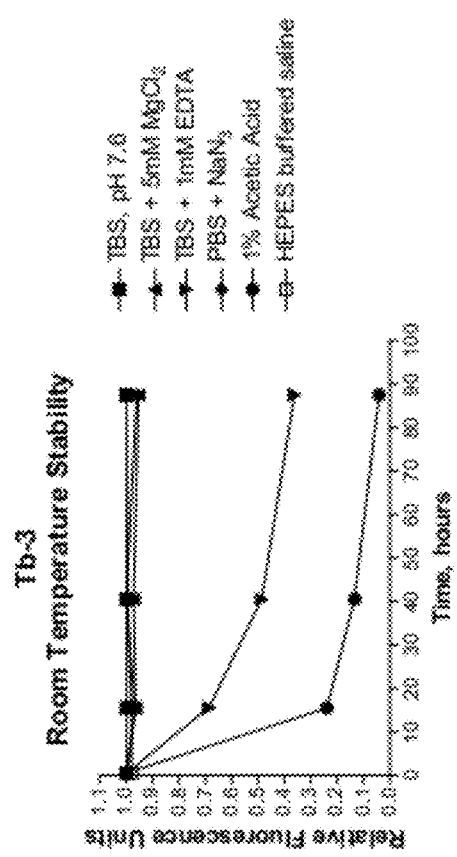

LUMINESCENT MACROCYCLIC LANTHANIDE COMPLEXES

CROSS-REFERENCE TO RELATED APPLICATIONS

This application is a Continuation of U.S. patent application Ser. No. 11/839,509 filed on Aug. 15, 2007, now U.S. Pat. No. 8,173,800 which claims the benefit under 35 USC 119(e) to U.S. Provisional Application No. 60/822,482 filed on Aug. 15, 2006, both of which are incorporated herein by reference in their entirety for all purposes.

STATEMENT REGARDING FEDERALLY SPONSORED RESEARCH OR DEVELOPMENT

This invention was made with Government support under Grant No. DE-AC03-76SF00098 awarded by the U.S. Department of Energy and Grant Nos. AI063531 and EB004239 awarded by the National Institutes of Health. The Government has certain rights in the invention.

FIELD OF THE INVENTION

This invention relates to macrocyclic ligands and lanthanide complexes thereof, useful as luminescent markers, as well as methods utilizing the ligands and complexes of the invention.

BACKGROUND OF THE INVENTION

There is a continuous and expanding need for rapid, highly specific methods of detecting and quantifying chemical, biochemical and biological substances as analytes in research and diagnostic mixtures. Of particular value are methods for measuring small quantities of nucleic acids, peptides, pharmaceuticals, metabolites, microorganisms and other materials of diagnostic value. Examples of such materials include small molecular bioactive materials (e.g., narcotics and poisons, drugs administered for therapeutic purposes, hormones), pathogenic microorganisms and viruses, antibodies, and enzymes and nucleic acids, particularly those implicated in disease states.

The presence of a particular analyte can often be determined by binding methods that exploit the high degree of specificity which characterize many biochemical and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which has been attached to one or more of the interacting materials. The specific labeling method chosen often dictates the usefulness and versatility of a particular system for detecting an analyte of interest. Preferred labels are inexpensive, safe, and capable of being attached efficiently to a wide variety of chemical, biochemical, and biological materials without significantly altering the important binding characteristics of those materials. The label should give a highly characteristic signal, and should be rarely, and preferably never, found in nature. The label should be stable and detectable in aqueous systems over periods of time ranging up to months. Detection of the label is preferably rapid, sensitive, and reproducible without the need for expensive, specialized facilities or the need for special precautions to protect personnel. Quantification of the label is preferably relatively independent of variables such as temperature and the composition of the mixture to be assayed.

A wide variety of labels have been developed, each with particular advantages and disadvantages. For example, radioactive labels are quite versatile, and can be detected at very low concentrations. Such labels are, however, expensive, hazardous, and their use requires sophisticated equipment and trained personnel. Thus, there is wide interest in non-radioactive labels, particularly in labels that are observable by spectrophotometric, spin resonance and luminescence techniques, and reactive materials, such as enzymes that produce such molecules.

Labels that are detectable using fluorescence spectroscopy are of particular interest, because of the large number of such labels that are known in the art. Moreover, the literature is replete with syntheses of fluorescent labels that are derivatized to allow their facile attachment to other molecules, and many such fluorescent labels are commercially available.

In addition to being directly detected, many fluorescent labels operate to quench the fluorescence of an adjacent second fluorescent label. Because of its dependence on the distance and the magnitude of the interaction between the quencher and the fluorophore, the quenching of a fluorescent species provides a sensitive probe of molecular conformation and binding, or other, interactions. An excellent example of the use of fluorescent reporter quencher pairs is found in the detection and analysis of nucleic acids.

Conventional organic fluorophores generally have short fluorescence lifetimes, on the order of nanoseconds (ns), which is generally too short for optimal discrimination from background fluorescence. An alternative detection scheme, which is theoretically more sensitive than conventional fluorescence, is time-resolved luminescence. According to this method, a chelated lanthanide metal with a long radiative lifetime is attached to a molecule of interest. Pulsed excitation combined with a gated detection system allows for effective discrimination against short-lived background emission. For example, using this approach, the detection and quantification of DNA hybrids via an europium-labeled antibody has been demonstrated (Syvanen et al., *Nucleic Acids Research* 14: 1017-1028 (1986)). In addition, biotinylated DNA was measured in microtiter wells using Eu-labeled streptavidin (Dahlen, *Anal. Biochem.* (1982), 164: 78-83). A disadvantage, however, of these types of assays is that the label must be washed from the probe and its luminescence developed in an enhancement solution.

In view of the predictable practical advantages it has been generally desired that the lanthanide chelates employed should exhibit a delayed luminescence with decay times of more than 10 µs. The luminescence of many of the known luminescent chelates tends to be inhibited by water. As water is generally present in an assay, particularly an immunoassay system, lanthanide complexes that undergo inhibition of luminescence in the presence of water are viewed as somewhat unfavorable or impractical for many applications. Moreover, the short luminescence decay times is considered a disadvantage of these compounds. This inhibition is due to the affinity of the lanthanide ions for coordinating water molecules. When the lanthanide ion has coordinated water molecules, the absorbed light energy (excitation energy) is quenched rather than being emitted as luminescence.

Thus, lanthanide chelates, particularly coordinatively saturated chelates that exhibit excellent luminescence properties are highly desirable. Alternatively, coordinatively unsaturated lanthanide chelates exhibiting acceptable luminescence in the presence of water are also advantageous. Such chelates that are derivatized to allow their conjugation to one or more components of an assay find use in a range of different assay formats. The present invention provides these and other such compounds and assays using these compounds. Hydroxy-isophthalamide (IAM) complexes of lanthanide ions such as $Tb^{3+}$ are potentially useful in a variety of biological applications. Of particular importance for biological applications is that these complexes exhibit kinetic stability in aqueous solutions at concentrations at or below nM levels.

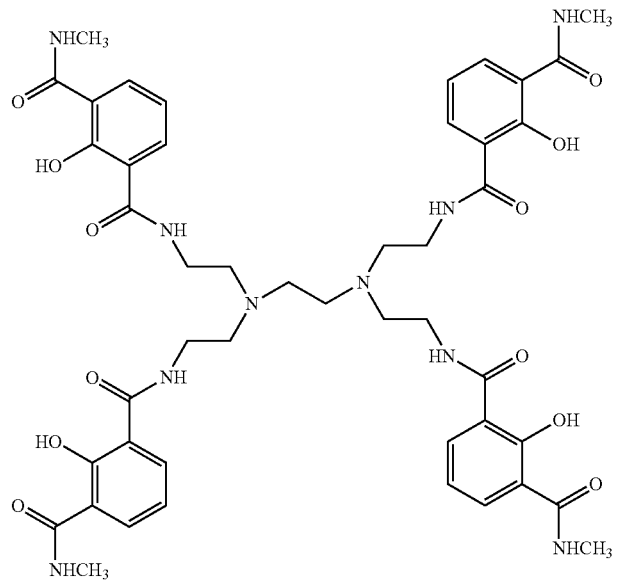

1
H(2,2)IAM

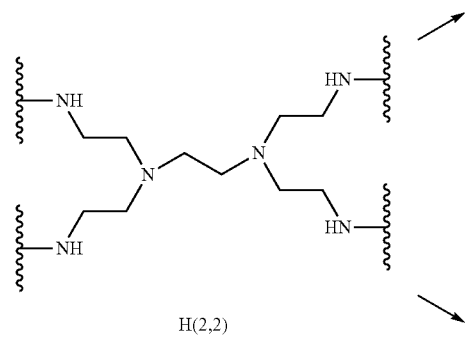

H(2,2)

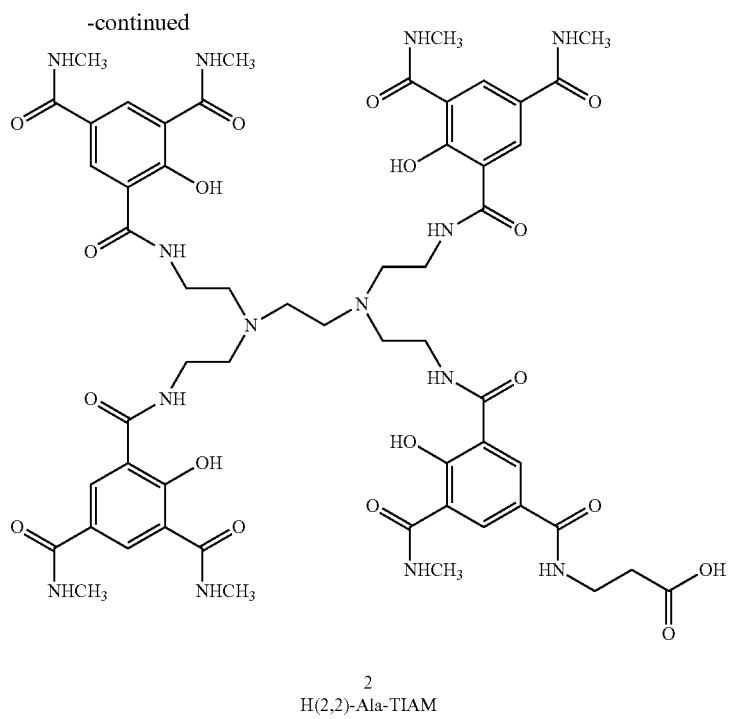

2
H(2,2)-Ala-TIAM

Hydroxyisophthalamide ligands useful in applications requiring luminescence have been described (Petoud et al., *J. Am. Chem. Soc.* 2003, 125, 13324-13325; U.S. Pat. No. 7,018,850 to Raymond et al.). The H(2,2) backbone has been employed to synthesize isophthalamide-based ligands such as 1 and 2 in FIG. 1. Those octadentate ligands display relatively high thermodynamic stability when chelated to trivalent lanthanide ions. The functionalized TIAM ligand 2 has been conjugated to biomolecules and used as a donor in TR-LRET studies (Johansson et al., *J. Am. Chem. Soc.* 2004, 126(50):16451-16455).

However, a need for luminescent complexes, which are stable under biologically relevant conditions and at low concentrations, and which simultaneously exhibit low non-specific interactions with proteins, remains. The current invention addresses these and other needs.

SUMMARY OF THE INVENTION

This invention provides a new class of macrocyclic ligands and metal complexes thereof. In particular, the invention provides luminescent lanthanide complexes. Even more particularly, the invention provides luminescent terbium and europium complexes. These complexes exhibit high stability and solubility in aqueous media as well as high quantum yields of lanthanide ion luminescence in water without external augmentation, such as by micelles or fluoride. The complexes are formed between a metal ion of the lanthanide series and a new class of macrocyclic ligands. Preferred ligands incorporate hydroxy-isophthalamide moieties within their structure and are characterized by surprisingly low non-specific binding to a variety of different polypeptides such as antibodies and proteins. Due to their unique chemical and physicochemical properties the complexes of the present invention could find use in any application requiring luminescence in aqueous media, including medical diagnostics and bioanalytical assay systems.

Thus, in a first aspect, the current invention provides a compound having a structure according to Formula (I):

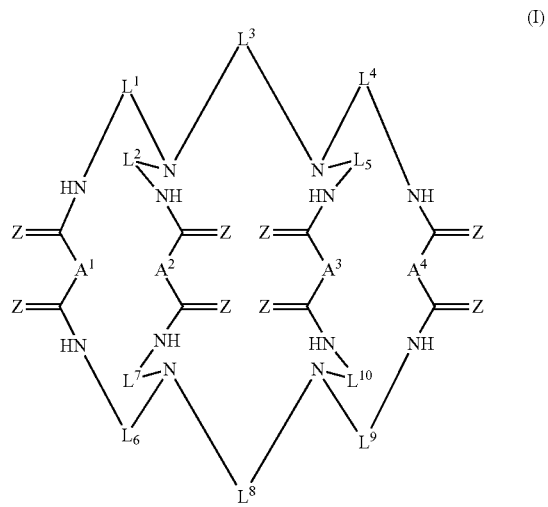

wherein the compound is covalently modified with at least one functional moiety.

In Formula I, each Z is a member independently selected from O and S. $L^1$, $L^2$, $L^3$, $L^4$, $L^5$, $L^6$, $L^7$, $L^8$, $L^9$ and $L^{10}$ are linker groups independently selected from substituted or unsubstituted alkyl, substituted or unsubstituted heteroalkyl, substituted or unsubstituted aryl, substituted or unsubstituted heteroaryl and substituted or unsubstituted heterocycloalkyl.

$A^1$, $A^2$, $A^3$ and $A^4$ are members independently selected from the following structure:

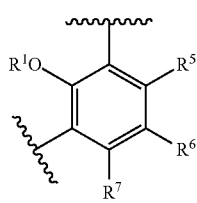

wherein each $R^1$ is a member independently selected from H, an enzymatically labile group, a hydrolytically labile group, a metabolically labile group and a single negative charge. Each $R^5$, $R^6$ and $R^7$ is a member independently selected from H, substituted or unsubstituted alkyl, substituted or unsubstituted heteroalkyl, halogen, CN, $CF_3$, acyl, $-SO_2NR^{17}R^{18}$, $-NR^{17}R^{18}$, $-OR^{17}$, $-S(O)_2R^{17}$, $-C(O)R^{18}$, $-COOR^{17}$, $-CONR^{17}R^{18}$, $-S(O)_2OR^{17}$, $-OC(O)R^{17}$, $-C(O)NR^{17}R^{18}$, $-NR^{17}C(O)R^{18}$, $-NR^{17}SO_2R^{18}$ and $-NO_2$, wherein $R^6$ and a member selected from $R^5$, $R^7$ and combinations thereof are optionally joined to form a ring system which is a member selected from substituted or unsubstituted cycloalkyl, substituted or unsubstituted heterocycloalkyl, substituted or unsubstituted aryl and substituted or unsubstituted heteroaryl.

$R^{17}$ and $R^{18}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^{17}$ and $R^{18}$, together with the atoms to which they are attached, are optionally joined to form a 5- to 7-membered ring.

In a second aspect, the invention provides a luminescent complex formed between at least one metal ion and a compound of the invention.

In a third aspect, the invention provides a method of detecting the presence or absence of an analyte in a sample. The method comprises (a) contacting the sample and a composition including a complex of the invention; (b) exciting the complex; and (c) detecting luminescence from the complex. In one example, the presence or absence of the analyte is indicated by the absence or presence of luminescence from the complex.

In a fourth aspect, the invention provides a method of detecting the presence or absence of an analyte in a sample. The method includes (a) contacting the sample and a composition including a complex of the invention, and a luminescence modifying group, wherein energy can be transferred between the complex and the luminescence modifying group when the complex is excited, and wherein the complex and the luminescence modifying group can be part of the same molecule or be part of different molecules; and (b) exciting said complex; and (c) determining the luminescent property of the sample, wherein the presence or absence of the analyte is indicated by the luminescent property of the sample. In one example, the presence or absence of the analyte in the sample is indicated by a change in the luminescent property of the sample.

BRIEF DESCRIPTION OF THE DRAWINGS

FIG. 1 is a chart indicating the kinetic stability of compound 1 under various conditions at room temperature.

FIG. 2 is a chart indicating the kinetic stability of compound 3 under various conditions at room temperature.

DETAILED DESCRIPTION OF THE INVENTION

Definitions

Figure 3:
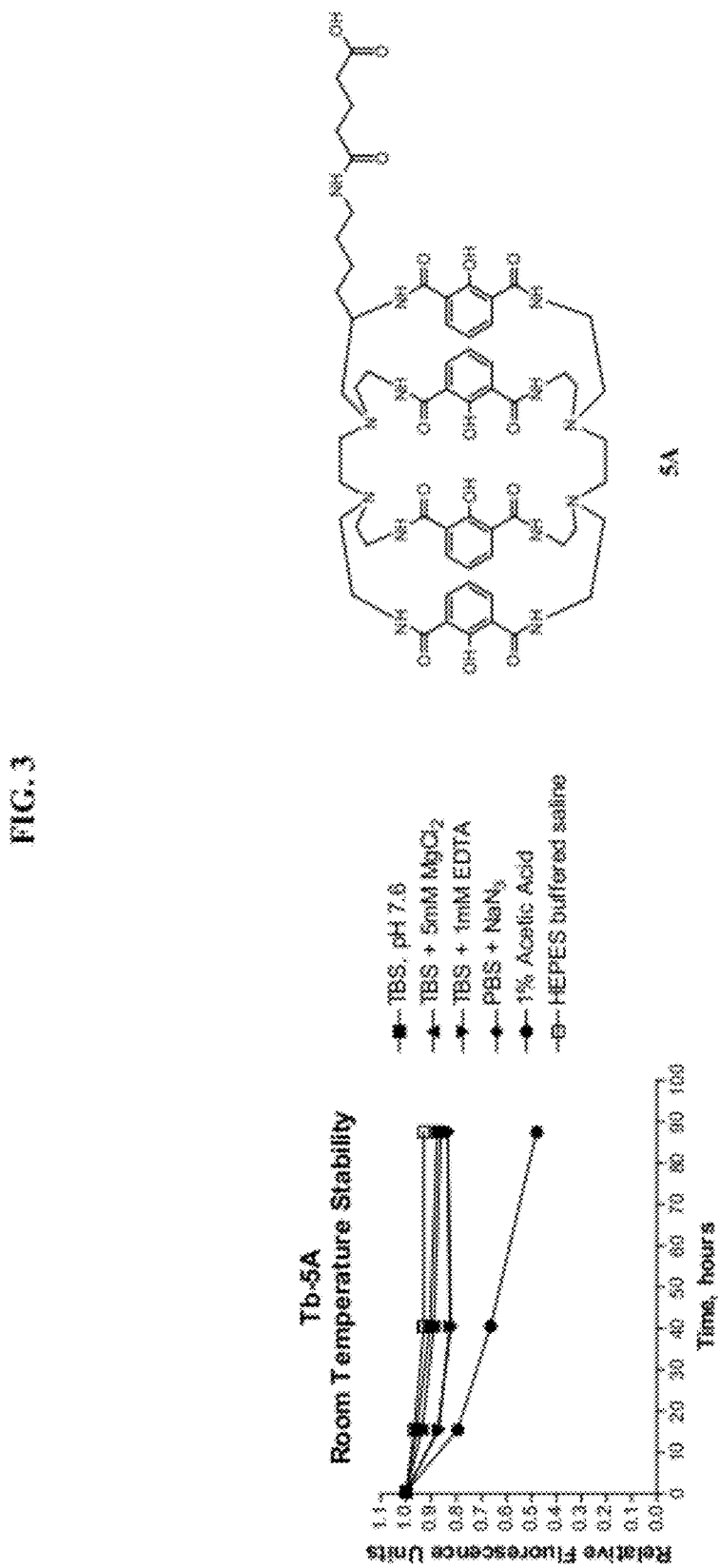
FIG. 3 is a chart indicating the kinetic stability of compound 5A under various conditions at room temperature.

"Analyte", as used herein, means any compound or molecule of interest for which a diagnostic test is performed, such as a biopolymer or a small molecular bioactive material. An analyte can be, for example, a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, lipid etc., without limitation.

As used herein, "energy transfer" refers to the process by which the light emission of a luminescent group is altered by a luminescence-modifying group. When the luminescence-modifying group is a quenching group then the light emission from the luminescent group is attenuated (quenched). Energy transfer mechanisms include luminescence resonance energy transfer by dipole-dipole interaction (e.g., in longer range energy transfer) or electron transfer (e.g., across shorter distances). While energy transfer is often based on spectral overlapping of the emission spectrum of the luminescent group and the absorption spectrum of the luminescence-modifying group, (in addition to distance between the groups) it has been demonstrated that spectral overlap is not necessarily required for energy transfer to occur (see e.g., Latva et al., U.S. Pat. No. 5,998,146, which is incorporated herein by reference). It is to be understood that any reference to "energy transfer" herein encompasses all mechanistically-distinct phenomena.

"Energy transfer pair" is used to refer to a group of molecules that participate in energy transfer. Such complexes may comprise, for example, two luminescent groups, which may be different from one-another and one quenching group, two quenching groups and one luminescent group, or multiple luminescent groups and multiple quenching groups. In cases where there are multiple luminescent groups and/or multiple quenching groups, the individual groups may be different from one another. Typically, one of the molecules acts as a luminescent group, and another acts as a luminescence-modifying group. The preferred energy transfer pair of the invention comprises a luminescent group and a quenching group of the invention. There is no limitation on the identity of the individual members of the energy transfer pair described herein. All that is required is that the spectroscopic properties of the energy transfer pair as a whole change in some measurable way if the distance between the individual members is altered by some critical amount.

As used herein, "luminescence-modifying group" refers to a molecule of the invention that can alter in any way the luminescence emission from a luminescent group. A luminescence-modifying group generally accomplishes this through an energy transfer mechanism. Depending on the identity of the luminescence-modifying group, the luminescence emission can undergo a number of alterations, including, but not limited to, attenuation, complete quenching, enhancement, a shift in wavelength, a shift in polarity, and a change in luminescence lifetime. One example of a luminescence-modifying group is a fluorescence-modifying group. Another exemplary luminescence-modifying group is a quenching group.

As used herein, "quenching group" refers to any luminescence-modifying group of the invention that can attenuate at least partly the light emitted by a luminescent group. This attenuation is referred to herein as "quenching". Hence, excitation of the luminescent group in the presence of the quenching group leads to an emission signal that is less intense than expected, or even completely absent. Quenching typically occurs through energy transfer between the luminescent group and the quenching group.

"Fluorescence resonance energy transfer" or "FRET" is used interchangeably with "FET", and "luminescence resonance energy transfer (LRET)" and refers to an energy transfer phenomenon in which the light emitted by an excited luminescent group is absorbed at least partially by a luminescence-modifying group of the invention. The luminescence-modifying group can, for instance, be a quenching group. LRET depends on energy transfer between the luminescent group and the luminescence-modifying group. LRET also depends on the distance between the luminescence modifying group and the luminescent group.

"High dilution" or "H.D." conditions as discussed herein refers to conditions which are better suited to obtain the desired product rather than undesired products. In performing chemical reactions especially cyclization reactions, high dilution conditions are achieved by keeping the concentration of one or more reactants low enough to reduce the formation of undesired polymeric by-products. Different reactions have different reactant concentration requirements that can be worked out to obtain the desired yield of the desired product. One of ordinary skill in the art would be able to adjust the reactant concentrations in order to achieve the desired yield of the desired product. In an exemplary embodiment, the compounds of the invention that are prepared under high dilution conditions are prepared in such as way that the concentration of at least one reactant is very low (approximately $1\times10-5$ M or less). Desired products can be obtained for reactions at higher concentrations, but the yield of desired products will be lower and the yields of undesired products will be higher.

"Moiety" refers to the radical of a molecule that is attached to another moiety.

The term "targeting moiety" is intended to mean any moiety attached to the complexes of the invention. The targeting moiety can be a small molecule, which is intended to include both non-peptides and peptides. The targeting group can also be a macromolecule, which includes saccharides, lectins, receptors, ligands for receptors, proteins such as BSA, antibodies, nucleic acids, solid supports and so forth. The targeting group can also be a lipid as well as a polymer, such as a plastic surface, a poly-ethyleneglycol derivative and the like.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids, phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Modifications can also include 3' and 5' modifications such as capping with a SL, a fluorophore or another moiety.

"Peptide" refers to a polymer in which the monomers are amino acids and are joined together through amide bonds, alternatively referred to as a polypeptide. When the amino acids are alpha-amino acids, either the L-optical isomer or the D-optical isomer can be used. Additionally, unnatural amino acids, for example, beta.-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. The term "peptide" or "polypeptide", as used herein, refers to naturally occurring as well as synthetic peptides. In addition, peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N, S, B and Si may be placed at any interior position of the heteroalkyl group or at the position at which the alkyl group is attached to the remainder of the molecule.

Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted heteroalkyl, substituted or unsubstituted heterocycloalkyl, substituted or unsubstituted aryl, substituted or unsubstituted heteroaryl, halogen, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"" and R' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R' and R' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "heteroatom" includes oxygen (O), nitrogen (N), sulfur (S), silicon (Si) and boron (B).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The present invention includes all salt forms of those molecules that contain ionizable functional groups, such as basic and acidic groups. The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

When a residue (such as R$^1$, R$^2$, R$^3$ and R$^4$) is defined herein as a single negative charge, then the residue can optionally include a cationic counterion. The resulting salt form of the compound is encompassed in the structure as presented.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The graphic representations of racemic, ambiscalemic and scalemic or enantiomerically pure compounds used herein are taken from Maehr, *J. Chem. Ed.*, 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

The terms "enantiomeric excess" and diastereomeric excess" are used interchangeably herein. Compounds with a single stereocenter are referred to as being present in "enantiomeric excess," those with at least two stereocenters are referred to as being present in "diastereomeric excess."

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Introduction

The present invention provides a class of luminescent probes that are based on metal chelates, which are formed between the metal ion and a novel class of macrocyclic ligands. In particular, the invention provides luminescent lanthanide complexes. Even more particularly, the invention provides luminescent terbium and europium complexes. These complexes exhibit high stability as well as high quantum yields of lanthanide ion luminescence in aqueous media without the need for secondary activating agents, such as by micelles or fluoride. Preferred ligands incorporate hydroxyphthalamide moieties within their macrocyclic structure and are characterized by surprisingly high kinetic stability and unexpectedly low, non-specific binding to a variety of different polypeptides such as antibodies and proteins. These characteristics distinguish them from known, open-structured ligands.

The value of these lanthanide complexes derives from their high quantum efficiencies and relatively high absorption coefficients. These properties make ligands such as compound 5 useful for homogeneous time resolved luminescence resonance energy transfer (TR-LRET) applications where donor and acceptor molecules are used at low concentrations. Complexes of the present invention could find use in any application requiring strong luminescence under aqueous conditions including medical diagnostics and bioanalytical assay systems, such as immunoassays, peptide cleavage assays, DNA reporter assays and the like. In addition, these complexes and their derivatives may find wide applicability in nanotechnology (incorporation into particles) and material science where the complexes could be embedded in solid materials that allow for the transmission of light.

The fluorophores of the invention can be used with other fluorophores or quenchers as components of energy transfer probes. Many luminescent or non-luminescent labels are useful in combination with the complexes of the invention and many such labels are available from commercial sources, such as SIGMA (Saint Louis) or Invitrogen, that are known to those of skill in the art. Furthermore, those of skill in the art will recognize how to select an appropriate fluorophore for a particular application and, if it is not readily available, will be able to synthesize the necessary fluorophore or quencher de novo or synthetically modify commercially available luminescent compounds to arrive at the desired luminescent label.

In addition to small-molecule fluorophores, naturally occurring fluorescent proteins and engineered analogues of such proteins are useful with the compounds of the present invention. Such proteins include, for example, green fluorescent proteins of cnidarians (Ward et al., *Photochem. Photobiol.* 1982, 35:803-808; Levine et al., *Comp. Biochem. Physiol.* 1982, 72B:77 85), yellow fluorescent protein from Vibrio fischeri strain (Baldwin et al., *Biochemistry* 1990, 29:5509 15), Peridinin-chlorophyll from the dinoflagellate *Symbiodinium* sp. (Morris et al., *Plant Molecular Biology* 1994, 24:673:77), phycobiliproteins from marine cyanobacteria, such as *Synechococcus*, e.g., phycoerythrin and phycocyanin (Wilbanks et al., *J. Biol. Chem.* 1993, 268:1226 35), and the like.

The compounds of the invention can be used as probes, as tools for separating particular ions from other solutes, as probes in microscopy, enzymology, clinical chemistry, molecular biology and medicine. The compounds of the invention are also useful as therapeutic agents and as diagnostic agents in imaging methods. Moreover, the compounds of the invention are useful as components of optical amplifiers of light, waveguides and the like. Furthermore, the compounds of the invention can be incorporated into inks and dyes, such as those used in the printing of currency and other instruments.

In one embodiment, the compounds of the invention show luminescence after exciting them in any manner known in the art, including, for example, with light or electrochemical energy (see, for example, Kulmala et al, *Analytica Chimica Acta* 1999, 386:1). The luminescence can, in the case of chiral compounds of the invention, be circularly polarized (see, for example, Riehl et al., *Chem. Rev.* 1986, 86:1).

The compounds, probes and methods discussed in the following sections are generally representative of the compositions of the invention and the methods in which such compositions can be used. The following discussion is intended as illustrative of selected aspects and embodiments of the present invention and it should not be interpreted as limiting the scope of the present invention.

Compositions

In a first aspect, the present invention provides a compound having a structure which is a member selected from:

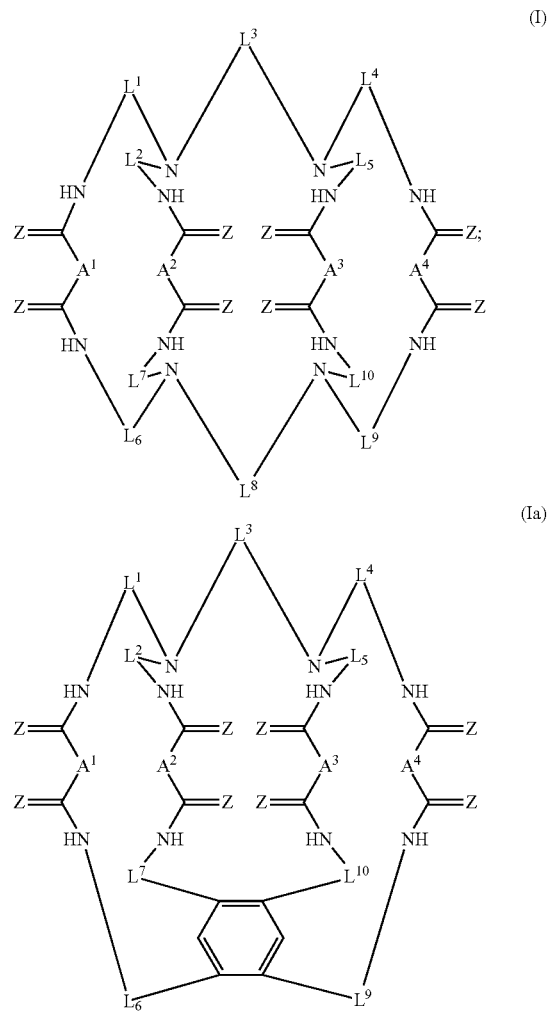

In Formulae I and Ia, each Z is a member independently selected from O and S. $L^1, L^2, L^3, L^4, L^5, L^6, L^7, L^8, L^9$ and $L^{10}$ are linker groups independently selected from substituted or unsubstituted alkyl, substituted or unsubstituted heteroalkyl, substituted or unsubstituted aryl, substituted or unsubstituted heteroaryl and substituted or unsubstituted heterocycloalkyl. $A^1, A^2, A^3$ and $A^4$ are building blocks, which are members independently selected from substituted or unsubstituted aryl, substituted or unsubstituted heteroaryl, substituted or unsubstituted cycloalkyl, substituted or unsubstituted heterocycloalkyl and a fused ring system.

In one embodiment, the compounds of Formulae I and Ia are covalently modified with a functional moiety. In an exemplary embodiment, at least one of $A^1, A^2, A^3, A^4, L^1, L^2, L^3, L^4, L^5, L^6, L^7, L^8, L^9$ and $L^{10}$ is substituted with a functional moiety.

In another embodiment, the macrocyclic ligands of the invention are based on hydroxy phthalic acid or hydroxy isophthalic acid or combinations thereof as the building blocks. In an exemplary embodiment according to this aspect, $A^1$, $A^2$, $A^3$ and $A^4$ have a structure according to the following formula:

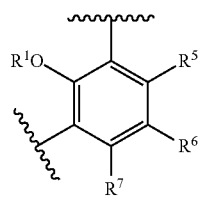

wherein each general structure for $A^1$, $A^2$, $A^3$ and $A^4$ is a member independently selected. Each $R^1$ is a member independently selected from H, an enzymatically labile group, a hydrolytically labile group, a metabolically labile group and a single negative charge. Each $R^5$, $R^6$ and $R^7$ is a member independently selected from H, substituted or unsubstituted alkyl, substituted or unsubstituted heteroalkyl, halogen, CN, $CF_3$, acyl, $-SO_2NR^{17}R^{18}$, $-NR^{17}R^{18}$, $-OR^{17}$, $-S(O)_2R^{17}$, $-COOR^{17}$, $-S(O)_2OR^{17}$, $-OC(O)R^{17}$, $-C(O)NR^{17}R^{18}$, $-NR^{17}C(O)R^{18}$, $-NR^{17}SO_2R^{18}$, and $-NO_2$, wherein $R^6$ and a member selected from $R^5$, $R^7$ and combinations thereof are optionally joined to form a ring system, which is a member selected from substituted or unsubstituted cycloalkyl, substituted or unsubstituted heterocycloalkyl, substituted or unsubstituted aryl and substituted or unsubstituted heteroaryl.

$R^{17}$ and $R^{18}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^{17}$ and $R^{18}$, together with the atoms to which they are attached, are optionally joined to form a 5- to 7-membered ring.

In another exemplary embodiment, the compound of the invention has the structure:

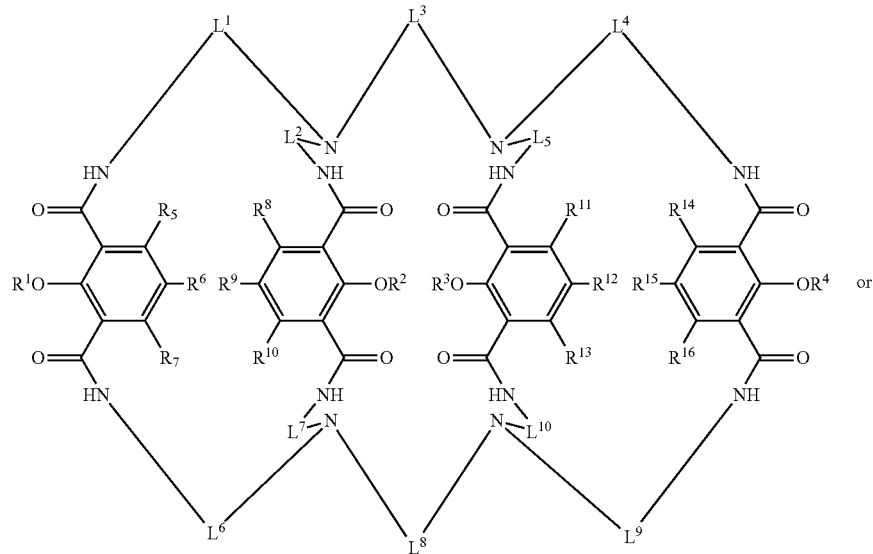

(II)

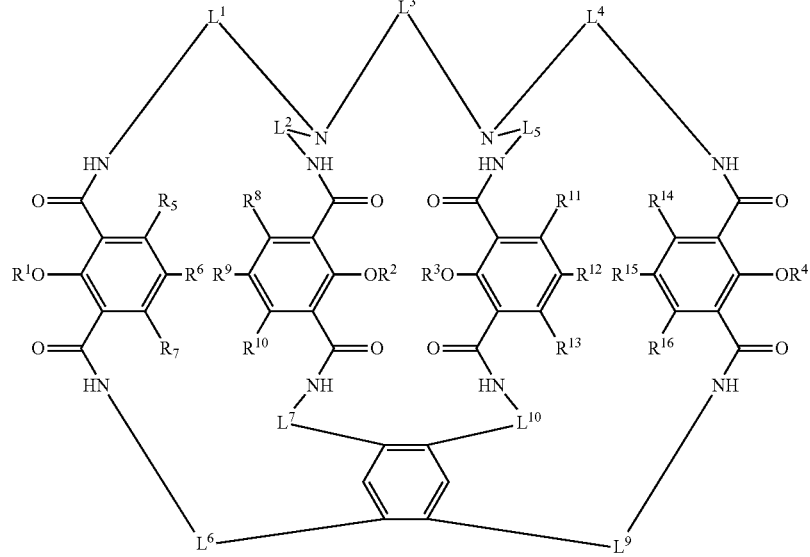

(IIa)

wherein $R^1$, $R^2$, $R^3$ and $R^4$ are members independently selected from H, an enzymatically labile group, a hydrolytically labile group, a metabolically labile group and a single negative charge. Exemplary compounds include those in which at least one of $L^1$, $L^2$, $L^3$, $L^4$, $R^5$, $R^6$, $R^7$, $R^8$, $R^9$ $R^{10}$, $R^{11}$, $R^{12}$, $R^{13}$, $R^{14}$, $R^{15}$ and $R^{16}$ is substituted with a functional moiety, and preferably at least one of $L^1$, $L^2$, $L^3$, $L^4$, $L^5$, $L^6$, $L^7$, $L^8$, $L^9$ and $L^{10}$ is substituted with a functional moiety.

$R^5$, $R^6$, $R^7$, $R^8$, $R^9 R^{10}$, $R^{11}$, $R^{12}$, $R^{13}$, $R^{14}$, $R^{15}$, and $R^{16}$ are members independently selected from H, substituted or unsubstituted alkyl, substituted or unsubstituted heteroalkyl, halogen, CN, $CF_3$, acyl, $-SO_2NR^{17}R^{18}$, $NR^{17}R^{18}$, $-OR^{17}$, $-S(O)_2R^{17}$, $-COOR^{17}$, $-S(O)_2OR^{17}$, $-OC(O)R^{17}$, $-C(O)NR^{17}R^{18}$, $C(O)R^{18}$, $-NR^{17}C(O)R^{18}$, $-NR^{17}SO_2R^{18}$, and $-NO_2$, wherein $R^{17}$ and $R^{18}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, wherein $R^{17}$ and $R^{18}$, together with the atoms to which they are attached, are optionally joined to form a 5- to 7-membered ring. $R^6$ and a member selected from $R^5$, $R^7$ and combinations thereof are optionally joined to form a ring system. Likewise, $R^9$ and a member selected from $R^8$, $R^{10}$ and combinations thereof are optionally joined to form a ring system. In addition, $R^{12}$ and a member selected from $R^{11}$, $R^{13}$ and combinations thereof are optionally joined to form a ring system, wherein the ring system is a member selected from substituted or unsubstituted cycloalkyl, substituted or unsubstituted heterocycloalkyl, substituted or unsubstituted aryl and substituted or unsubstituted heteroaryl.

In an exemplary embodiment, in the compound of Formulae (I) or (Ia), $L^1$, $L^2$, $L^3$, $L^4$, $L^5$, $L^6$, $L^7$, $L^8$, $L^9$ and $L^{10}$ are members independently selected from substituted or unsubstituted heteroalkylene and substituted or unsubstituted $C_1$ to $C_6$ alkylene. In an exemplary embodiment, in the compound of Formulae (I) or (Ia), $L^1$, $L^2$, $L^4$, $L^5$ are members independently selected from substituted or unsubstituted ethylene. In an exemplary embodiment, in the compound of Formulae (I) or (Ia), $L^6$, $L^7$, $L^9$, $L^{10}$ are members independently selected from substituted or unsubstituted ethylene. In an exemplary embodiment, in the compound of Formulae (I) or (Ia), $L^6$, $L^7$, $L^9$, $L^{10}$ are members independently selected from substituted or unsubstituted methylene. In an exemplary embodiment, in the compound of Formulae (I) or (Ia), $L^3$ is substituted or unsubstituted ethylene. In an exemplary embodiment, in the compound of Formulae (I) or (Ia), $L^8$ is substituted or unsubstituted ethylene. In an exemplary embodiment, in the compound of Formulae (I) or (Ia), $L^1$, $L^2$, $L^3$, $L^4$ and $L^5$ are substituted or unsubstituted ethylene. In an exemplary embodiment, in the compound of Formulae (I) or (Ia), $L^6$, $L^7$, $L^8$, $L^9$, $L^{10}$ are members independently selected from substituted or unsubstituted ethylene. In an exemplary embodiment, in the compound of Formulae (I) or (Ia), $L^6$, $L^7$, $L^8$, $L^9$, $L^{10}$ are members independently selected from substituted or unsubstituted methylene.

In an exemplary embodiment, in the compound of Formulae (II) or (IIa), $L^1$, $L^2$, $L^3$, $L^4$, $L^5$, $L^6$, $L^7$, $L^8$, $L^9$ and $L^{10}$ are members independently selected from substituted or unsubstituted heteroalkylene and substituted or unsubstituted $C_1$ to $C_6$ alkylene. In an exemplary embodiment, in the compound of Formulae (II) or (IIa), $L^1$, $L^2$, $L^4$, $L^5$ are members independently selected from substituted or unsubstituted ethylene. In an exemplary embodiment, in the compound of Formulae (II) or (IIa), $L^6$, $L^7$, $L^9$, $L^{10}$ are members independently selected from substituted or unsubstituted ethylene. In an exemplary embodiment, in the compound of Formulae (II) or (IIa), $L^6$, $L^7$, $L^9$, $L^{10}$ are members independently selected from substituted or unsubstituted methylene. In an exemplary embodiment, in the compound of Formulae (II) or (IIa), $L^3$ is substituted or unsubstituted ethylene. In an exemplary embodiment, in the compound of Formulae (II) or (IIa), $L^8$ is substituted or unsubstituted ethylene. In an exemplary embodiment, in the compound of Formulae (II) or (IIa), $L^1$, $L^2$, $L^3$, $L^4$ and $L^5$ are substituted or unsubstituted ethylene. In an exemplary embodiment, in the compound of Formulae (II) or (IIa), $L^6$, $L^7$, $L^8$, $L^9$, $L^{10}$ are members independently selected from substituted or unsubstituted ethylene. In an exemplary embodiment, in the compound of Formulae (II) or (IIa), $L^6$, $L^7$, $L^8$, $L^9$, $L^{10}$ are members independently selected from substituted or unsubstituted methylene.

In an exemplary embodiment, in the compound of Formulae (II) or (IIa), $R^5$, $R^6$ and $R^7$ are H. In an exemplary embodiment, in the compound of Formulae (II) or (IIa), $R^8$, $R^9$ and $R^{10}$ are H. In an exemplary embodiment, in the compound of Formulae (II) or (IIa), $R^{11}$, $R^{12}$ and $R^{13}$ are H. In an exemplary embodiment, in the compound of Formulae (II) or (IIa), $R^{14}$, $R^{15}$ and $R^{16}$ are H.

In another exemplary embodiment, $L^1$, $L^2$, $L^3$, $L^4$, $L^5$, $L^6$, $L^7$, $L^8$, $L^9$ and $L^{10}$ are members independently selected from substituted or unsubstituted $C_1$ to $C_6$ alkylene. Exemplary compounds include those in which $L^1$, $L^2$, $L^3$, $L^4$, $L^5$, $L^6$, $L^7$, $L^8$, $L^9$ and $L^{10}$ are members independently selected from substituted or unsubstituted ethylene. An exemplary ligand according to this embodiment has the structure of compound 3:

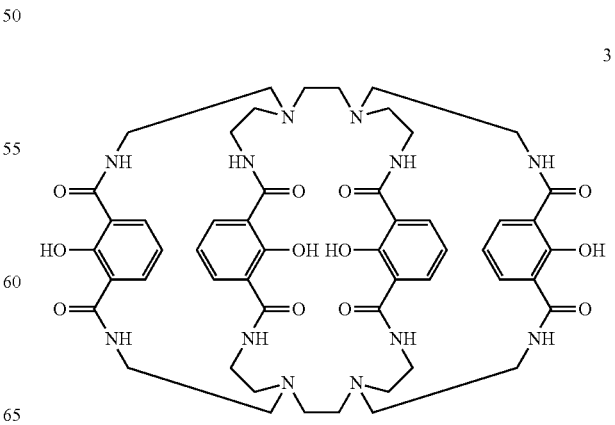

Functional Moiety

In one exemplary embodiment, the compounds of the invention (e.g. ligand 3) are derivatized with a functional moiety. The functional moiety can, for example, be attached to one of the linker units or to one of the building blocks. When two or more functional moieties are used, each can be attached to any of the available linking sites.

In an exemplary embodiment, the functional moiety has the structure:

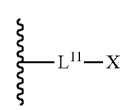

wherein $L^{11}$ is a linker moiety, which is a member selected from substituted or unsubstituted alkyl, substituted or unsubstituted heteroalkyl, substituted or unsubstituted heterocycloalkyl, substituted or unsubstituted aryl and substituted or unsubstituted heteroaryl; and X is a member selected from a reactive functional group and a targeting moiety.

The functional moiety is preferably attached, so that the resulting functionalized ligand will be able to undergo formation of stable metal ion complexes. In an exemplary embodiment, the macrocyclic ligand 3 is derivatized with a functional moiety. FIG. 2 shows preferred derivatization sites for 3.

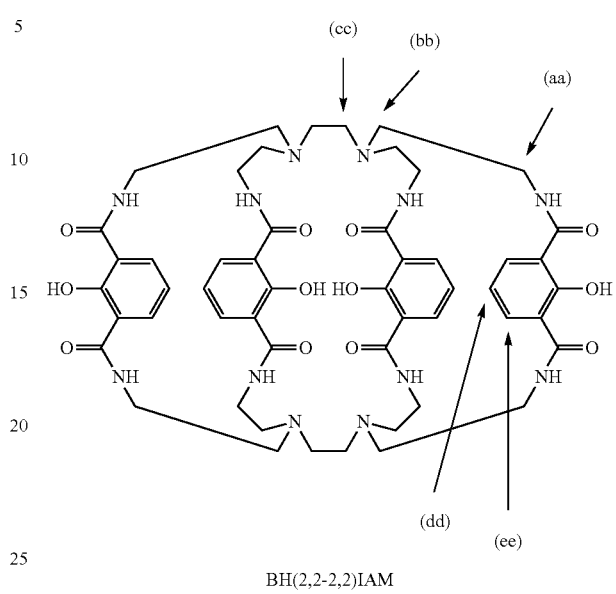

FIG. 2

BH(2,2-2,2)IAM

In one exemplary embodiment, compound 3 is derivatized at position (aa), (bb) or (cc) in FIG. 2. However, ligands, in which alternative positions within the core structure of the ligand (e.g., positions (dd) and (ee)) are derivatized with a functional moiety, are expected to have similarly useful properties.

In an exemplary embodiment, the compound comprises one functional moiety. In another exemplary embodiment, the compound has a structure which is a member selected from:

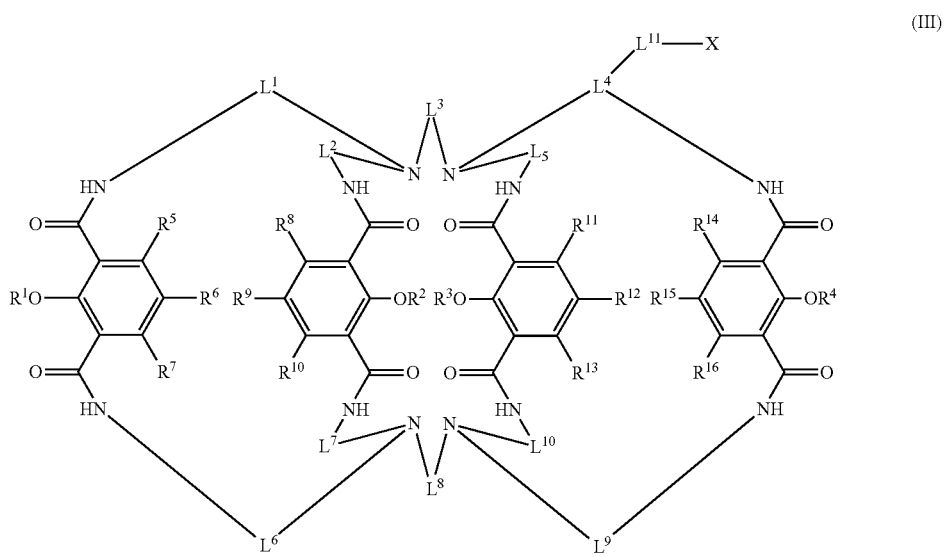

-continued
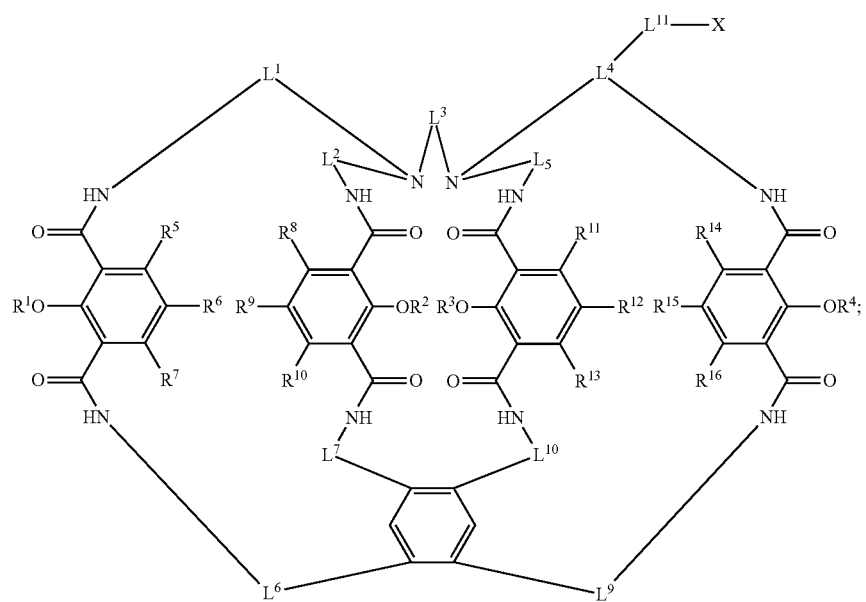
(IIIa)
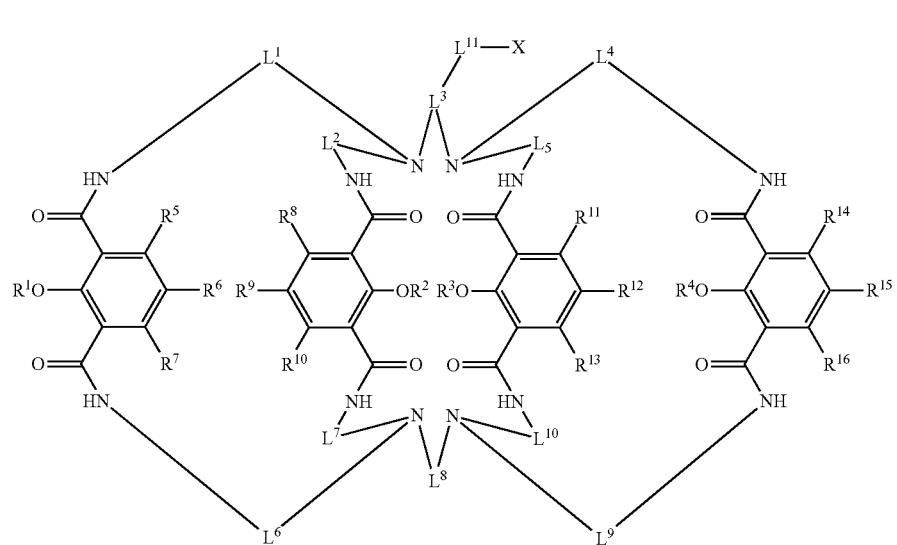
(IV)

-continued
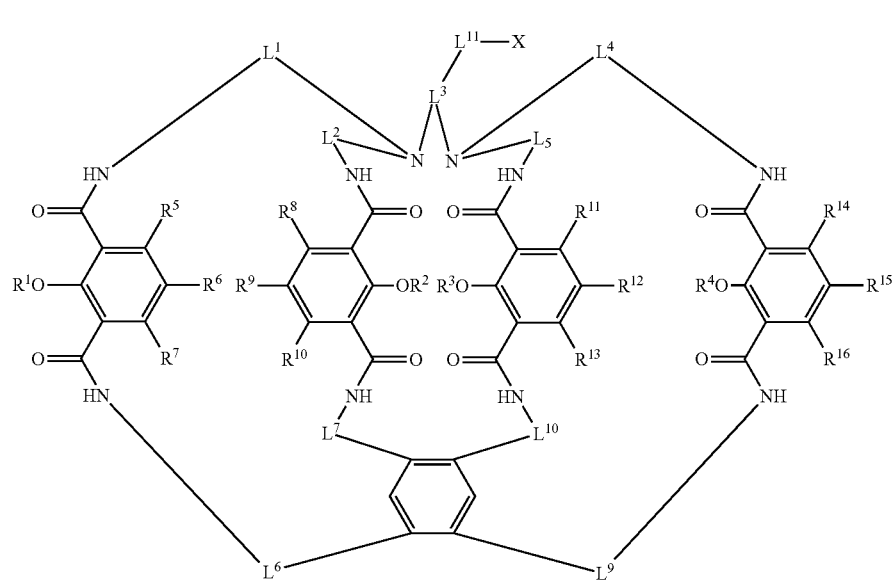
(IVa)
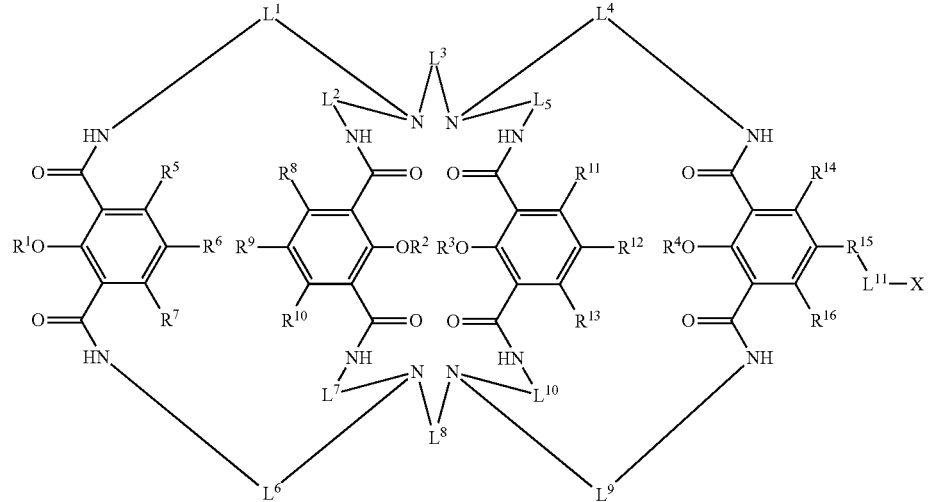
(V)
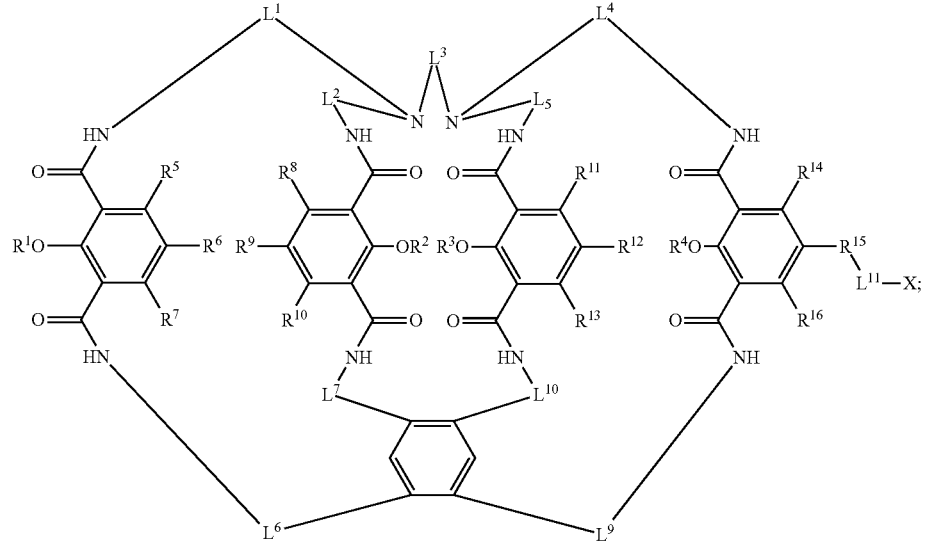
(Va)

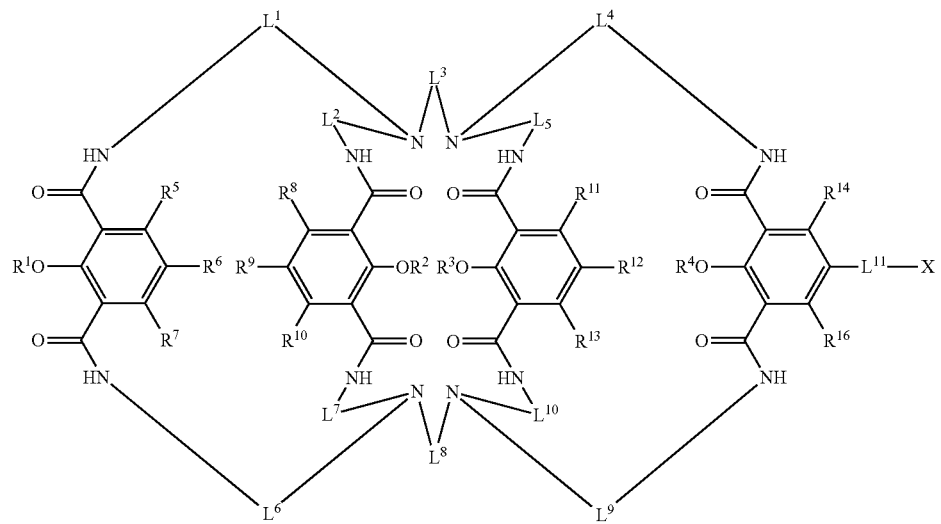
(VI)
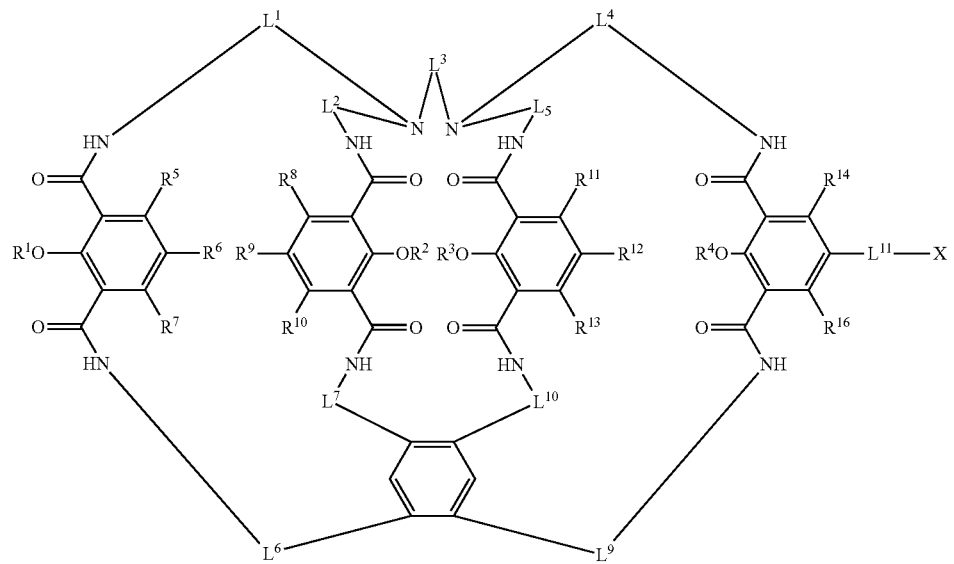
(VIa)
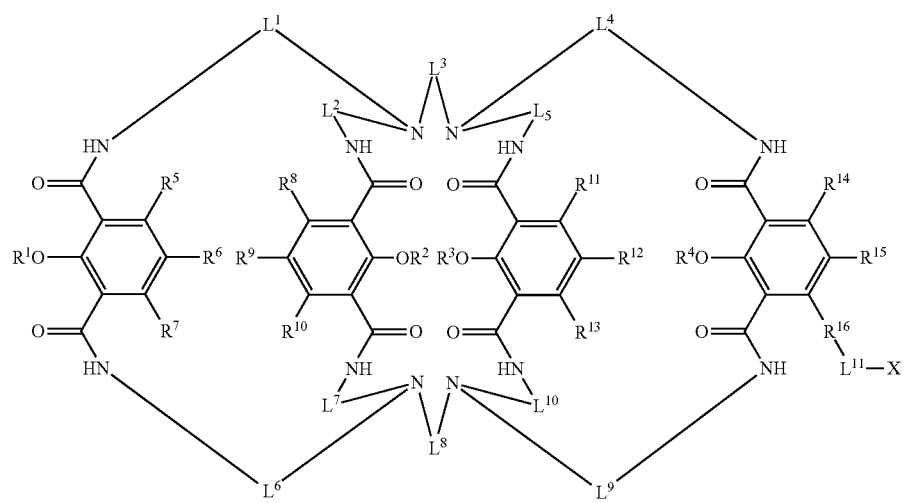
(VII)

-continued
(VIIa)
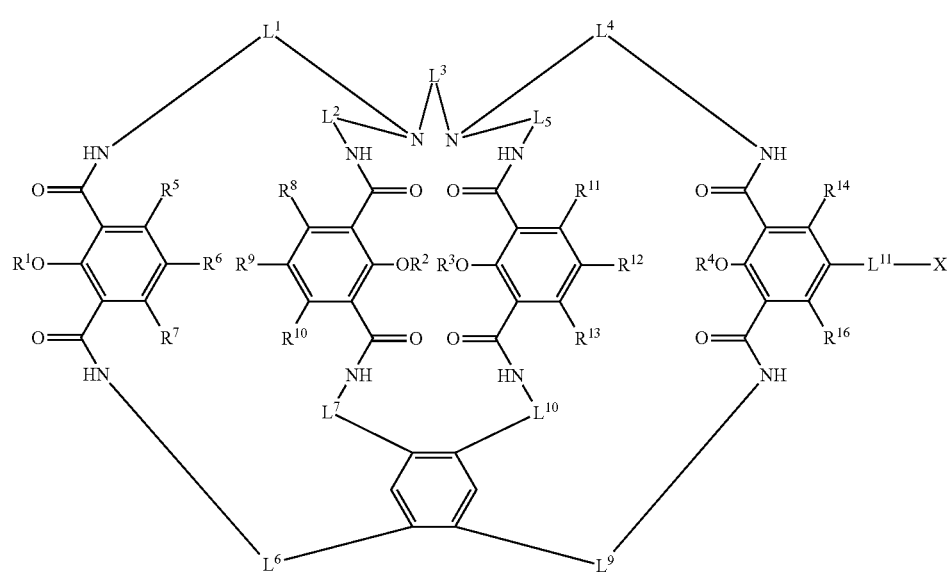
(VIII)
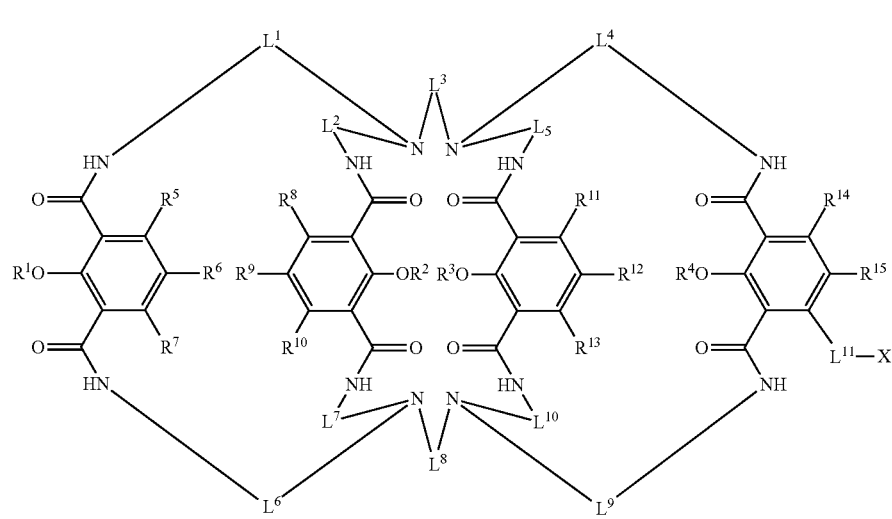
(VIIIa)
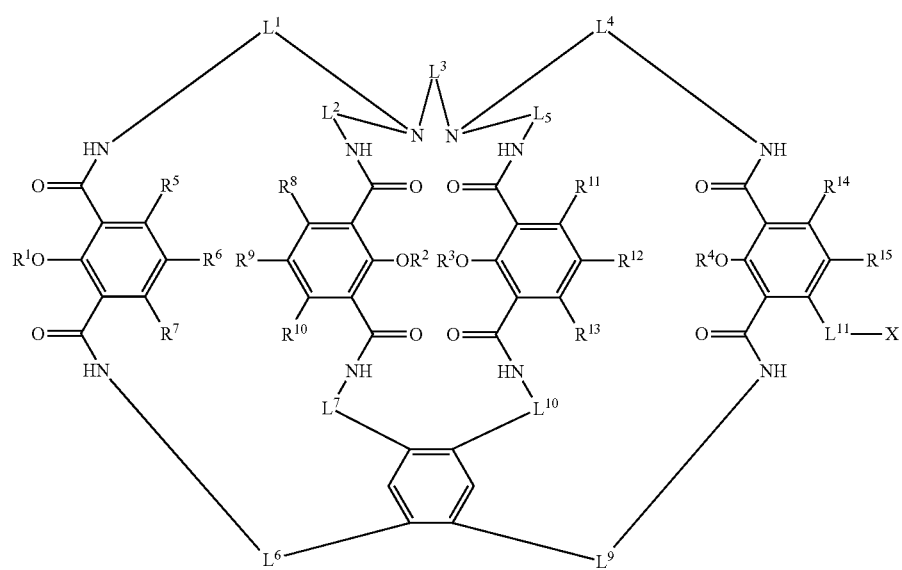

In an exemplary embodiment, in the compound of Formulae (III) or (IIIa) or (IV) or (IVa) or (V) or (Va) or (VI) or (VIa) or (VII) or (VIIa) or (VIII) or (VIIIa), $L^1$, $L^2$, $L^3$, $L^4$, $L^5$, $L^6$, $L^7$, $L^8$, $L^9$ and $L^{10}$ are members independently selected from substituted or unsubstituted $C_1$ to $C_6$ alkylene. In an exemplary embodiment, in the compound of Formulae (III) or (IIIa) or (IV) or (IVa) or (V) or (Va) or (VI) or (VIa) or (VII) or (VIIa) or (VIII) or (VIIIa), $L^1$, $L^2$, $L^4$, $L^5$ are members independently selected from substituted or unsubstituted ethylene. In an exemplary embodiment, in the compound of Formulae (III) or (Ma) or (IV) or (IVa) or (V) or (Va) or (VI) or (VIa) or (VII) or (VIIa) or (VIII) or (VIIIa), $L^6$, $L^7$, $L^9$, $L^{10}$ are members independently selected from substituted or unsubstituted ethylene. In an exemplary embodiment, in the compound of Formulae (III) or (IIIa) or (IV) or (IVa) or (V) or (Va) or (VI) or (VIa) or (VII) or (VIIa) or (VIII) or (VIIIa), $L^6$, $L^7$, $L^9$, $L^{10}$ are members independently selected from substituted or unsubstituted methylene. In an exemplary embodiment, in the compound of Formulae (III) or (Ma) or (IV) or (IVa) or (V) or (Va) or (VI) or (VIa) or (VII) or (VIIa) or (VIII) or (VIIIa), $L^3$ is substituted or unsubstituted ethylene. In an exemplary embodiment, in the compound of Formulae (II) or (IIa), $L^8$ is substituted or unsubstituted ethylene. In an exemplary embodiment, in the compound of Formulae (III) or (IIIa) or (IV) or (IVa) or (V) or (Va) or (VI) or (VIa) or (VII) or (VIIa) or (VIII) or (VIIIa), $L^1$, $L^2$, $L^3$, $L^4$ and $L^5$ are substituted or unsubstituted ethylene. In an exemplary embodiment, in the compound of Formulae (III) or (IIIa) or (IV) or (IVa) or (V) or (Va) or (VI) or (VIa) or (VII) or (VIIa) or (VIII) or (VIIIa), $L^6$, $L^7$, $L^8$, $L^9$, $L^{10}$ are members independently selected from substituted or unsubstituted ethylene. In an exemplary embodiment, in the compound of Formulae (III) or (IIIa) or (IV) or (IVa) or (V) or (Va) or (VI) or (VIa) or (VII) or (VIIa) or (VIII) or (VIIIa), $L^6$, $L^7$, $L^8$, $L^9$, $L^{10}$ are members independently selected from substituted or unsubstituted methylene. In an exemplary embodiment, in a compound described in this paragraph, the composition further comprises a metal, thus forming a complex. In an exemplary embodiment, in a compound described in this paragraph, the metal is a lanthanide. In an exemplary embodiment, in a compound described in this paragraph, the lanthanide is a member selected from Nd, Sm, Eu, Tb, Dy and Yb. In an exemplary embodiment, in a compound described in this paragraph, the lanthanide is Tb. In an exemplary embodiment, in a compound described in this paragraph, the lanthanide is Eu. In another exemplary embodiment, in a compound or complex described in this paragraph, X is a targeting moiety which is a biomolecule. In another exemplary embodiment, in a compound or complex described in this paragraph, X is a targeting moiety which is a biomolecule which is a member selected from a small-molecule ligand, a peptide, a protein, an enzyme, an antibody, an antigen, a nucleic acid, a carbohydrate, a lipid and a pharmacologically active molecule. In another exemplary embodiment, in a compound or complex described in this paragraph, X is a targeting moiety which is a peptide, a protein, an enzyme or an antibody. In another exemplary embodiment, in a compound or complex described in this paragraph, X is targeting moiety which is a nucleic acid. In another exemplary embodiment, in a compound or complex described in this paragraph, X is a targeting moiety which is a carbohydrate. In another exemplary embodiment, in a terbium or europium complex described in this paragraph, X is a targeting moiety which is a biomolecule which is a member selected from a small-molecule ligand, a peptide, a protein, an enzyme, an antibody, an antigen, a nucleic acid, a carbohydrate, a lipid and a pharmacologically active molecule. In another exemplary embodiment, in a terbium or europium complex described in this paragraph, X is a targeting moiety which is a peptide, a protein, an enzyme or an antibody. In another exemplary embodiment, in a terbium or europium complex described in this paragraph, X is a targeting moiety which is a nucleic acid. In another exemplary embodiment, in a terbium or europium complex described in this paragraph, X is a targeting moiety which is a carbohydrate.

In an exemplary embodiment, in the compound of Formulae (III) or (IIIa) or (IV) or (IVa) or (V) or (Va) or (VI) or (VIa) or (VII) or (VIIa) or (VIII) or (VIIIa), $R^5$, $R^6$ and $R^7$ are H. In an exemplary embodiment, in the compound of Formulae (III) or (IIIa) or (IV) or (IVa) or (V) or (Va) or (VI) or (VIa) or (VII) or (VIIa) or (VIII) or (VIIIa), $R^8$, $R^9$ and $R^{16}$ are H. In an exemplary embodiment, in the compound of Formulae (III) or (Ma) or (IV) or (IVa) or (V) or (Va) or (VI) or (VIa) or (VII) or (VIIa) or (VIII) or (VIIIa), $R^{11}$, $R^{12}$ and $R^{13}$ are H. In an exemplary embodiment, in the compound of Formulae (III) or (Ma) or (IV) or (IVa) or (V) or (Va) or (VI) or (VIa) or (VII) or (VIIa) or (VIII) or (VIIIa), $R^{14}$, $R^{15}$ and $R^{16}$ are H. In an exemplary embodiment, in a compound described in this paragraph, the composition further comprises a metal, thus forming a complex. In an exemplary embodiment, in a compound described in this paragraph, the metal is a lanthanide. In an exemplary embodiment, in a compound described in this paragraph, the lanthanide is a member selected from Nd, Sm, Eu, Tb, Dy and Yb. In an exemplary embodiment, in a compound described in this paragraph, the lanthanide is Tb. In an exemplary embodiment, in a compound described in this paragraph, the lanthanide is Eu. In another exemplary embodiment, in a compound or complex described in this paragraph, X is a targeting moiety which is a biomolecule. In another exemplary embodiment, in a compound or complex described in this paragraph, X is a targeting moiety which is a biomolecule which is a member selected from a small-molecule ligand, a peptide, a protein, an enzyme, an antibody, an antigen, a nucleic acid, a carbohydrate, a lipid and a pharmacologically active molecule. In another exemplary embodiment, in a compound or complex described in this paragraph, X is a targeting moiety which is a peptide, a protein, an enzyme or an antibody. In another exemplary embodiment, in a compound or complex described in this paragraph, X is a targeting moiety which is a nucleic acid. In another exemplary embodiment, in a compound or complex described in this paragraph, X is a targeting moiety which is a carbohydrate. In another exemplary embodiment, in a terbium or europium complex described in this paragraph, X is a targeting moiety which is a biomolecule which is a member selected from a small-molecule ligand, a peptide, a protein, an enzyme, an antibody, an antigen, a nucleic acid, a carbohydrate, a lipid and a pharmacologically active molecule. In another exemplary embodiment, in a terbium or europium complex described in this paragraph, X is a targeting moiety which is a peptide, a protein, an enzyme or an antibody. In another exemplary embodiment, in a terbium or europium complex described in this paragraph, X is a targeting moiety which is a nucleic acid. In another exemplary embodiment, in a terbium or europium complex described in this paragraph, X is a targeting moiety which is a carbohydrate.

In an exemplary embodiment, the compound comprises two functional moieties. In another exemplary embodiment, one of these functional groups is attached to $L^4$ and the other functional group is attached to a member selected from $L^1$, $L^2$ and $L^5$. In another exemplary embodiment, one of these functional groups is attached to $L^4$ and the other functional group is attached to a member selected from $L^6$, $L^7$, $L^9$ and $L^{10}$. In another exemplary embodiment, one of these functional groups is attached to $L^4$ and the other functional group is attached to a member selected from $L^3$ and $L^8$. In another exemplary embodiment, one of these functional groups is attached to $L^4$ and the other functional group is attached to a member selected from $R^6$, $R^9$, $R^{12}$ and $R^{15}$. In an exemplary embodiment, in a compound described in this paragraph, the composition further comprises a metal, thus forming a complex. In an exemplary embodiment, in a compound described in this paragraph, the metal is a lanthanide. In an exemplary embodiment, in a compound described in this paragraph, the lanthanide is a member selected from Nd, Sm, Eu, Tb, Dy and Yb. In an exemplary embodiment, in a compound described in this paragraph, the lanthanide is Tb. In an exemplary embodiment, in a compound described in this paragraph, the lanthanide is Eu. In another exemplary embodiment, in a compound or complex described in this paragraph, X is a targeting moiety which is a biomolecule. In another exemplary embodiment, in a compound or complex described in this paragraph, X is a targeting moiety which is a biomolecule which is a member selected from a small-molecule ligand, a peptide, a protein, an enzyme, an antibody, an antigen, a nucleic acid, a carbohydrate, a lipid and a pharmacologically active molecule. In another exemplary embodiment, in a compound or complex described in this paragraph, X is a targeting moiety which is a peptide, a protein, an enzyme or an antibody. In another exemplary embodiment, in a compound or complex described in this paragraph, X is a targeting moiety which is a nucleic acid. In another exemplary embodiment, in a compound or complex described in this paragraph, X is a targeting moiety which is a carbohydrate. In another exemplary embodiment, in a terbium or europium complex described in this paragraph, X is a targeting moiety which is a biomolecule which is a member selected from a small-molecule ligand, a peptide, a protein, an enzyme, an antibody, an antigen, a nucleic acid, a carbohydrate, a lipid and a pharmacologically active molecule. In another exemplary embodiment, in a terbium or europium complex described in this paragraph, X is a targeting moiety which is a peptide, a protein, an enzyme or an antibody. In another exemplary embodiment, in a terbium or europium complex described in this paragraph, X is a targeting moiety which is a nucleic acid. In another exemplary embodiment, in a terbium or europium complex described in this paragraph, X is a targeting moiety which is a carbohydrate.

In another exemplary embodiment, one of these functional groups is attached to $L^3$ and the other functional group is attached to a member selected from $L^1$, $L^2$, $L^4$ and $L^5$. In another exemplary embodiment, one of these functional groups is attached to $L^3$ and the other functional group is attached to a member selected from $L^6$, $L^7$, $L^9$ and $L^{10}$. In another exemplary embodiment, one of these functional groups is attached to $L^3$ and the other functional group is attached to $L^8$. In another exemplary embodiment, one of these functional groups is attached to $L^3$ and the other functional group is attached to a member selected from $R^6$, $R^9$, $R^{12}$ and $R^{15}$. In an exemplary embodiment, in a compound described in this paragraph, the composition further comprises a metal, thus forming a complex. In an exemplary embodiment, in a compound described in this paragraph, the metal is a lanthanide. In an exemplary embodiment, in a compound described in this paragraph, the lanthanide is a member selected from Nd, Sm, Eu, Tb, Dy and Yb. In an exemplary embodiment, in a compound described in this paragraph, the lanthanide is Tb. In an exemplary embodiment, in a compound described in this paragraph, the lanthanide is Eu. In another exemplary embodiment, in a compound or complex described in this paragraph, X is a targeting moiety which is a biomolecule. In another exemplary embodiment, in a compound or complex described in this paragraph, X is a targeting moiety which is a biomolecule which is a member selected from a small-molecule ligand, a peptide, a protein, an enzyme, an antibody, an antigen, a nucleic acid, a carbohydrate, a lipid and a pharmacologically active molecule. In another exemplary embodiment, in a compound or complex described in this paragraph, X is a targeting moiety which is a peptide, a protein, an enzyme or an antibody. In another exemplary embodiment, in a compound or complex described in this paragraph, X is a targeting moiety which is a nucleic acid. In another exemplary embodiment, in a compound or complex described in this paragraph, X is a targeting moiety which is a carbohydrate. In another exemplary embodiment, in a terbium or europium complex described in this paragraph, X is a targeting moiety which is a biomolecule which is a member selected from a small-molecule ligand, a peptide, a protein, an enzyme, an antibody, an antigen, a nucleic acid, a carbohydrate, a lipid and a pharmacologically active molecule. In another exemplary embodiment, in a terbium or europium complex described in this paragraph, X is a targeting moiety which is a peptide, a protein, an enzyme or an antibody. In another exemplary embodiment, in a terbium or europium complex described in this paragraph, X is a targeting moiety which is a nucleic acid. In another exemplary embodiment, in a terbium or europium complex described in this paragraph, X is a targeting moiety which is a carbohydrate.

In another exemplary embodiment, the compound of Formulae (III) or (IIIa) or (IV) or (IVa) or (V) or (Va) or (VI) or (VIa) or (VII) or (VIIa) or (VIII) or (VIIIa), in which X is a member selected from an amine, a carboxylic acid, a maleimidyl, a thiazolidyl, a substituted or unsubstituted NHS ester, a sulfonated NHS ester and a succinimidyl moiety. In another exemplary embodiment, the compound of Formulae (III) or (Ma) or (IV) or (IVa) or (V) or (Va) or (VI) or (VIa) or (VII) or (VIIa) or (VIII) or (VIIIa), in which $L^{11}$ is substituted or unsubstituted heteroalkylene or substituted or unsubstituted alkylene and X is a member selected from an amine, a carboxylic acid, a maleimidyl, a thiazolidyl, a substituted or unsubstituted NHS ester, a sulfonated NHS ester and a succinimidyl moiety. In another exemplary embodiment, the compound of Formulae (III) or (Ma) or (IV) or (IVa) or (V) or (Va) or (VI) or (VIa) or (VII) or (VIIa) or (VIII) or (VIIIa), $L^{11}$-X is a member selected from

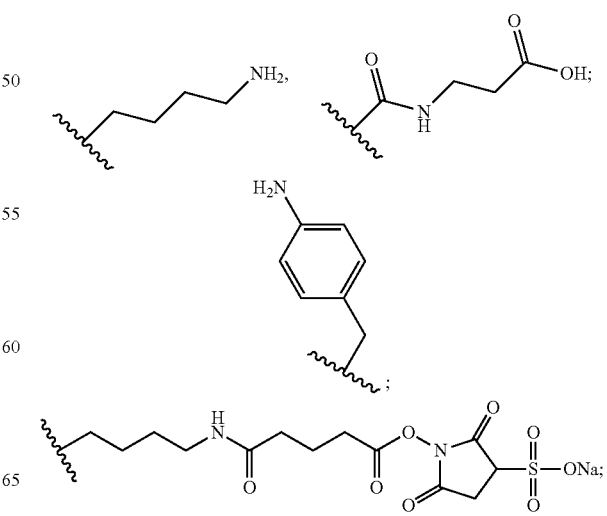

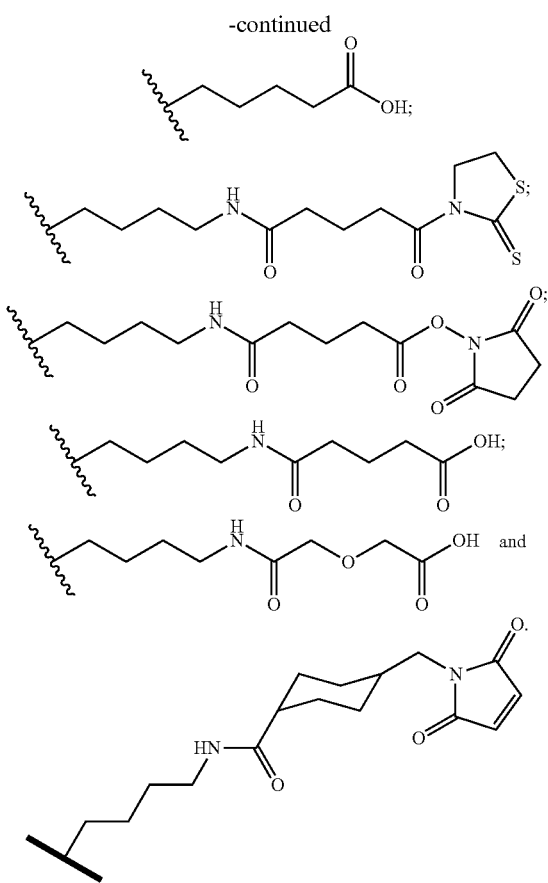

In another exemplary embodiment, in the compound of Formulae (III) or (IIIa) or (IV) or (IVa) or (V) or (Va) or (VI) or (VIa) or (VII) or (VIIa) or (VIII) or (VIIIa), $L^{11}$ is substituted or unsubstituted arylalkyl. In another exemplary embodiment, in the compound of Formulae (III) or (IIIa) or (IV) or (IVa) or (V) or (Va) or (VI) or (VIa) or (VII) or (VIIa) or (VIII) or (VIIIa), $L^{11}$ is substituted or unsubstituted arylalkyl and X is a member selected from an amine, a carboxylic acid, a maleimidyl, a thiazolidyl, a substituted or unsubstituted NHS ester, a sulfonated NHS ester and a succinimidyl moiety. In an exemplary embodiment, in a compound described in this paragraph, the composition further comprises a metal, thus forming a complex. In an exemplary embodiment, in a compound described in this paragraph, the metal is a lanthanide. In an exemplary embodiment, in a compound described in this paragraph, the lanthanide is Tb. In an exemplary embodiment, in a compound described in this paragraph, the lanthanide is Eu.

In another exemplary embodiment, the compound of Formulae (III) or (IIIa) or (IV) or (IVa) or (V) or (Va) or (VI) or (VIa) or (VII) or (VIIa) or (VIII) or (VIIIa), in which $L^{11}$ is substituted or unsubstituted heteroalkylene or substituted or unsubstituted alkylene and X is a targeting moiety which is a biomolecule. In another exemplary embodiment, the compound of Formulae (III) or (IIIa) or (IV) or (IVa) or (V) or (Va) or (VI) or (VIa) or (VII) or (VIIa) or (VIII) or (VIIIa), in which $L^{11}$ is substituted or unsubstituted $C_1$-$C_6$ alkylene and X is a targeting moiety which is a biomolecule. In another exemplary embodiment, the compound of Formulae (III) or (IIIa) or (IV) or (IVa) or (V) or (Va) or (VI) or (VIa) or (VII) or (VIIa) or (VIII) or (VIIIa), in which $L^{11}$ is substituted or unsubstituted butylene and X is a targeting moiety which is a biomolecule. In another exemplary embodiment, the compound of Formulae (III) or (IIIa) or (IV) or (IVa) or (V) or (Va) or (VI) or (VIa) or (VII) or (VIIa) or (VIII) or (VIIIa), in which $L^{11}$ is unsubstituted butylene and X is a targeting moiety which is a biomolecule. In another exemplary embodiment, in a compound described in this paragraph, the composition further comprises a metal, thus forming a complex. In an exemplary embodiment, in a compound described in this paragraph, the metal is a lanthanide. In an exemplary embodiment, in a compound described in this paragraph, the lanthanide is Tb. In an exemplary embodiment, in a compound described in this paragraph, the lanthanide is Eu. In another exemplary embodiment, in a compound or complex described in this paragraph, X is a targeting moiety which is a biomolecule which is a member selected from a small-molecule ligand, a peptide, a protein, an enzyme, an antibody, an antigen, a nucleic acid, a carbohydrate, a lipid and a pharmacologically active molecule. In another exemplary embodiment, in a compound or complex described in this paragraph, X is a targeting moiety which is a peptide, a protein, an enzyme or an antibody. In another exemplary embodiment, in a compound or complex described in this paragraph, X is a targeting moiety which is a nucleic acid. In another exemplary embodiment, in a compound or complex described in this paragraph, X is a targeting moiety which is a carbohydrate. In another exemplary embodiment, in a terbium or europium complex described in this paragraph, X is a targeting moiety which is a biomolecule which is a member selected from a small-molecule ligand, a peptide, a protein, an enzyme, an antibody, an antigen, a nucleic acid, a carbohydrate, a lipid and a pharmacologically active molecule. In another exemplary embodiment, in a terbium or europium complex described in this paragraph, X is a targeting moiety which is a peptide, a protein, an enzyme or an antibody. In another exemplary embodiment, in a terbium or europium complex described in this paragraph, X is a targeting moiety which is a nucleic acid. In another exemplary embodiment, in a terbium or europium complex described in this paragraph, X is a targeting moiety which is a carbohydrate.

In an exemplary embodiment, in the compound of Formulae (III) or (IIIa) or (IV) or (IVa) or (V) or (Va) or (VI) or (VIa) or (VII) or (VIIa) or (VIII) or (VIIIa), $L^1$, $L^2$, $L^4$ and $L^5$ are members independently selected from substituted or unsubstituted ethylene, and $L^{11}$ is substituted or unsubstituted heteroalkylene or substituted or unsubstituted alkylene and X is a targeting moiety which is a biomolecule. In another exemplary embodiment, in a compound described in this paragraph, the composition further comprises a metal, thus forming a complex. In an exemplary embodiment, in a compound described in this paragraph, the metal is a lanthanide. In an exemplary embodiment, in a compound described in this paragraph, the lanthanide is Tb. In an exemplary embodiment, in a compound described in this paragraph, the lanthanide is Eu. In another exemplary embodiment, in a compound or complex described in this paragraph, X is a targeting moiety which is a biomolecule which is a member selected from a small-molecule ligand, a peptide, a protein, an enzyme, an antibody, an antigen, a nucleic acid, a carbohydrate, a lipid and a pharmacologically active molecule. In another exemplary embodiment, in a compound or complex described in this paragraph, X is a targeting moiety which is a peptide, a protein, an enzyme or an antibody. In another exemplary embodiment, in a compound or complex described in this paragraph, X is a targeting moiety which is a nucleic acid. In another exemplary embodiment, in a compound or complex described in this paragraph, X is a targeting moiety which is a carbohydrate. In another exemplary embodiment, in a terbium or europium complex described in this paragraph, X is a targeting moiety which is a biomolecule which is a member selected from a small-molecule ligand, a peptide, a protein, an enzyme, an antibody, an antigen, a nucleic acid, a carbohydrate, a lipid and a pharmacologically active molecule. In another exemplary embodiment, in a terbium or europium complex described in this paragraph, X is a targeting moiety which is a peptide, a protein, an enzyme or an antibody. In another exemplary embodiment, in a terbium or europium complex described in this paragraph, X is a targeting moiety which is a nucleic acid. In another exemplary embodiment, in a terbium or europium complex described in this paragraph, X is a targeting moiety which is a carbohydrate.

Preferred compounds of the invention that include a functional moiety have the structure:

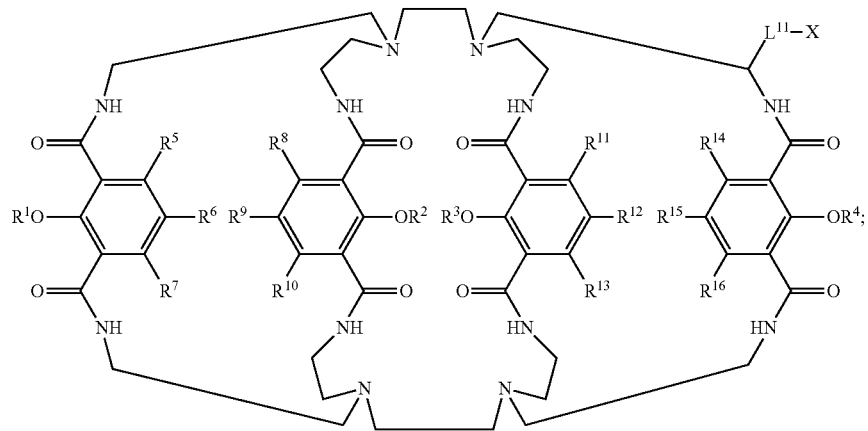

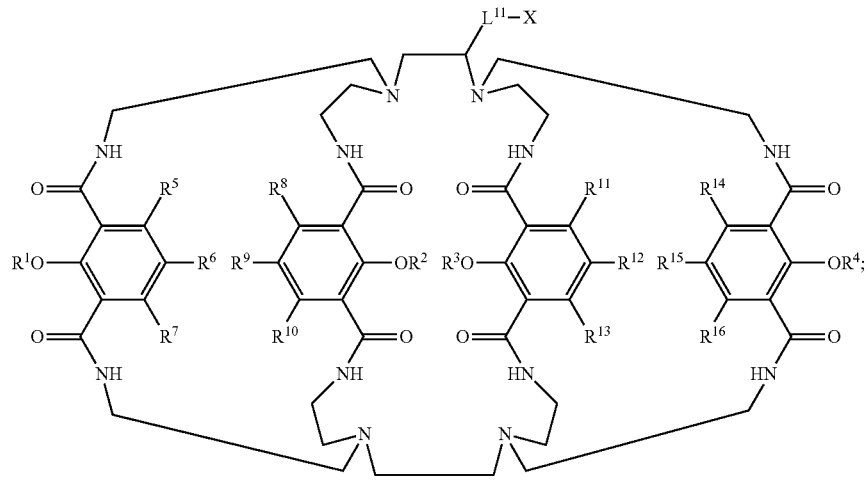

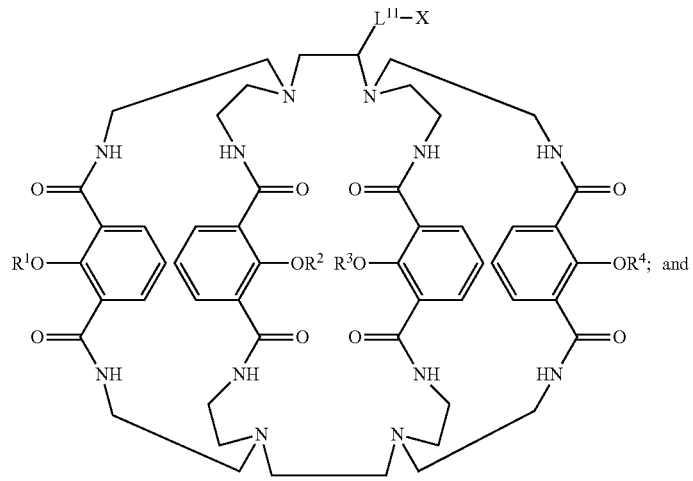

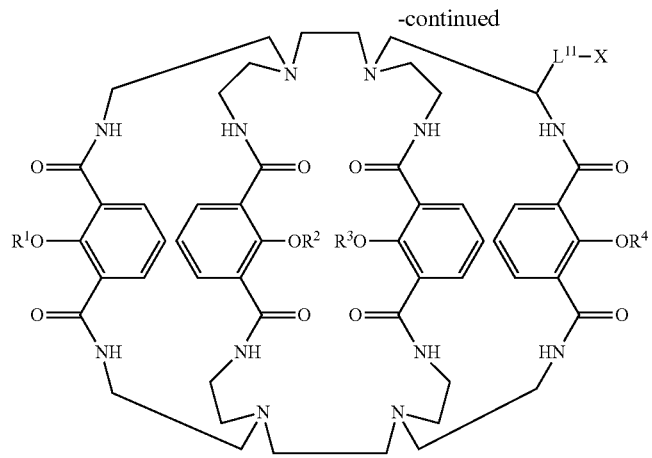

wherein $L^{11}$, X, $R^5$, $R^6$, $R^7$, $R^8$, $R^9$ $R^{10}$, $R^{11}$, $R^{12}$, $R^{13}$, $R^{14}$, $R^{15}$ and $R^{16}$ are as defined above. In an exemplary embodiment, $L^{11}$ is a member selected from substituted or unsubstituted alkyl, substituted or unsubstituted heteroalkyl and substituted or unsubstituted aryl and X is a targeting moiety which is a biomolecule. In an exemplary embodiment, $L^{11}$ is a member selected from substituted or unsubstituted heteroalkylene or substituted or unsubstituted alkylene and X is a targeting moiety which is a biomolecule which is a member selected from a small-molecule ligand, a peptide, a protein, an enzyme, an antibody, an antigen, a nucleic acid, a carbohydrate, a lipid and a pharmacologically active molecule. In an exemplary embodiment, $L^{11}$ is substituted or unsubstituted butylene and X is an antibody, an enzyme, a nucleic acid, a carbohydrate. In another exemplary embodiment, in a compound described in this paragraph, the composition further comprises a metal, thus forming a complex. In an exemplary embodiment, in a compound described in this paragraph, the metal is a lanthanide. In an exemplary embodiment, in a compound described in this paragraph, the lanthanide is Tb. In an exemplary embodiment, in a compound described in this paragraph, the lanthanide is Eu.

For instance, functionalization of compound 3 at position (aa) (FIG. 2) with a $(CH_2)_4NH_2$ group leads to the macrocyclic derivative 4:

4

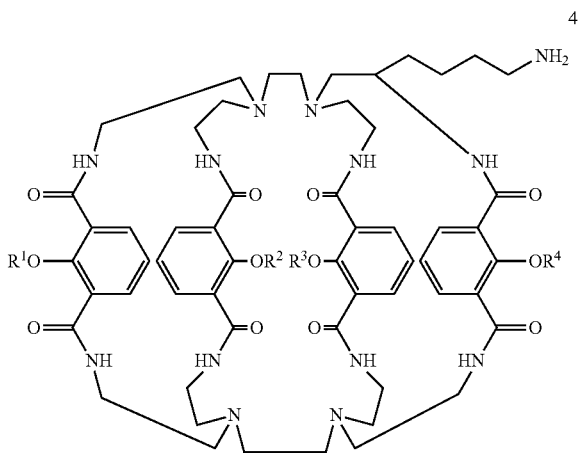

Reactive Functional Groups

In one embodiment, the functional moiety includes a reactive functional group, X, which can be used to covalently attach the complexing agent to another molecule. In another exemplary embodiment, the other molecule is a biomolecule. In another exemplary embodiment, the other molecule a small-molecule ligand, a peptide, a protein, an enzyme, an antibody, an antigen, a nucleic acid, a carbohydrate, a lipid and a pharmacologically active molecule. Alternatively, the reactive functional group can be used to link the ligand to a nano-particle of any kind.

Reactive functional groups and classes of reactions useful in attaching the compounds described herein are generally those that are well known in the art of bioconjugate chemistry. Currently favored classes of reactions available with reactive functional groups of the invention are those which proceed under relatively mild conditions. These include, but are not limited to nucleophilic substitutions (e.g., reactions of amines and alcohols with acyl halides and activated esters), electrophilic substitutions (e.g., enamine reactions) and additions to carbon-carbon and carbon-heteroatom multiple bonds (e.g., Michael reactions and Diels-Alder reactions). These and other useful reactions are discussed, for example, in: March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

a) Amines and Amino-Reactive Groups

In one embodiment, the reactive functional group is a member selected from amines, such as a primary or secondary amine, hydrazines, hydrazides, and sulfonylhydrazides. Amines can, for example, be acylated, alkylated or oxidized. Useful non-limiting examples of amino-reactive groups include N-hydroxysuccinimide (NHS) esters, sulfo-NHS esters, imidoesters, isocyanates, isothiocyanates, acylhalides, arylazides, p-nitrophenyl esters, aldehydes, sulfonyl chlorides and carboxyl groups.

NHS esters and sulfo-NHS esters react preferentially with the primary (including aromatic) amino groups of the reaction partner. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide.

Imidoesters are the most specific acylating reagents for reaction with the amine groups of e.g., a protein. At a pH between 7 and 10, imidoesters react only with primary amines Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the conjugate.

Isocyanates (and isothiocyanates) react with the primary amines of the conjugate components to form stable bonds. Their reactions with sulfhydryl, imidazole, and tyrosyl groups give relatively unstable products.

Acylazides are also used as amino-specific reagents in which nucleophilic amines of the reaction partner attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of the conjugate components, but also with its sulfhydryl and imidazole groups.

p-Nitrophenyl esters of carboxylic acids are also useful amino-reactive groups. Although the reagent specificity is not very high, α- and ε-amino groups appear to react most rapidly.

Aldehydes react with primary amines of the conjugate components (e.g., ε-amino group of lysine residues). Although unstable, Schiff bases are formed upon reaction of the protein amino groups with the aldehyde. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product. Alternatively, a stable bond may be formed by reductive amination.

Aromatic sulfonyl chlorides react with a variety of sites of the conjugate components, but reaction with the amino groups is the most important, resulting in a stable sulfonamide linkage.

Free carboxyl groups react with carbodiimides, soluble in both water and organic solvents, forming pseudoureas that can then couple to available amines yielding an amide linkage. Yamada et al., Biochemistry 1981, 20: 4836-4842, e.g., teach how to modify a protein with carbodiimides.

b) Sulfhydryl and Sulfhydryl-Reactive Groups

In another embodiment, the reactive functional group is a member selected from a sulfhydryl group (which can be converted to disulfides) and sulfhydryl-reactive groups. Useful non-limiting examples of sulfhydryl-reactive groups include maleimides, alkyl halides, acyl halides (including bromoacetamide or chloroacetamide), pyridyl disulfides, and thiophthalimides.

Maleimides react preferentially with the sulfhydryl group of the conjugate components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryl groups via disulfide exchange to give mixed disulfides. As a result, pyridyl disulfides are relatively specific sulfhydryl-reactive groups.

Thiophthalimides react with free sulfhydryl groups to also form disulfides.

c) Other Reactive Functional Groups

Other exemplary reactive functional groups include:
(a) carboxyl groups and various derivatives thereof including, but not limited to, N-hydroxybenztriazole esters, acid halides, acyl imidazoles, thioesters, p-nitrophenyl esters, alkyl, alkenyl, alkynyl and aromatic esters;
(b) hydroxyl groups, which can be converted to esters, ethers, aldehydes, etc.;
(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups, which are capable of participating in Diels-Alder reactions such as, for example, maleimido groups;
(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(f) alkenes, which can undergo, for example, cycloadditions, acylation, Michael addition, etc;
(g) epoxides, which can react with, for example, amines and hydroxyl groups;
(h) phosphoramidites and other standard functional groups useful in nucleic acid synthesis and
(i) any other functional group useful to form a covalent bond between the functionalized ligand and a molecular entity or a surface.

d) Reactive Functional Groups with Non-Specific Reactivities

In addition to the use of site-specific reactive moieties, the present invention contemplates the use of non-specific reactive functional groups to link a compound described herein to a targeting moiety. Non-specific groups include photoactivatable groups, for example. Photoactivatable groups are ideally inert in the dark and are converted to reactive species in the presence of light. In one embodiment, photoactivatable groups are selected from precursors of nitrenes generated upon heating or photolysis of azides. Electron-deficient nitrenes are extremely reactive and can react with a variety of chemical bonds including N—H, O—H, C—H, and C═C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming intraprotein crosslinks.

It is well within the abilities of a person skilled in the art to select a reactive functional group, according to the reaction partner. As an example, an activated ester, such as an NHS ester will be useful to label a protein via lysine residues. Sulfhydryl reactive groups, such as maleimides can be used to label proteins via amino acid residues carrying an SH-group (e.g., cysteine). Antibodies may be labeled by first oxidizing their carbohydrate moieties (e.g., with periodate) and reacting resulting aldehyde groups with a hydrazine containing ligand.

Additional exemplary combinations of reactive functional groups found on a compound of the invention and on a targeting moiety (or polymer or linker) are set forth in Table 2.

TABLE 2

| Chemical Functionality 1 | Chemical Functionality 2 | Linkage |
| --- | --- | --- |
| Hydroxy | Carboxy | Ester |
|  | Hydroxy | Carbonate |
|  | Amine | Carbamate |
|  | SO$_3$ | Sulfate |
|  | PO$_3$ | Phosphate |
|  | Carboxy | Acyloxyalkyl |
|  | Ketone | Ketal |
|  | Aldehyde | Acetal |
|  | Hydroxy | Anhydride |
| Mercapto | Mercapto | Disulfide |
|  | Carboxy | Acyloxyalkyl Thioether |
|  | Carboxy | Thioester |
|  | Carboxy | Amino amide |
|  | Mercapto | Thioester |
|  | Carboxy | Acyloxyalkyl ester |
|  | Carboxy | Acyloxyalkyl amide |
|  | Amino | Acyloxyalkoxy carbonyl |
|  | Carboxy | Anhydride |
|  | Carboxy | N-acylamide |
|  | Hydroxy | Ester |
|  | Hydroxy | Hydroxymethyl ketone ester |

TABLE 2-continued

| Chemical Functionality 1 | Chemical Functionality 2 | Linkage |
| --- | --- | --- |
|  | Hydroxy | Alkoxycarbonyl oxyalkyl |
| Amino | Carboxy | Acyloxyalkylamine |
|  | Carboxy | Acyloxyalkylamide |
|  | Amino | Urea |
|  | Carboxy | Amide |
|  | Carboxy | Acyloxyalkoxycarbonyl |
|  | Amide | N-Mannich base |
|  | Carboxy | Acyloxyalkyl carbamate |
| Phosphate oxygen ester | Hydroxy | Phosphate |
|  | Amine | Phosphoramidate |
|  | Mercapto | Thiophosphate ester |
| Ketone | Carboxy | Enol ester |
| Sulfonamide | Carboxy | Acyloxyalkyl sulfonamide |
|  | Ester | N-sulfonyl-imidate |

One skilled in the art will readily appreciate that many of these linkages may be produced in a variety of ways and using a variety of conditions. For the preparation of esters, see, e.g., March supra at 1157; for thioesters, see, March, supra at 362-363, 491, 720-722, 829, 941, and 1172; for carbonates, see, March, supra at 346-347; for carbamates, see, March, supra at 1156-57; for amides, see, March supra at 1152; for ureas and thioureas, see, March supra at 1174; for acetals and ketals, see, Greene et al. supra 178-210 and March supra at 1146; for acyloxyalkyl derivatives, see, PRODRUGS: TOPICAL AND OCULAR DRUG DELIVERY, K. B. Sloan, ed., Marcel Dekker, Inc., New York, 1992; for enol esters, see, March supra at 1160; for N-sulfonylimidates, see, Bundgaard et al., *J. Med. Chem.*, 31:2066 (1988); for anhydrides, see, March supra at 355-56, 636-37, 990-91, and 1154; for N-acylamides, see, March supra at 379; for N-Mannich bases, see, March supra at 800-02, and 828; for hydroxymethyl ketone esters, see, Petracek et al. *Annals NY Acad. Sci.*, 507:353-54 (1987); for disulfides, see, March supra at 1160; and for phosphonate esters and phosphonamidates.

The reactive functional groups can be chosen such that they do not participate in, or interfere with, the reactions necessary to assemble the reactive ligand analogue. Alternatively, a reactive functional group can be protected from participating in the reaction by the presence of a protecting group. Those of skill in the art will understand how to protect a particular functional group from interfering with a chosen set of reaction conditions. For examples of useful protecting groups, see Greene et al., PROTECTIVE GROUPS IN ORGANIC SYNTHESIS, John Wiley & Sons, New York, 1991.

Generally, prior to forming the linkage between the compound of the invention and the targeting (or other) agent, and optionally, the linker group, at least one of the chemical functionalities will be activated. One skilled in the art will appreciate that a variety of chemical functionalities, including hydroxy, amino, and carboxy groups, can be activated using a variety of standard methods and conditions. For example, a hydroxyl group of the ligand (or targeting agent) can be activated through treatment with phosgene to form the corresponding chloroformate, or p-nitrophenylchloroformate to form the corresponding carbonate.

In an exemplary embodiment, the invention makes use of a targeting agent that includes a carboxyl functionality. Carboxyl groups may be activated by, for example, conversion to the corresponding acyl halide or active ester. This reaction may be performed under a variety of conditions as illustrated in March, supra pp. 388-89. In an exemplary embodiment, the acyl halide is prepared through the reaction of the carboxyl-containing group with oxalyl chloride. The activated agent is combined with a ligand or ligand-linker arm combination to form a conjugate of the invention. Those of skill in the art will appreciate that the use of carboxyl-containing targeting agents is merely illustrative, and that agents having many other functional groups can be conjugated to the ligands of the invention.

Targeting Moieties

In an exemplary embodiment, the targeting moiety is a biomolecule. Exemplary targeting moieties include small-molecule ligands, lipids, linear and cyclic peptides, polypeptides (e.g., EPO, insulin etc.) and proteins, such as enzymes and receptors. Other targeting moieties include antibodies and antibody fragments (e.g., those generated to recognize small-molecules and receptor ligands), antigens, nucleic acids (e.g. RNA and cDNA), carbohydrate moieties (e.g., polysaccharides), and pharmacologically active molecules, such as toxins, pharmaceutical drugs and drugs of abuse (e.g. steroids). Additional targeting moieties are selected from solid supports and polymeric surfaces (e.g., polymeric beads and plastic sample reservoirs, such as plastic well-plates), sheets, fibers and membranes. Targeting moieties also include particles (e.g., nano-particles) and drug-delivery vehicles.

In one embodiment, the targeting moiety includes at least one unit of a macrocyclic compound. In an exemplary embodiment, the macrocyclic compound of the targeting moiety has a structure which is a compound described herein. In another exemplary embodiment, the macrocyclic compound of the targeting moiety has a structure which according to Formula (I) or (Ia) or (II) or (IIa) or (III) or (IIIa) or (IV) or (IVa) or (V) or (Va) or (VI) or (VIa) or (VII) or (VIIa) or (VIII) or (VIIIa). In another exemplary embodiment, the compound of the invention has a dendrimeric structure and encompasses several ligands having a structure according to a compound described herein. In another exemplary embodiment, the compound of the invention has a dendrimeric structure and encompasses several ligands having a structure according to Formula (I) or (Ia) or (II) or (IIa) or (III) or (IIIa) or (IV) or (IVa) or (V) or (Va) or (VI) or (VIa) or (VII) or (VIIa) or (VIII) or (VIIIa). In a further exemplary embodiment, according to this aspect, a complex based on such dendrimer includes at least two metal ions.

In one exemplary embodiment, the targeting moiety is substituted with a luminescence modifying group that allows luminescence energy transfer between a complex of the invention and the luminescence modifying group when the complex is excited.

In further embodiments, the compounds of the invention can be used in any assay format aimed at detecting a lipid in a sample (e.g., in the blood of a patient). An exemplary complex according to this embodiment, includes a targeting moiety, which is a protein containing a lipid recognition motif. Exemplary lipid binding proteins include those that bind to phosphatidylinositol, phosphatidylinositol phosphates or other biological lipids.

In another example, the targeting moiety is an antibody that recognizes and binds to an analyte. In an exemplary assay system an analyte may be detected in a sample by first incubating the sample with a complex of the invention, wherein the complex is covalently bound to an antibody that includes a binding site for the analyte. To the mixture can then be added an excess of a probe molecules that binds to the same binding site as the analyte and includes a luminescence modifying group (e.g. an acceptor). The presence and concentration of analyte in the sample is indicated by the luminescence of the assay mixture. For instance, if the concentration of analyte in the sample is high, many of the antibody binding sites will be occupied with the analyte and less binding sites will be available for the probe molecule. In an exemplary embodiment, the analyte is a lipid molecule.

In another preferred embodiment, the targeting moiety is a drug moiety. The drug moieties can be agents already accepted for clinical use or they can be drugs whose use is experimental, or whose activity or mechanism of action is under investigation. In another preferred embodiment, the targeting moiety is a drug of abuse. The drug moieties can have a proven action in a given disease state or can be only hypothesized to show desirable action in a given disease state. In a preferred embodiment, the drug moieties are compounds which are being screened for their ability to interact with an analyte of choice. As such, drug moieties which are useful as targeting moieties in the instant invention include drugs from a broad range of drug classes having a variety of pharmacological activities.

Classes of useful agents include, for example, non-steroidal anti-inflammatory drugs (NSAIDS). The NSAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniramine, triprolidine); antitussive drugs (e.g., dextromethorphan, codeine, carmiphen and carbetapentane); antipruritic drugs (e.g., methidilizine and trimeprizine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyraminde, quinidine, encamide); .beta.-adrenergic blocker drugs (e.g., metoprolol, acebutolol, betaxolol, labetalol and timolol); cardiotonic drugs (e.g., milrinone, aminone and dobutamine); antihypertensive drugs (e.g., enalapril, clonidine, hydralazine, minoxidil, guanadrel, guanethidine); diuretic drugs (e.g., amiloride and hydrochlorothiazide); vasodilator drugs (e.g., diltazem, amiodarone, isosuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chlorprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazapam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of .beta.-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole, pentamidine, gentamycin, kanamycin, lineomycin, methacycline, methenamine, minocycline, neomycin, netilmycin, paromomycin, streptomycin, tobramycin, miconazole and amanfadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, .alpha.-2-interferon) anti-estrogens (e.g., tamoxifen), antimetabolites (e.g., fluorouracil, methotrexate, mercaptopurine, thioguanine).

The targeting moiety can also comprise hormones (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, dephenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progenstogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful targeting moieties include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine $H_2$ antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

The above enumerated, and other molecules, can be attached to the compounds of the invention, to solid substrates and the like by methods well-known to those of skill in the art. Ample guidance can be found in literature devoted to, for example, the fields of bioconjugate chemistry and drug delivery. For example, one of skill, faced with a drug comprising an available amine will be able to choose from among a variety of amine derivatizing reactions, locate an appropriately functionalized partner (e.g., a carboxylic acid terminated thiol) for the organic layer and react the partners under conditions chosen to effect the desired coupling (e.g., dehydrating agents, e.g., dicyclohexylcarbodiimide). See, for example, MODIFICATION OF PROTEINS: FOOD, NUTRITIONAL, AND PHARMACOLOGICAL ASPECTS, Feeney et al., Eds., American Chemical Society, Washington, D.C., 1982, pp. 370-387; POLYMERIC DRUGS AND DRUG DELIVERY SYSTEMS, Dunn et al., Eds., American Chemical Society, Washington, D.C., 1991.

Linker $L^{11}$

In one preferred embodiment, the linker $L^{11}$ of the functional moiety is long enough to avoid side reactions during synthesis (e.g. intra-molecular reactions, such as intra-molecular peptide bond formation), to allow coupling of the compound or complex of the invention to a targeting moiety and to allow the targeting moiety to fulfill its intended function. Useful linkers include those with about 2 to about 50 linear atoms, preferably about 4 to about 20 linear atoms.

In another exemplary embodiment, the linker moiety $L^{11}$ or the targeting moiety include a polyether, such as polyethylene glycol (PEG) and derivatives thereof. In one example, the polyether has a molecular weight between about 50 to about 10,000 daltons.

Exemplary Compounds

Exemplary compounds of the invention include:

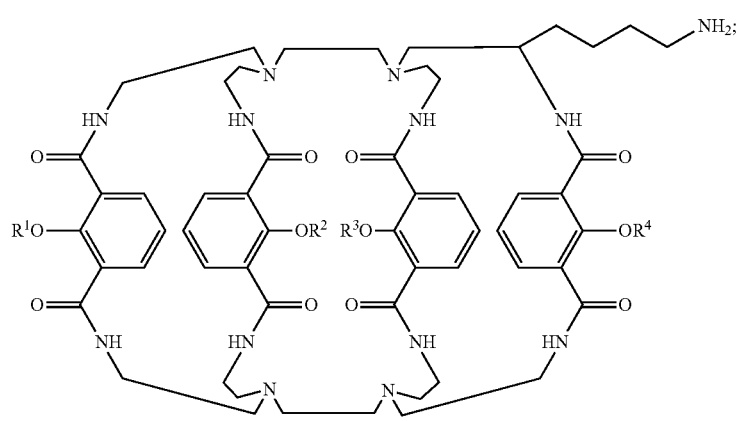

4

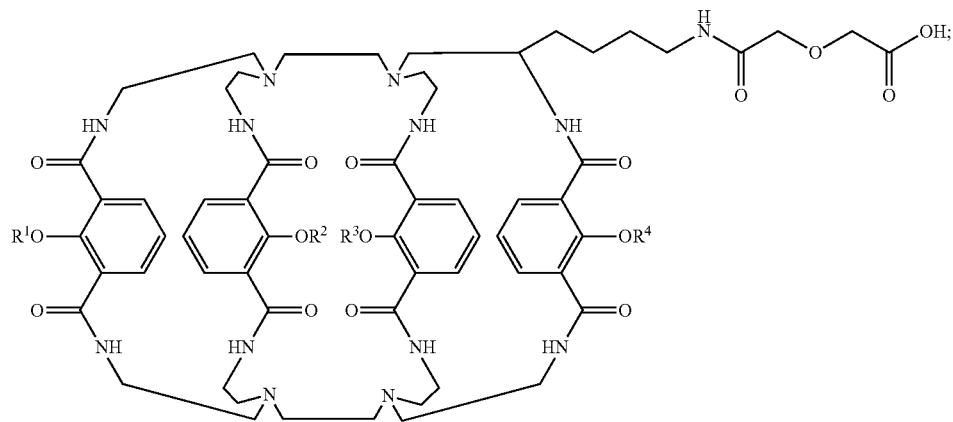
5
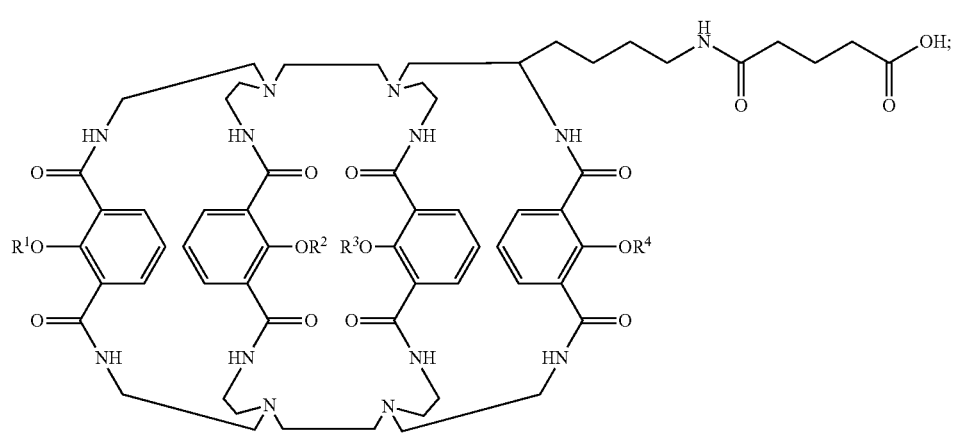
5a
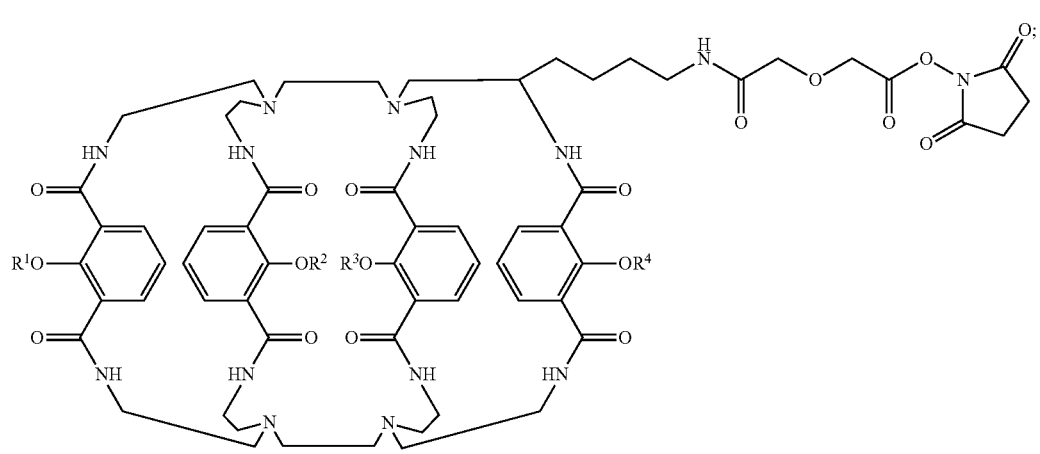
6

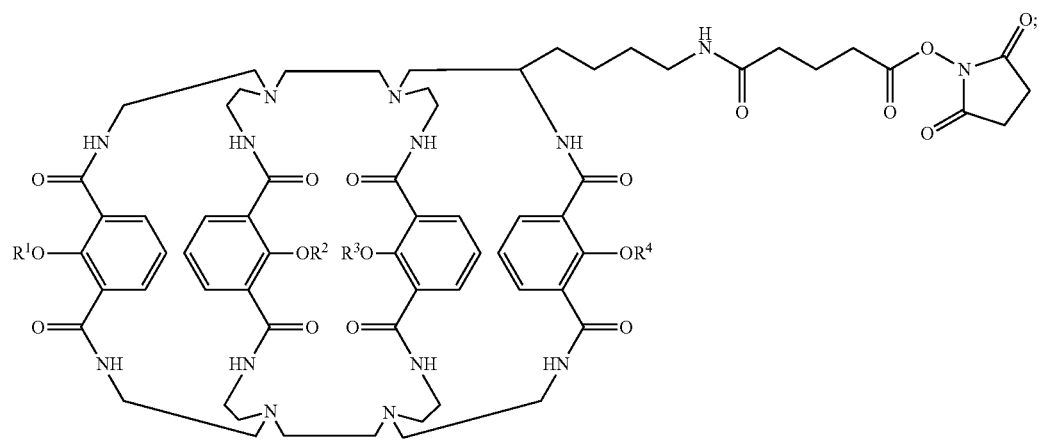
6a
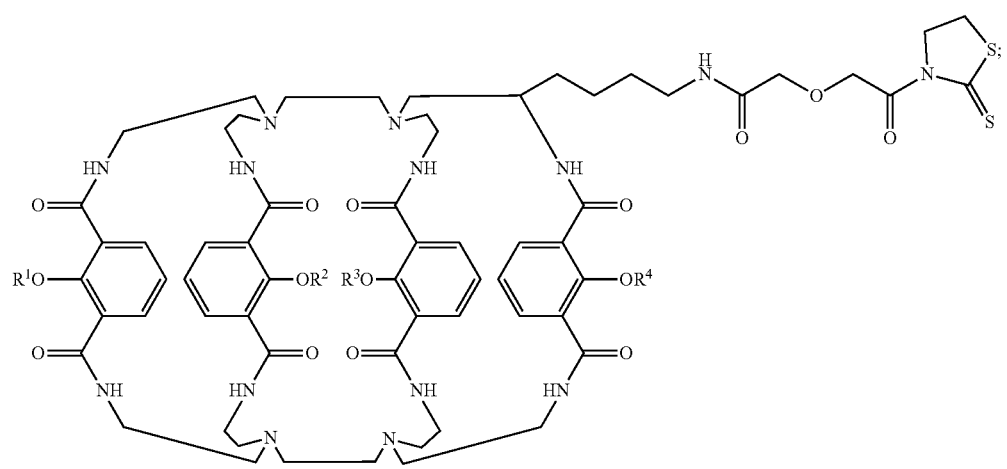
7
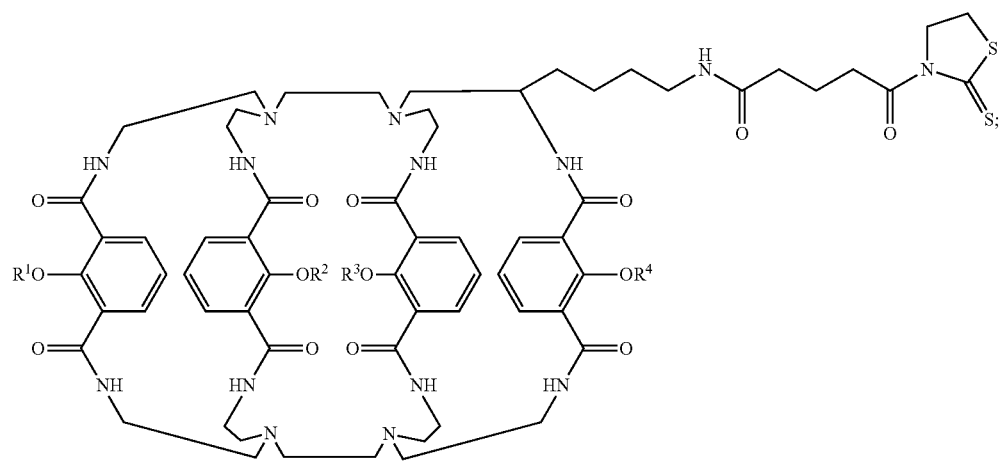
7a

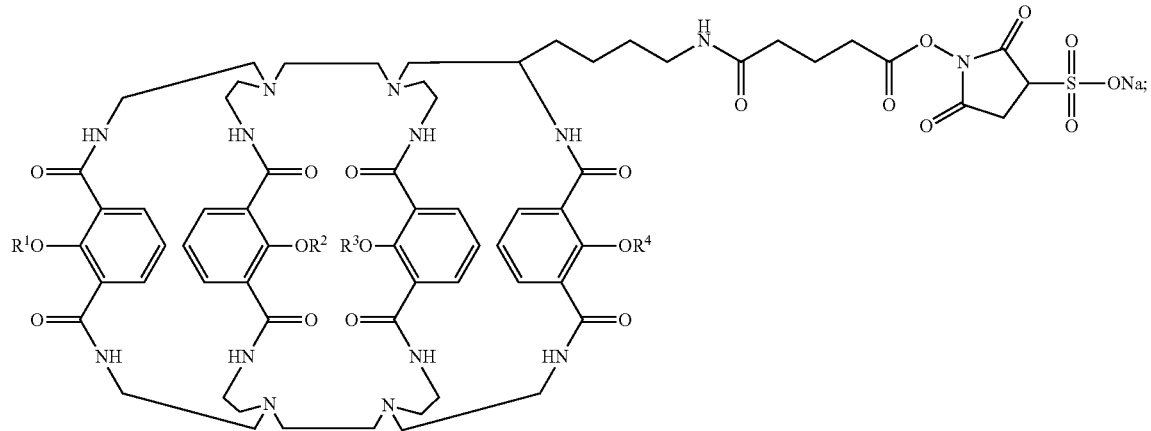
8
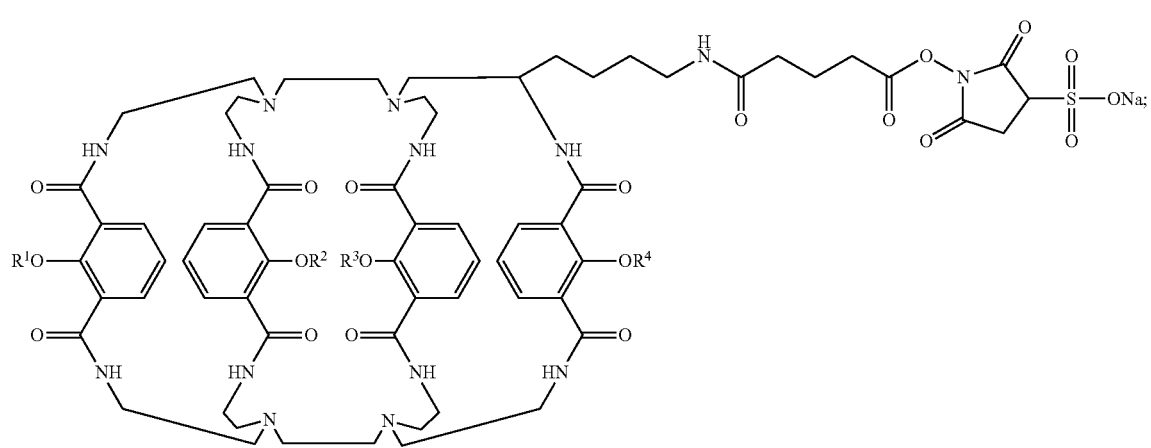
8a
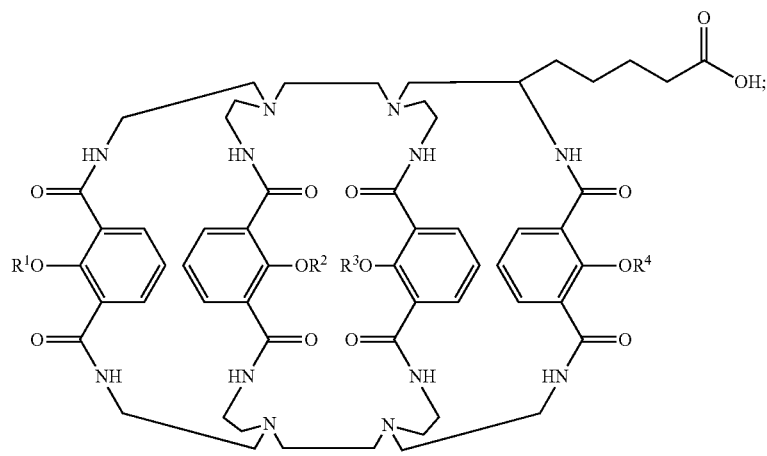
9

-continued
10
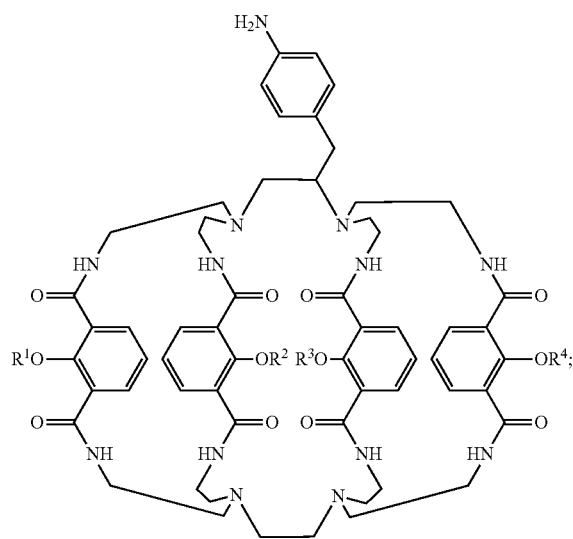
11
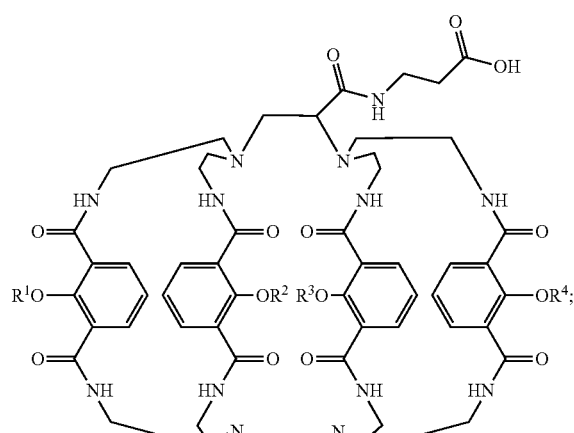
11a
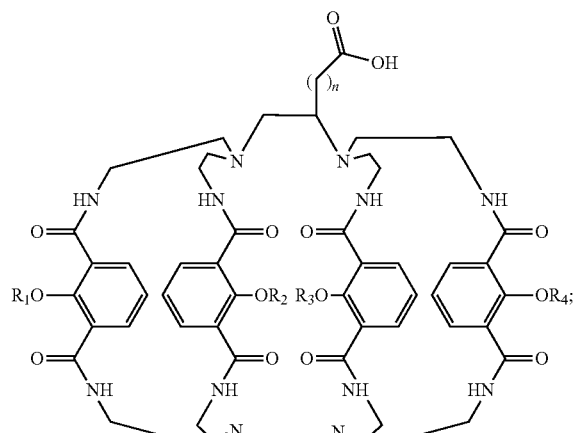
11b
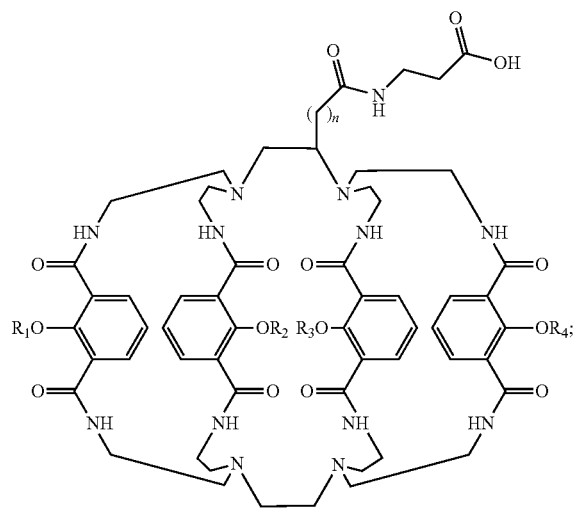
12
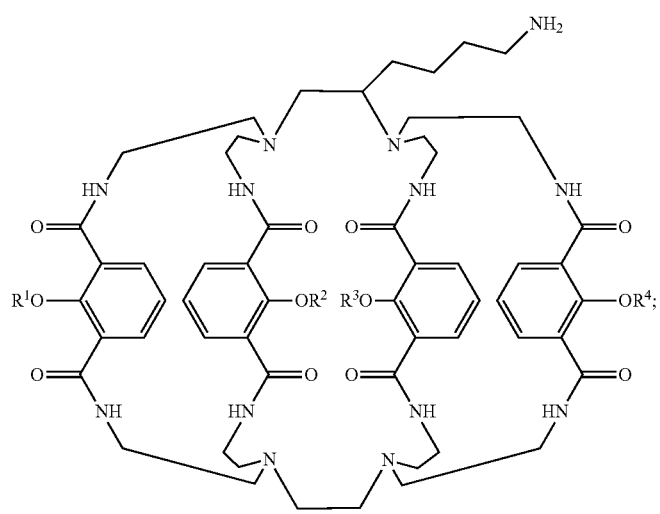

wherein $R^1$, $R^2$, $R^3$ and $R^4$ are as defined above. In an exemplary embodiment, one of these exemplary compounds is chelated to a metal, thus forming a complex. In an exemplary embodiment, in a compound described in this paragraph, the metal is a lanthanide. In an exemplary embodiment, the lanthanide is a member selected from Nd, Sm, Eu, Tb, Dy and Yb. In an exemplary embodiment, the lanthanide is Tb. In an exemplary embodiment, in a compound described in this paragraph, the lanthanide is Eu. In an exemplary embodiment, the compound is 4 and the lanthanide is a member selected from Nd, Sm, Eu, Tb, Dy and Yb. In an exemplary embodiment, the compound is 4 and the lanthanide is Tb. In an exemplary embodiment, the compound is 4 and the lanthanide is Eu. In an exemplary embodiment, the compound is 5a and the lanthanide is a member selected from Nd, Sm, Eu, Tb, Dy and Yb. In an exemplary embodiment, the compound is 5a and the lanthanide is Tb. In an exemplary embodiment, the compound is 5a and the lanthanide is Eu.

Synthesis

The compounds and complexes of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to limit the scope of reactions or reaction sequences that are useful in preparing the compounds of the present invention.

The compounds of the invention can be prepared as a single stereoisomer or as a mixture of stereoisomers. In a preferred embodiment, the compounds are prepared as substantially a single isomer. Isomerically pure compounds are prepared by using synthetic intermediates that are isomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose an appropriate method for a particular situation. See, generally, Furniss et al. (eds.) VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

In one embodiment, the compounds of the invention are synthesized by reacting a cap molecule with appropriate building blocks, such as hydroxy isophthalic acid. The resulting intermediate is then reacted with a second cap molecule, preferentially containing a functional moiety. An exemplary synthetic route is outlined in the Examples section.

Attachment at (aa) in FIG. 2

The syntheses of exemplary cap molecules, containing a functional group, are outlined below. Compound 13 can be prepared by following the synthetic route presented in Scheme 1. Compound 13 can then be transformed into compound 9, using the synthetic approach outlined in Examples 4, 5, 6 and 7.

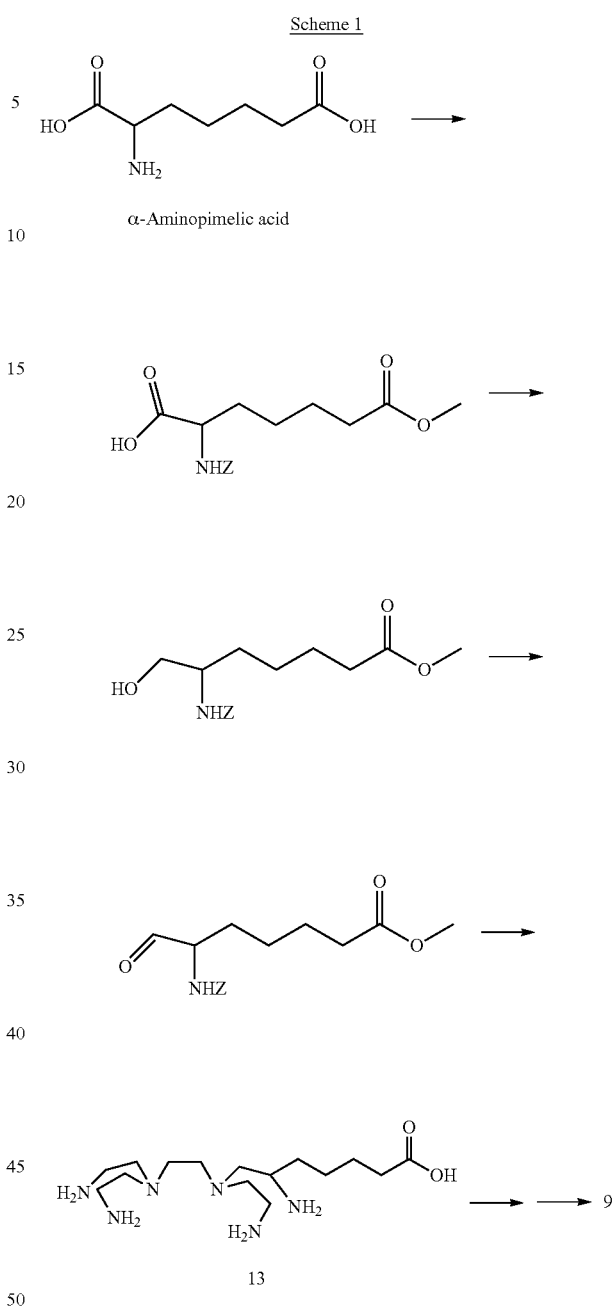

Multiple functional groups can be attached according to the exemplary description provided in the following scheme. Other methods of attaching different functional groups can occur according to methods known to one of skill in the art.

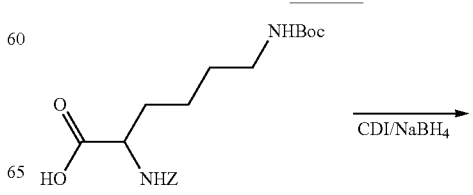

59
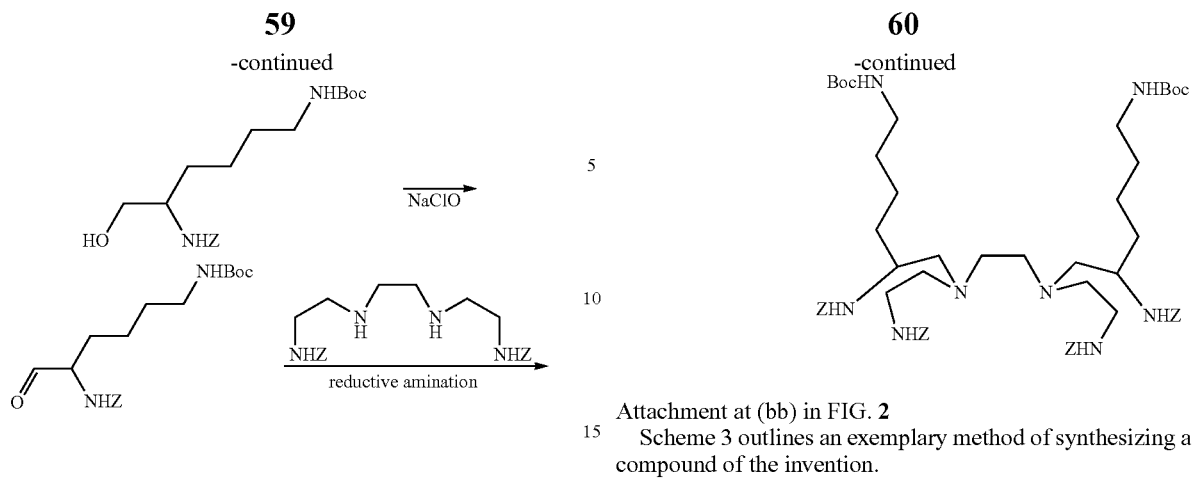
Attachment at (bb) in FIG. 2
Scheme 3 outlines an exemplary method of synthesizing a compound of the invention.
Scheme 3
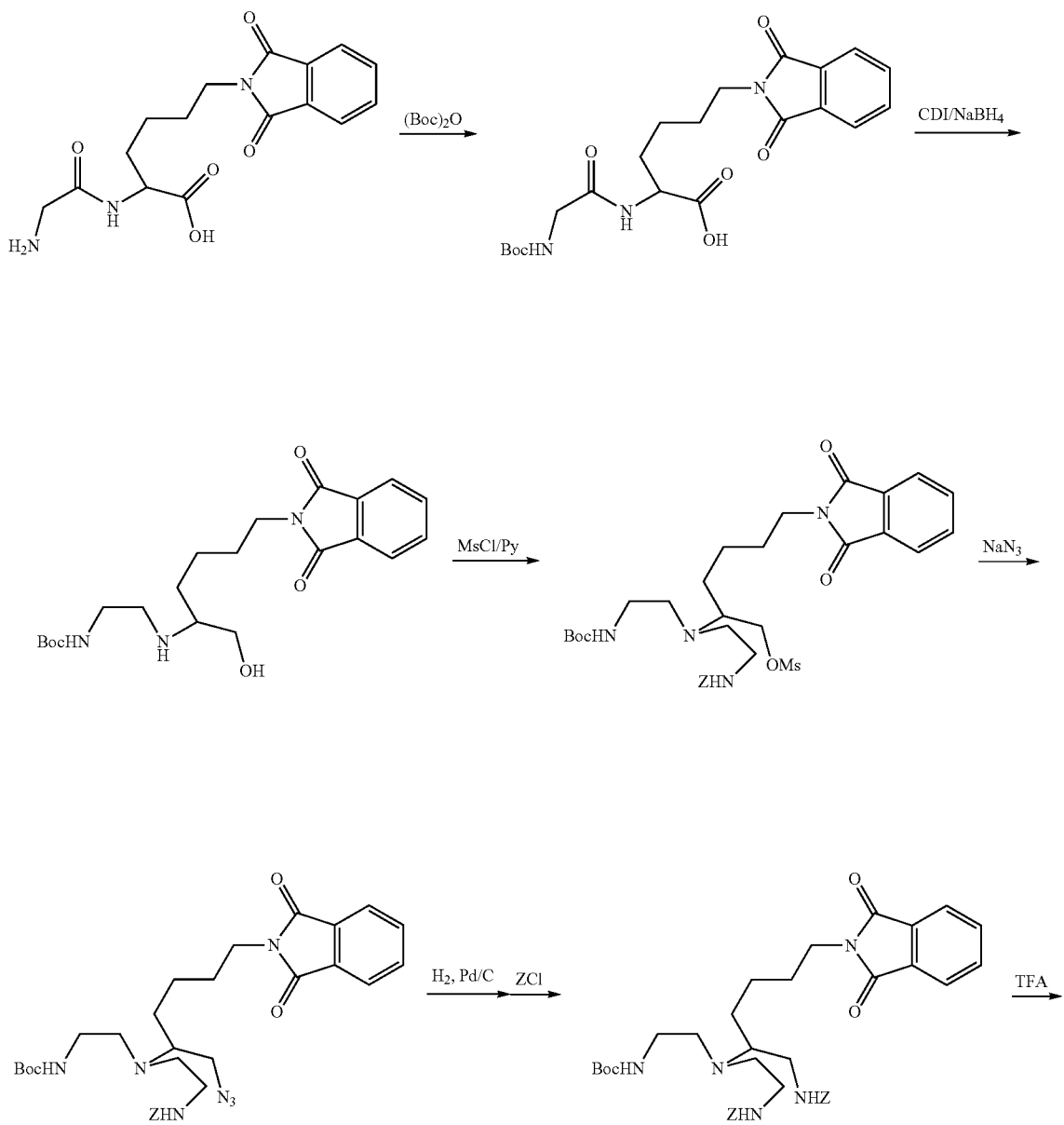

61  62
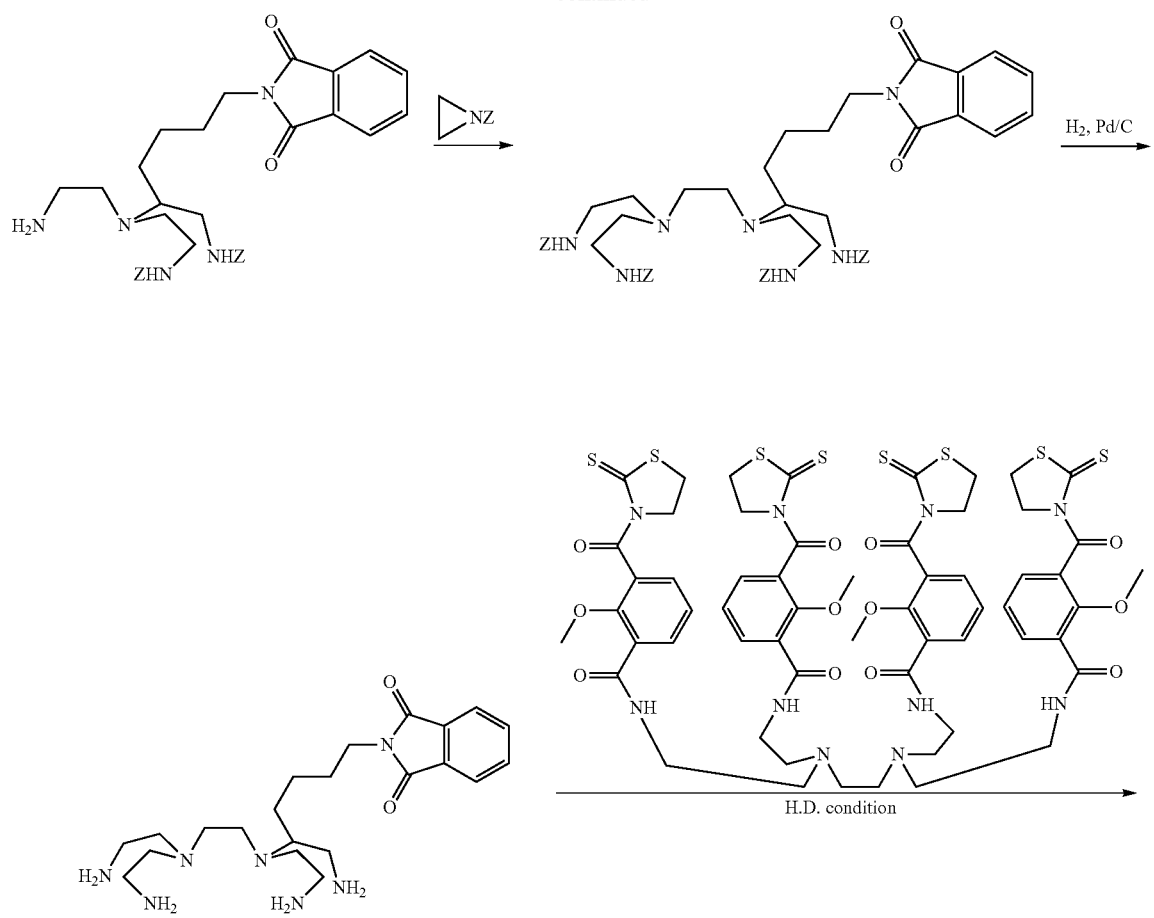
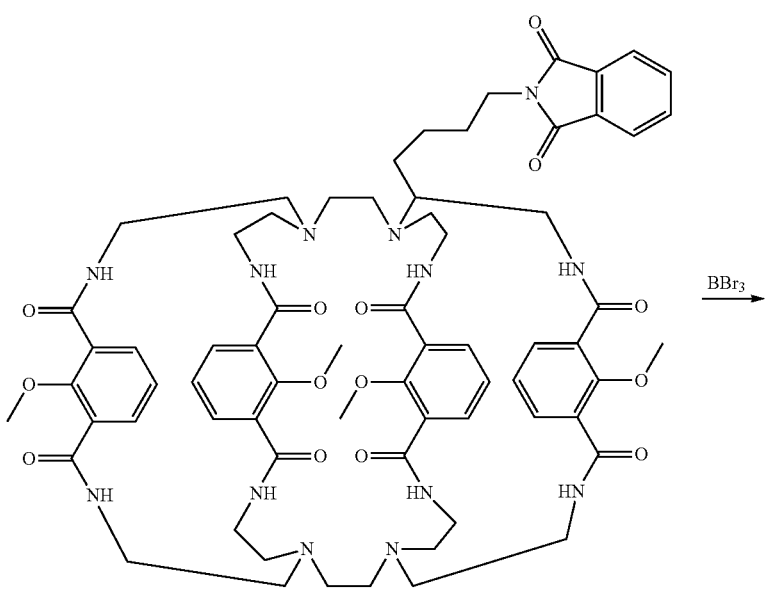

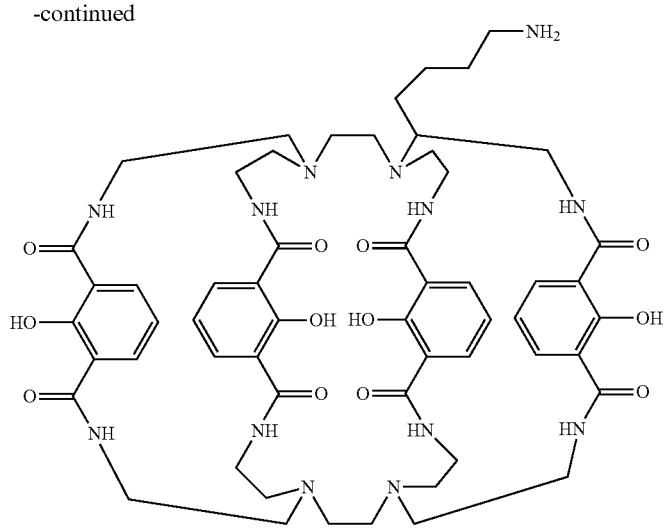
Attachment at (cc) in FIG. 2
Scheme 4 outlines an exemplary method of synthesizing compound 11.
Scheme 5 outlines an exemplary method of synthesizing compound 10.
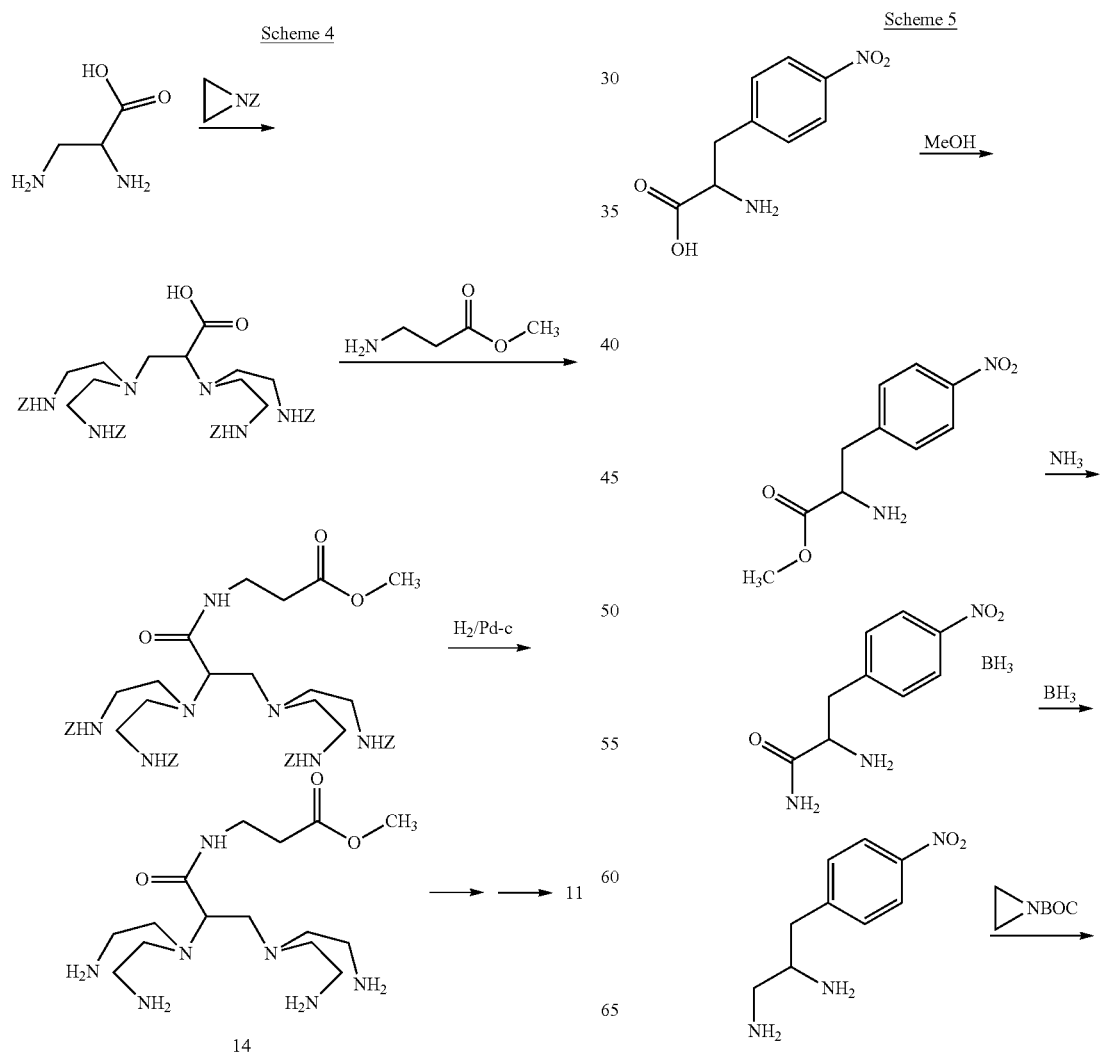

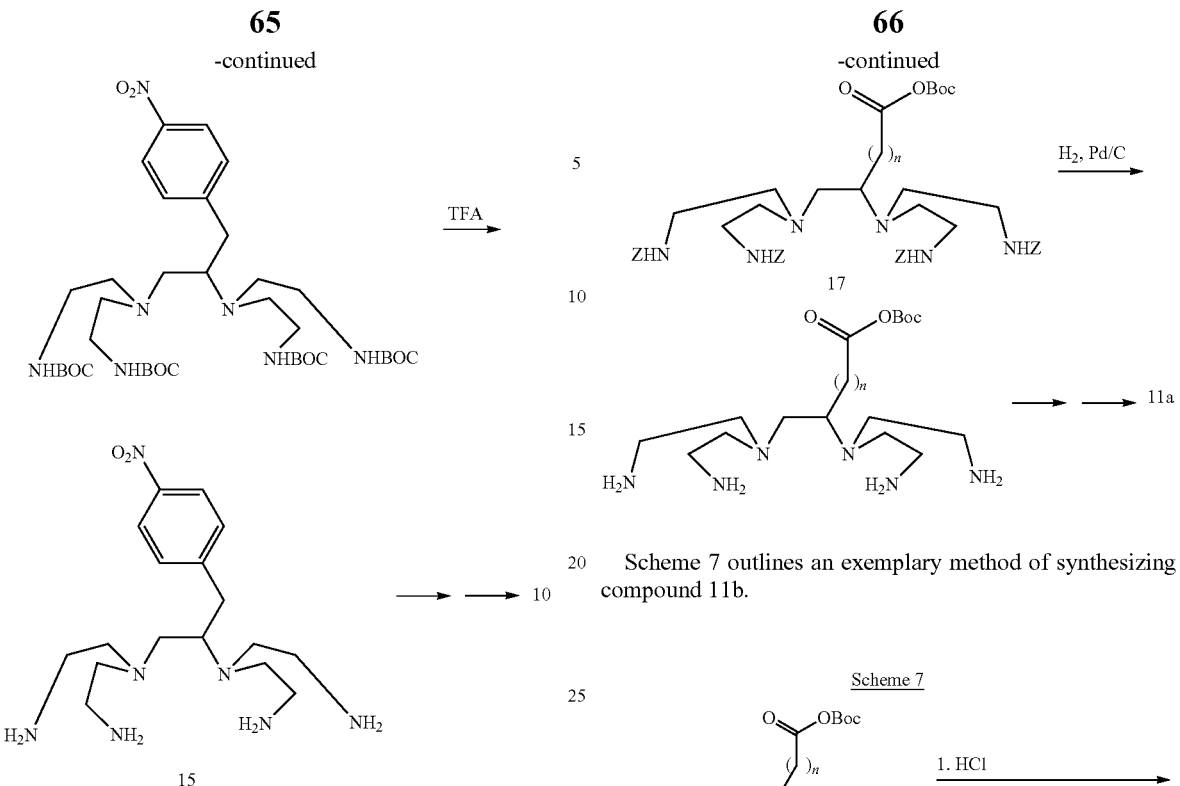

Compound 15 can be prepared using the procedure outlined in Scheme 5. Subsequently, 15 can be transformed into compound 10, using the synthetic steps described in Examples 4, 5, 6 and 7 in addition to a synthetic step useful for the reduction of the nitro group.

Scheme 6 outlines an exemplary method of synthesizing compound 11a.

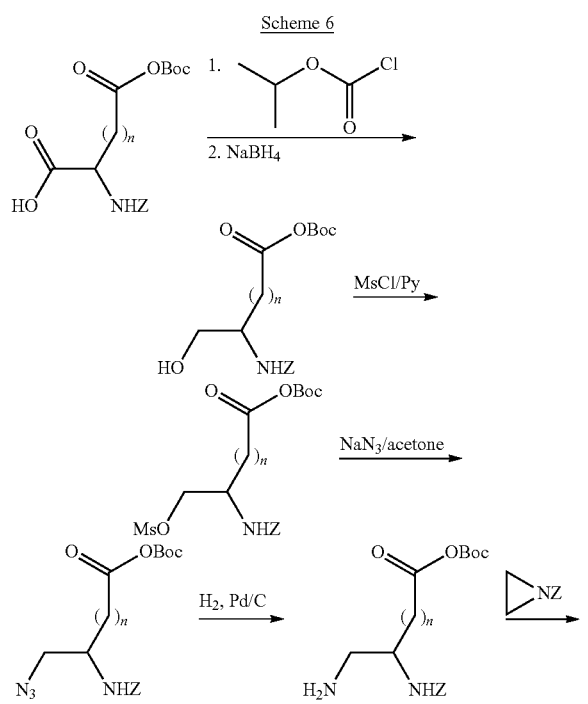

Scheme 7 outlines an exemplary method of synthesizing compound 11b.

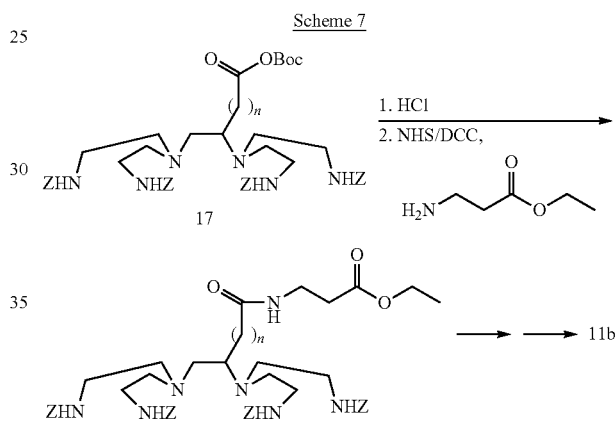

Scheme 8 outlines an exemplary method of synthesizing compound 12.

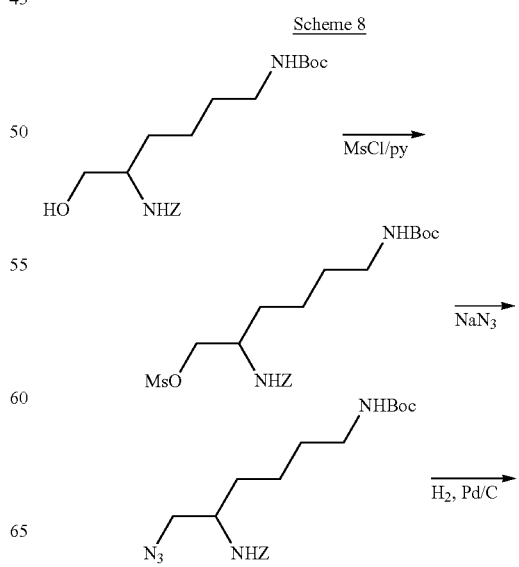

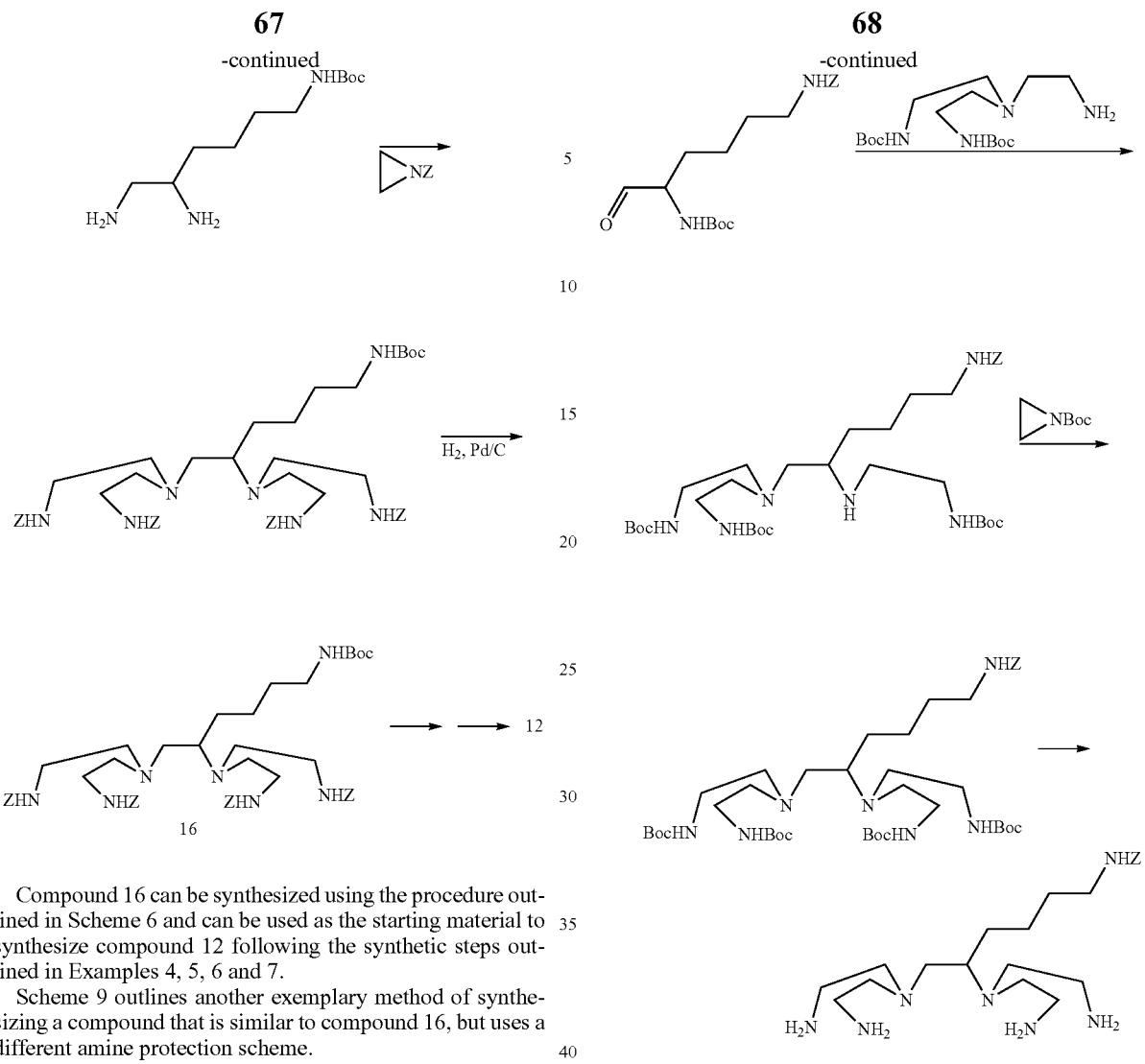

Compound 16 can be synthesized using the procedure outlined in Scheme 6 and can be used as the starting material to synthesize compound 12 following the synthetic steps outlined in Examples 4, 5, 6 and 7.

Scheme 9 outlines another exemplary method of synthesizing a compound that is similar to compound 16, but uses a different amine protection scheme.

Scheme 9

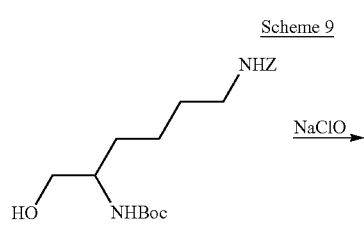

Attachment at (dd) in FIG. 2

Scheme 10 outlines an exemplary method of synthesizing a compound with a functional moiety attached to the (dd) position. While this scheme displays the synthesis of a complexing agent with a functional moiety at both the (cc) and (dd) positions, a complexing agent with a single functional moiety at the (dd) position (or an additional functional moiety at another position) can be synthesized by utilizing one or more of the syntheses described herein.

Scheme 10

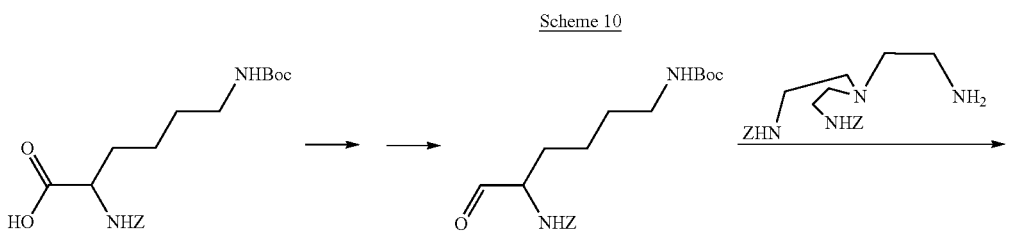

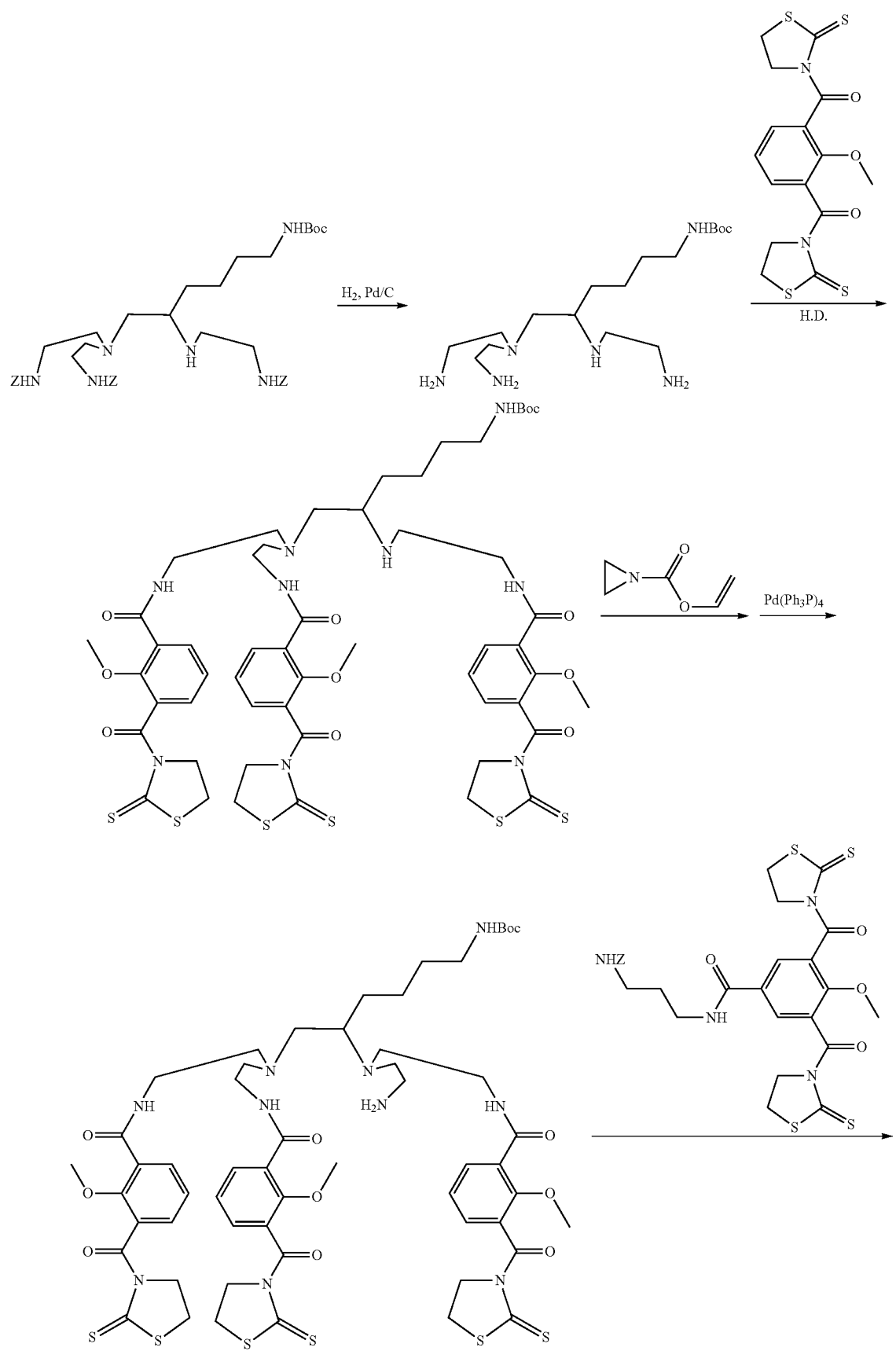

71
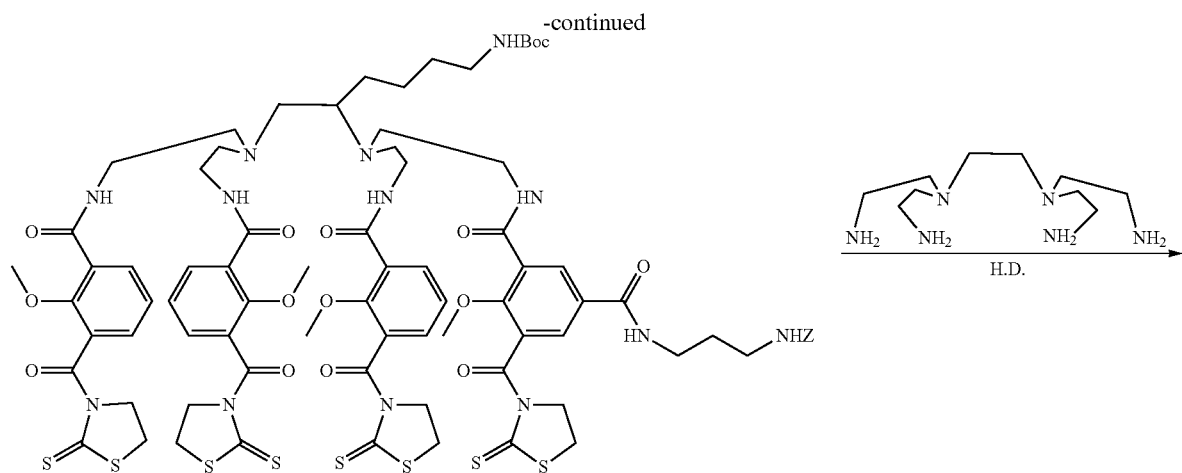
72
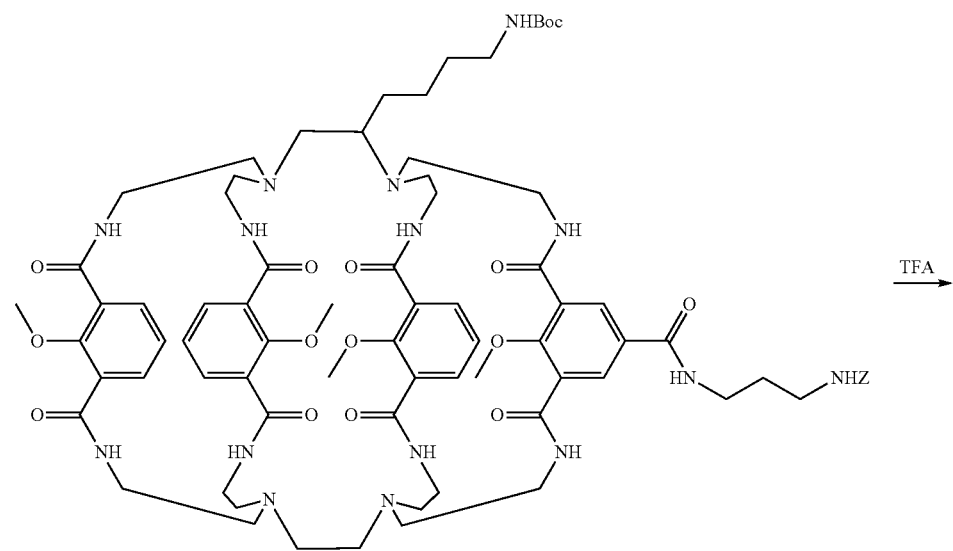
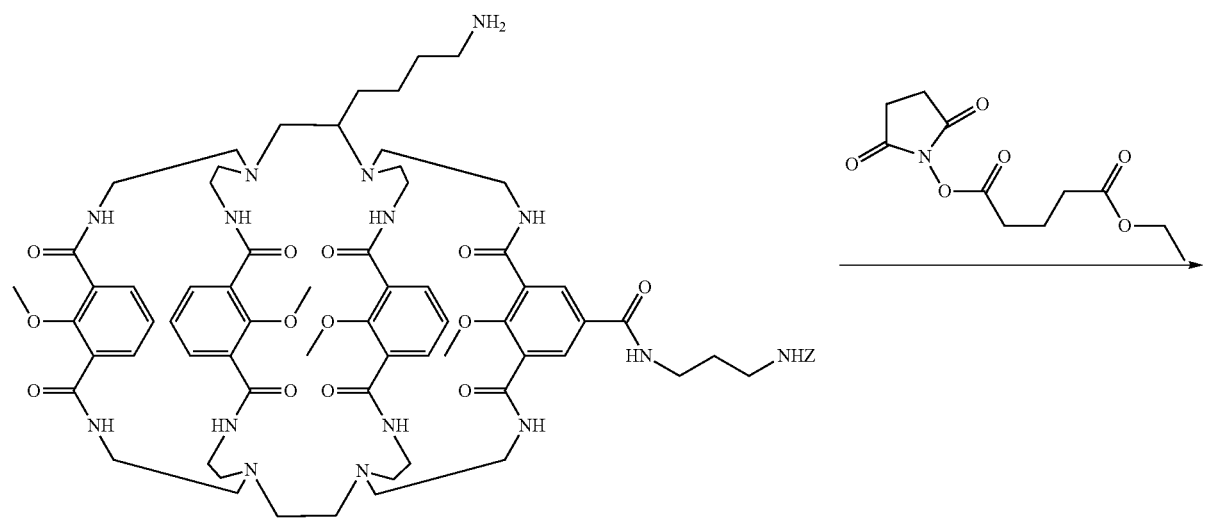

-continued
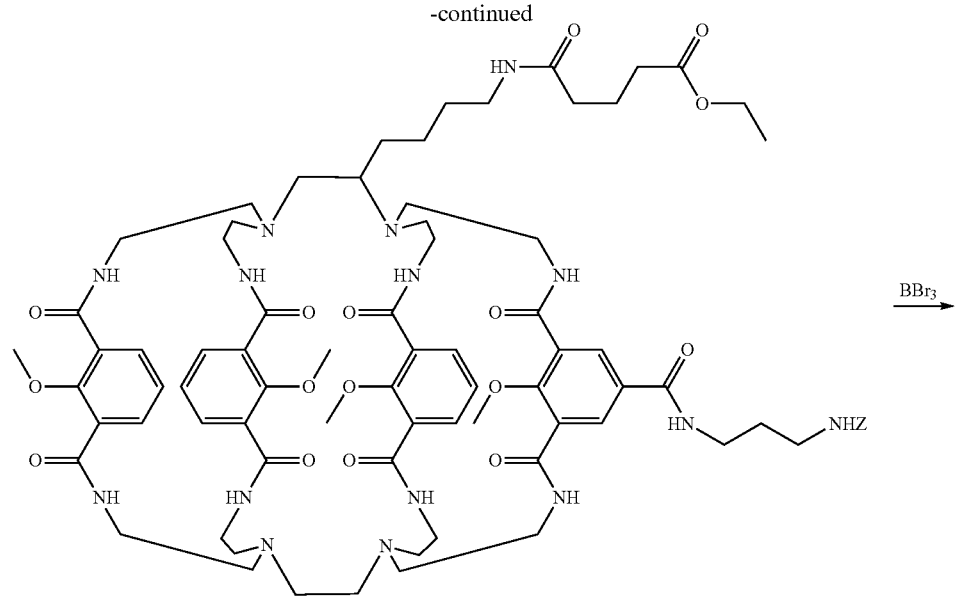
BBr₃ →
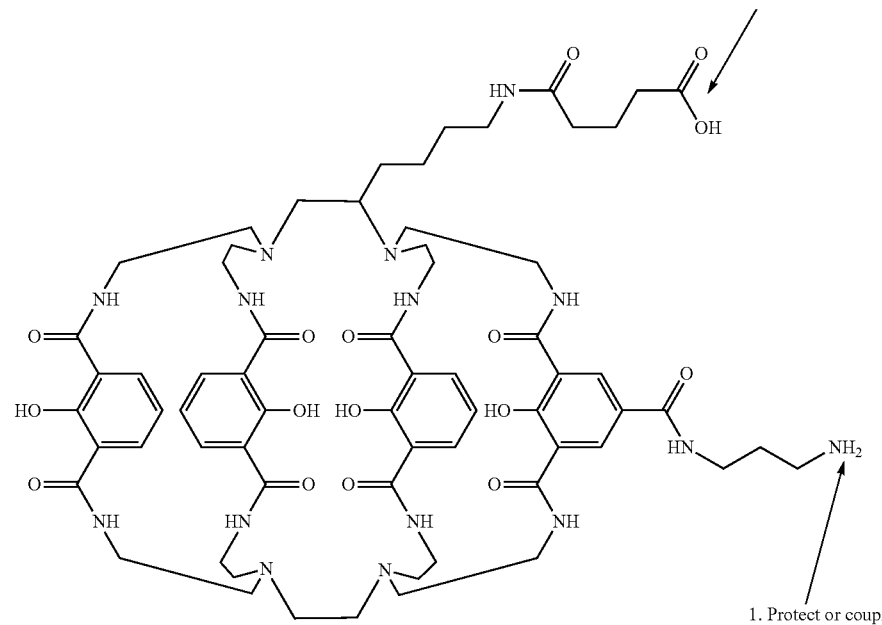
2. Protect or Activate and couple
1. Protect or couple Attachment at (ee) in FIG. 2

Scheme 11 outlines an exemplary method of synthesizing a compound with a functional moiety attached to the (ee) position. While this scheme displays the synthesis of a complexing agent with a functional moiety at both the (cc) and (ee) positions, a complexing agent with a single functional moiety at the (ee) position (or an additional functional moiety at another position) can be synthesized by utilizing one or more of the syntheses described herein.

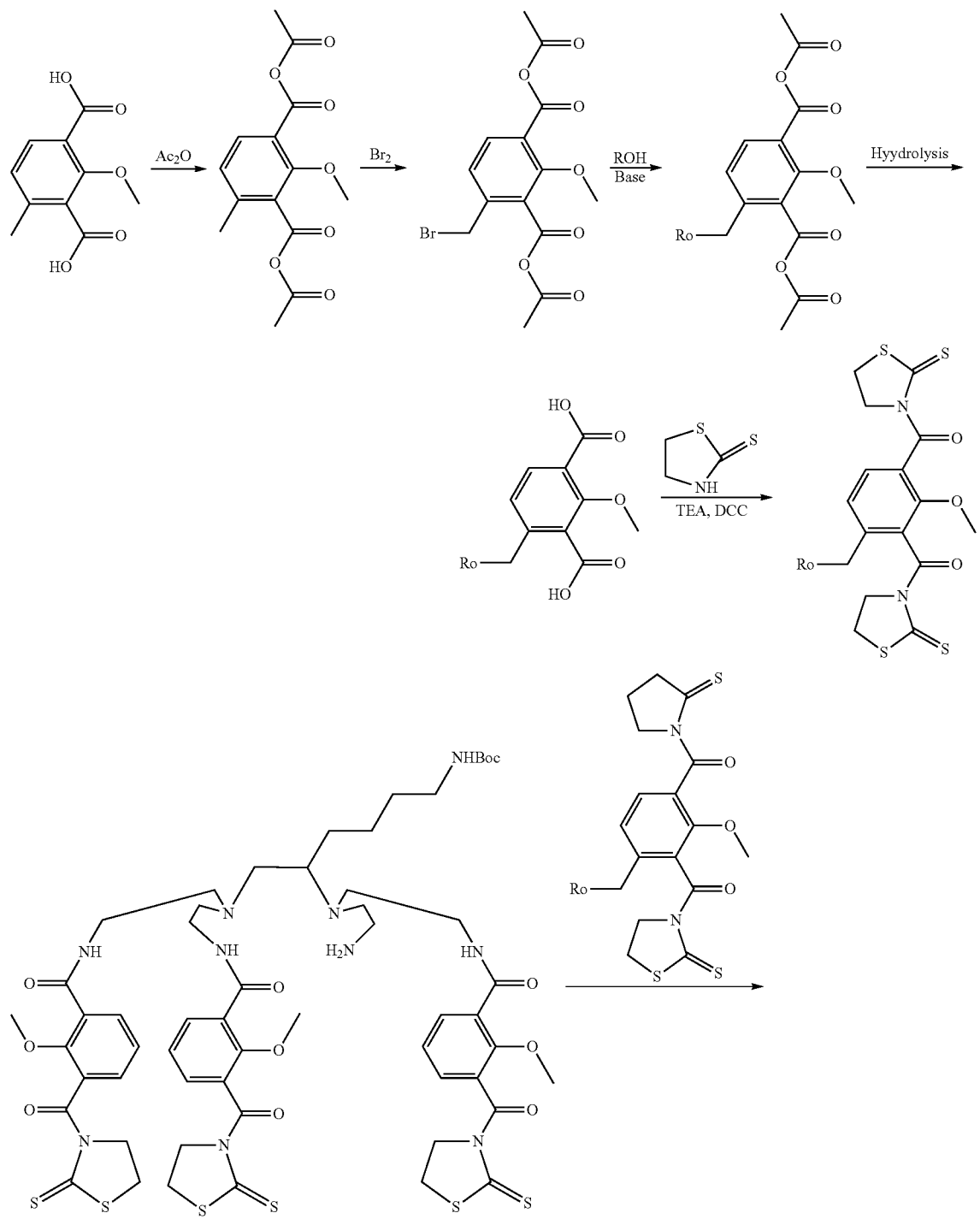

Scheme 11

77 78
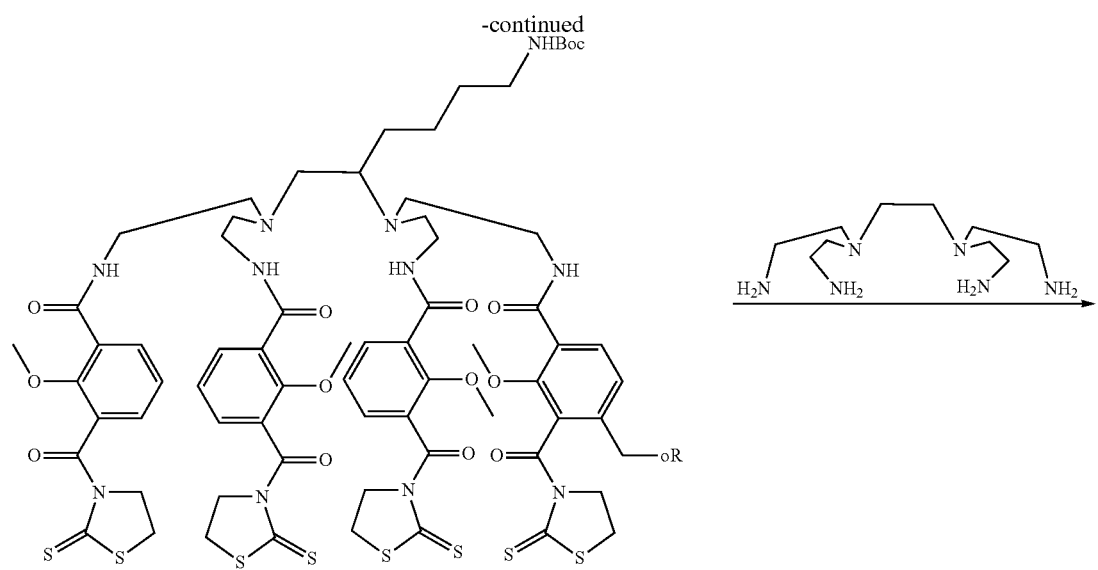
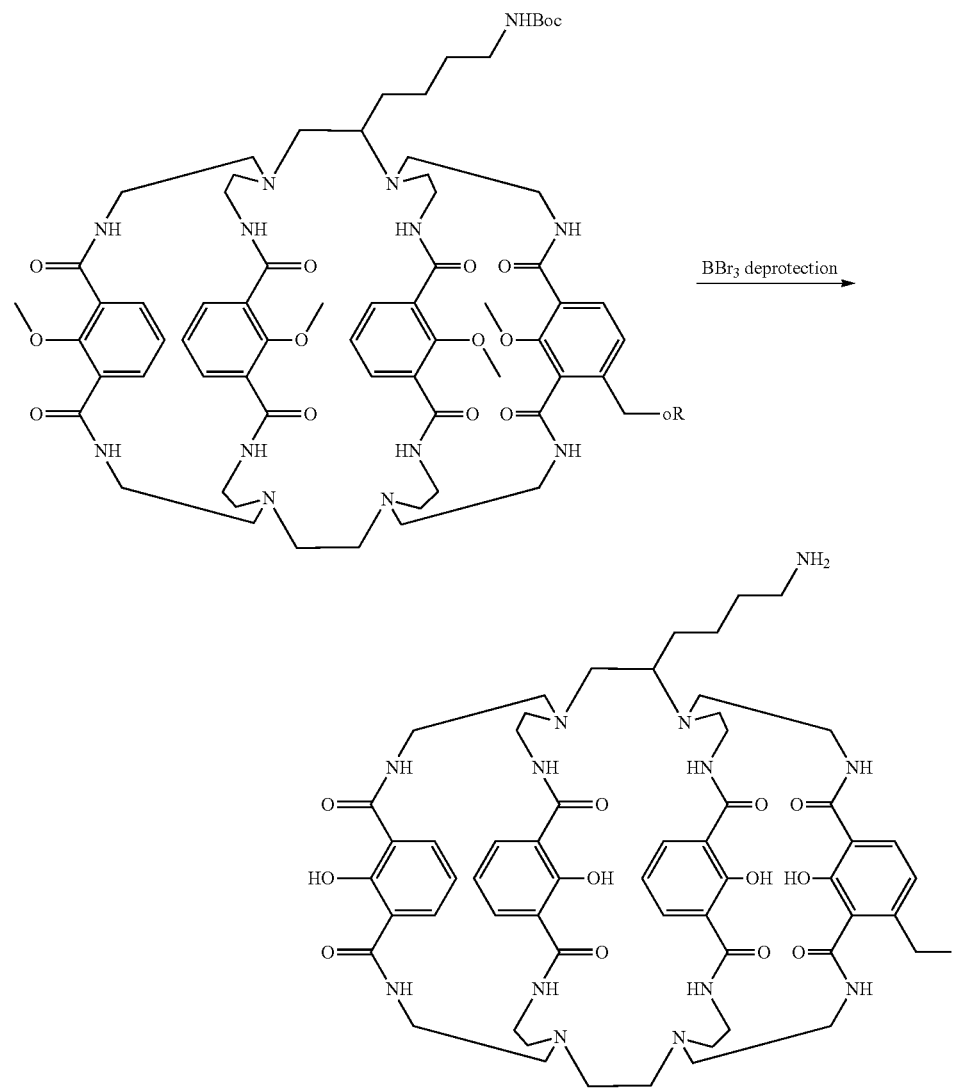

Additional examples for the synthesis of these molecules can be found in the Examples section.

Once the complexing agent is formed and purified, the metal complex is synthesized by any of a wide range of art-recognized methods, including, for example, by incubating a salt of the ligand with a metal salt, such as a lanthanide salt (e.g., lanthanide trihalide, lanthanide triacetate). The reaction of the complexing agent with the metal ion is carried out either before or after coupling the complexing agent to a targeting moiety in order to generate a complex of the invention.

Attaching a First Cap Moiety

Scheme 12 outlines an exemplary method of synthesizing a cap molecule attached to a phthalamidyl moiety.

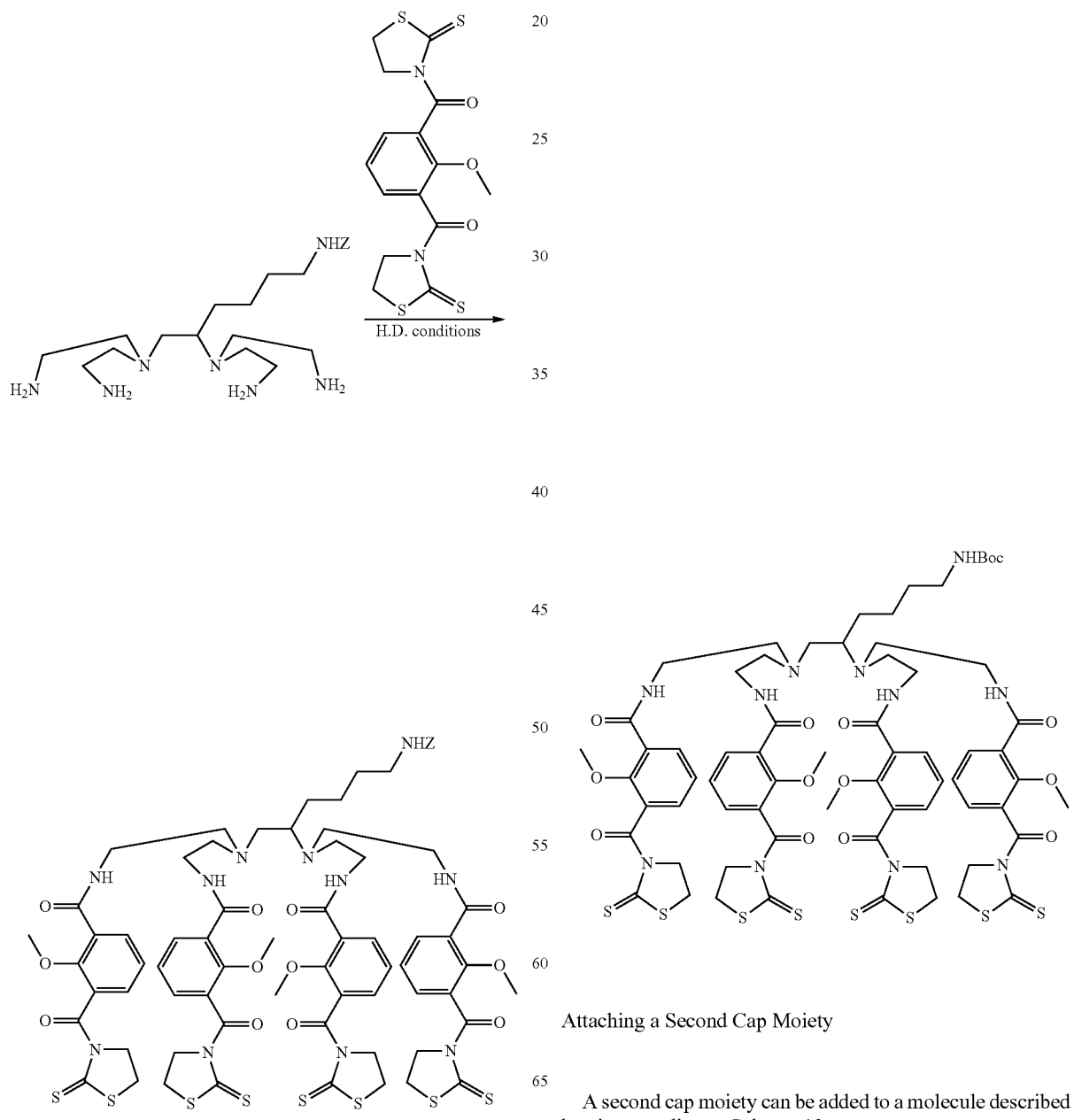

Attaching a Second Cap Moiety

A second cap moiety can be added to a molecule described herein according to Scheme 13.

Scheme 13
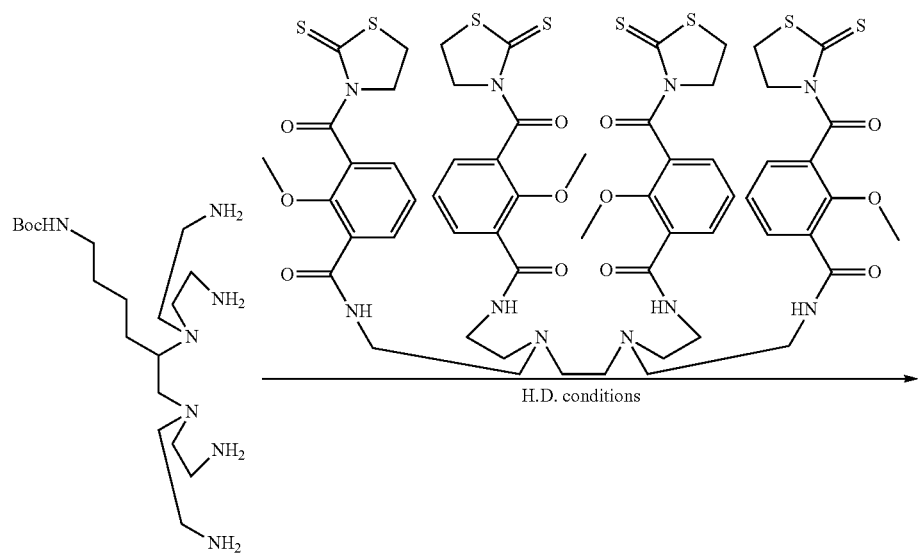
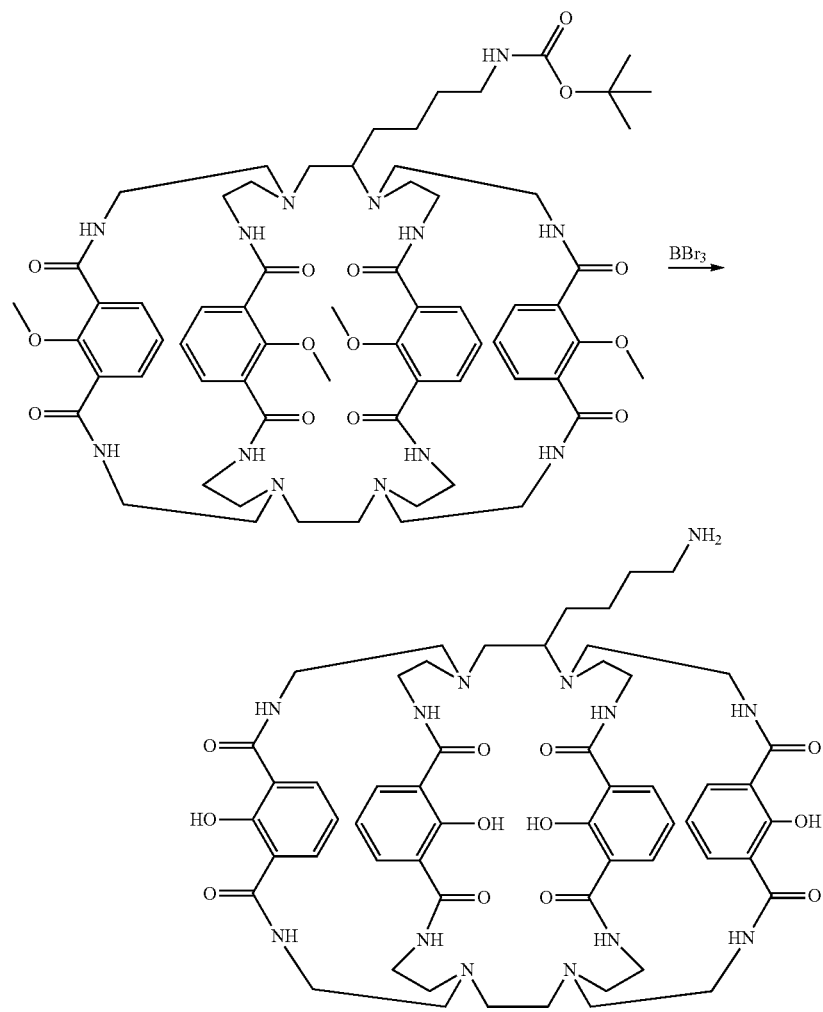

Another exemplary method of attaching a second cap moiety is described in Scheme 14.
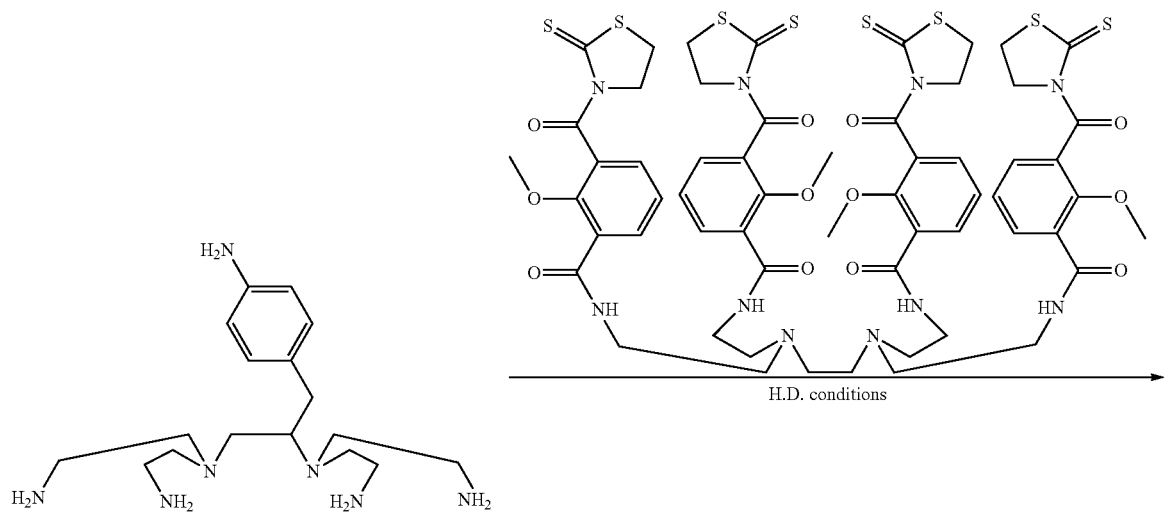
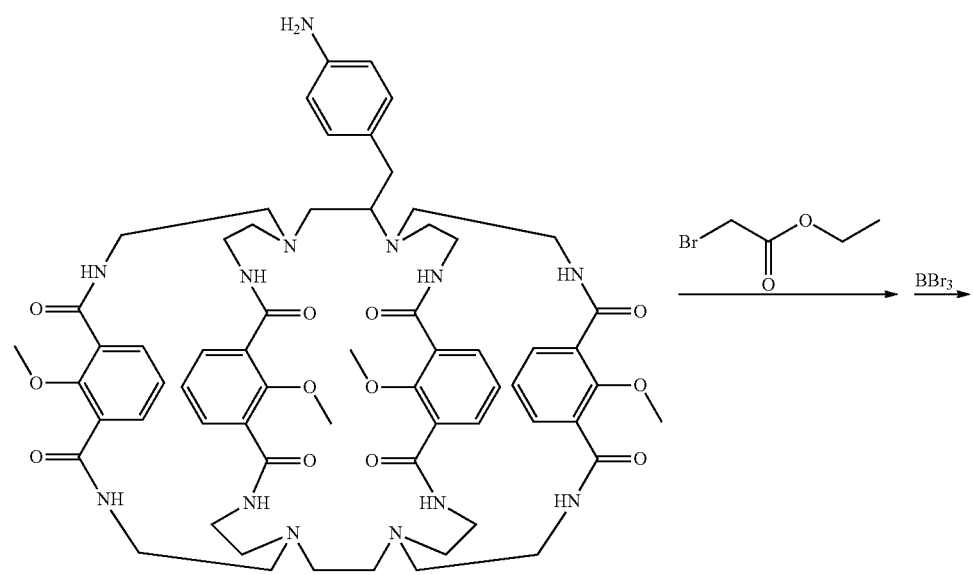

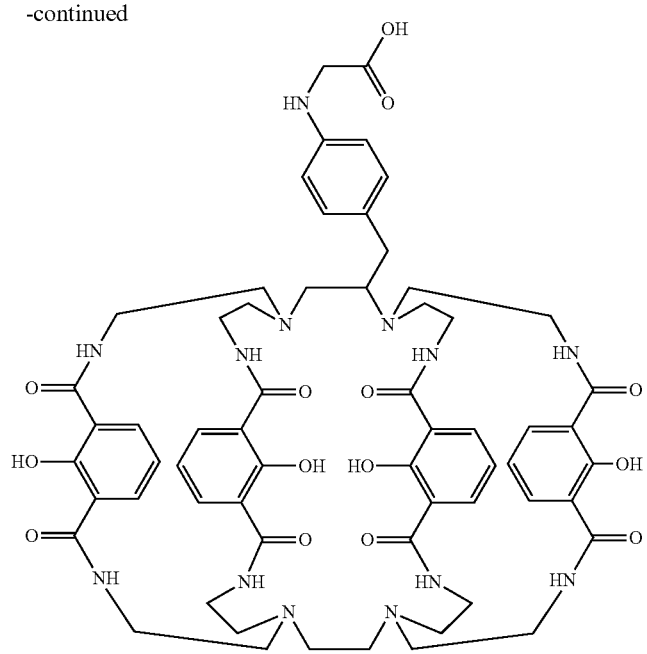
Another exemplary method of attaching a second cap moiety is described in Scheme 15.
Scheme 15
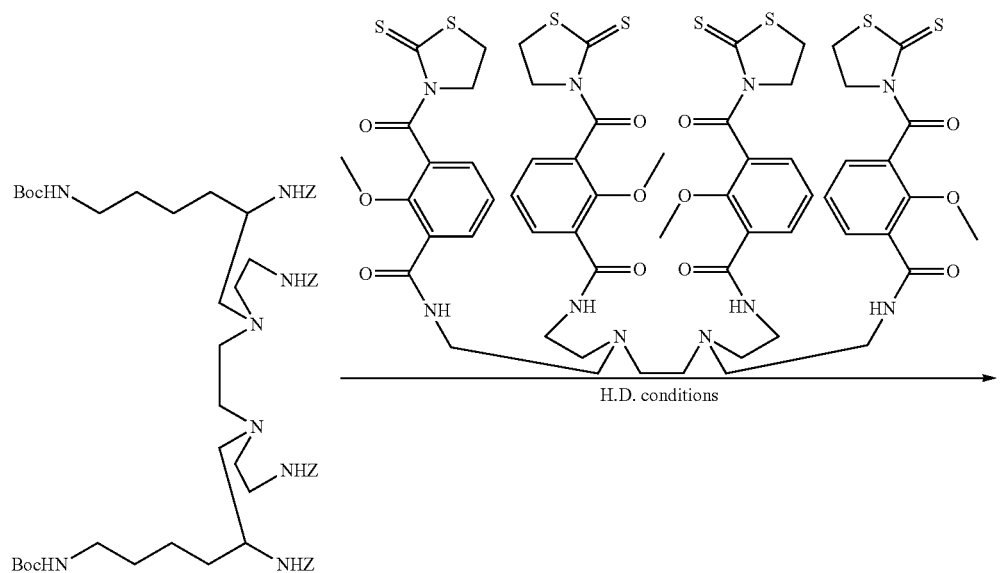

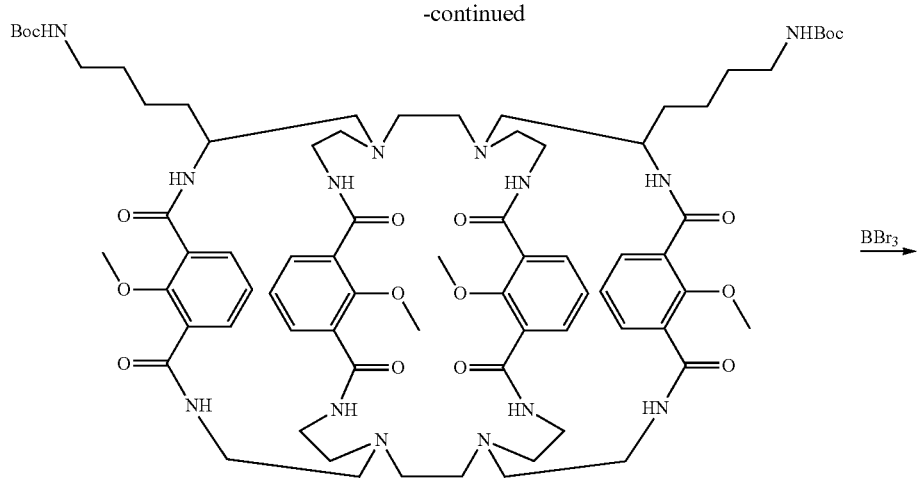
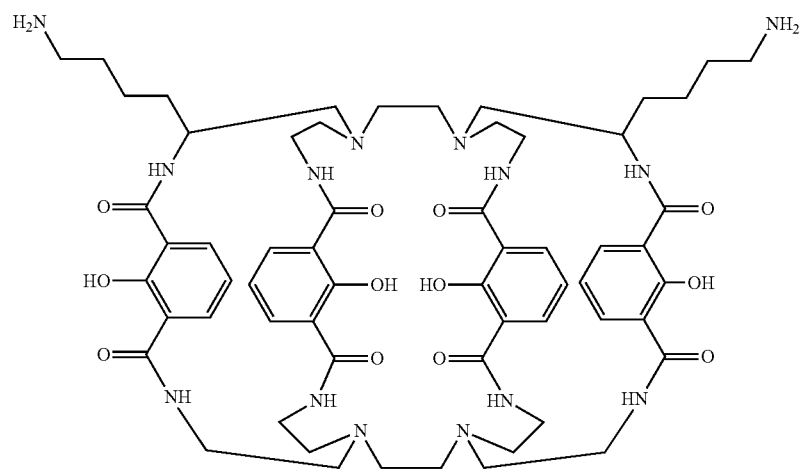
Another exemplary method of attaching a second cap moiety is described in Scheme 16.
Scheme 16
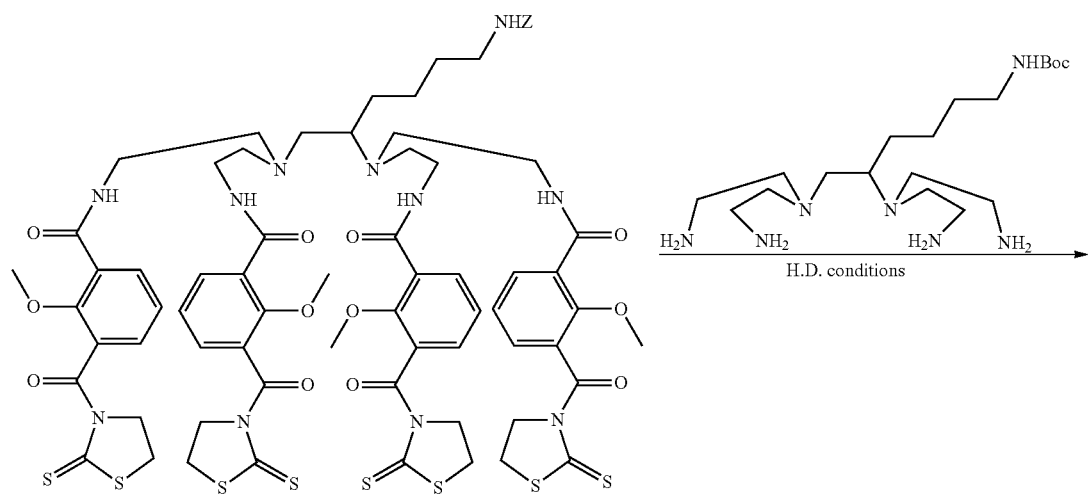

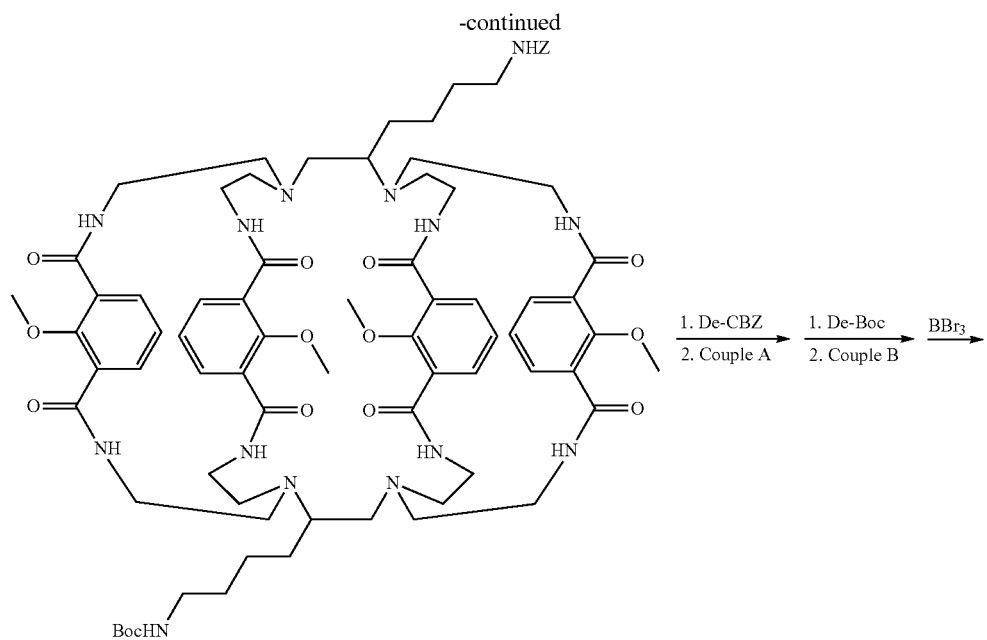
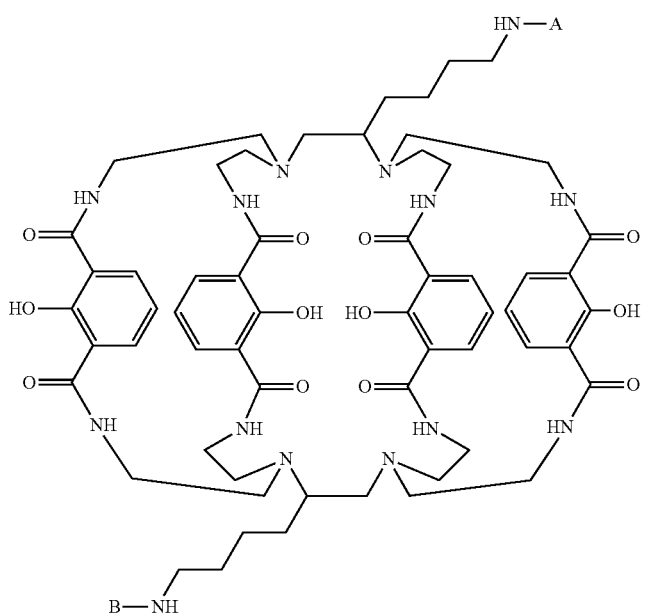

Another exemplary method of attaching a second cap moiety is described in Scheme 17.
Scheme 17
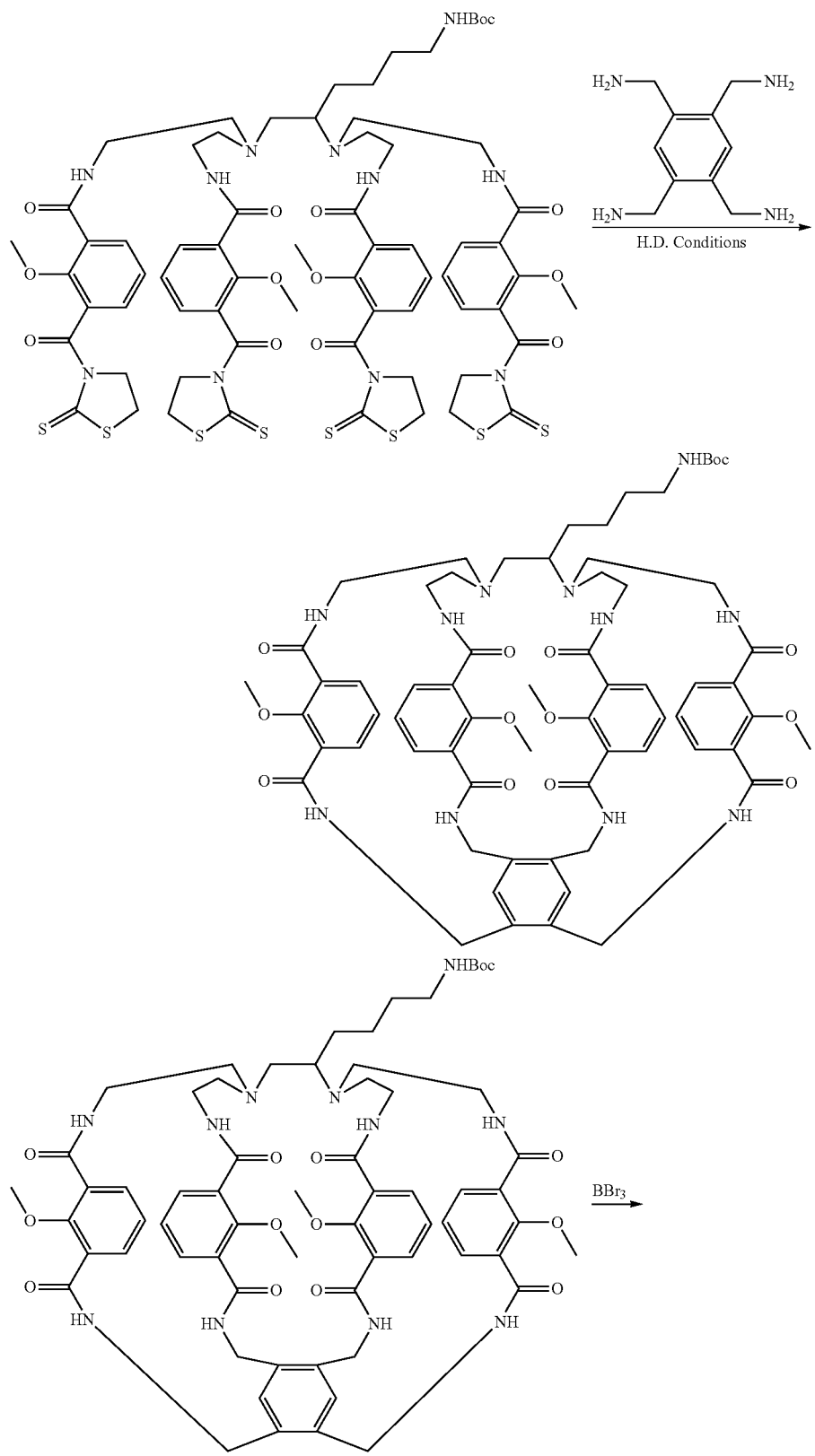

-continued

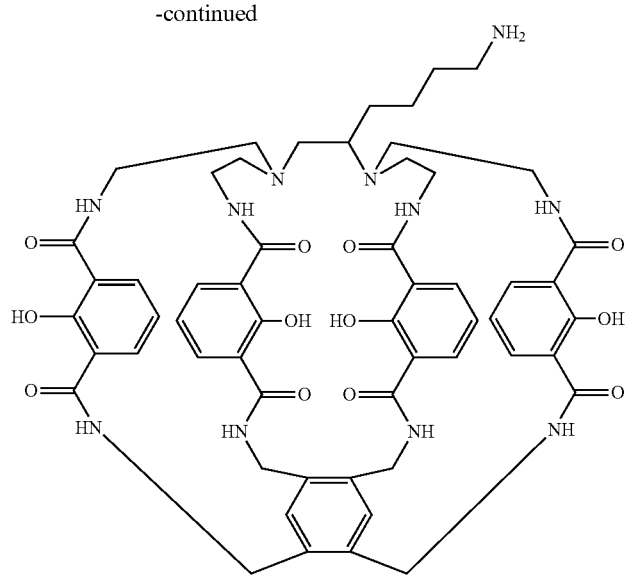

Functionalizing $L^{11}$-X

A variety of linker moieties can be attached to the compounds of the invention. The choice of linker moiety is informed by the moiety to which the molecule will be attached. For example, the following scheme has a maleimide moiety, which is useful for attachment to thiol moieties such as cysteine. Conditions for the attachment of a maleimide moiety to a compound of the invention are shown in Scheme 18.

Scheme 18

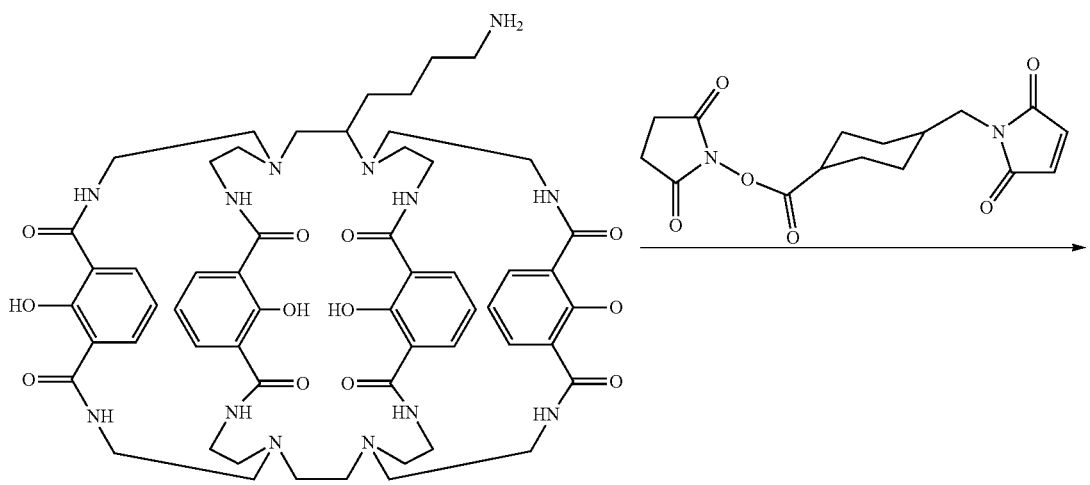

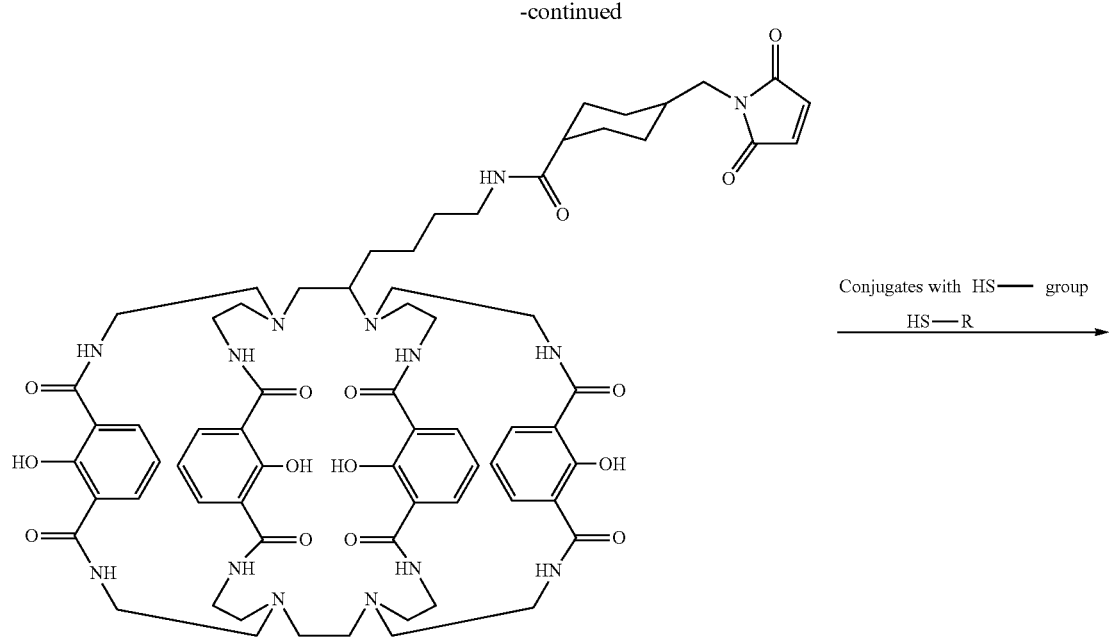
Conjugates with HS— group
HS—R
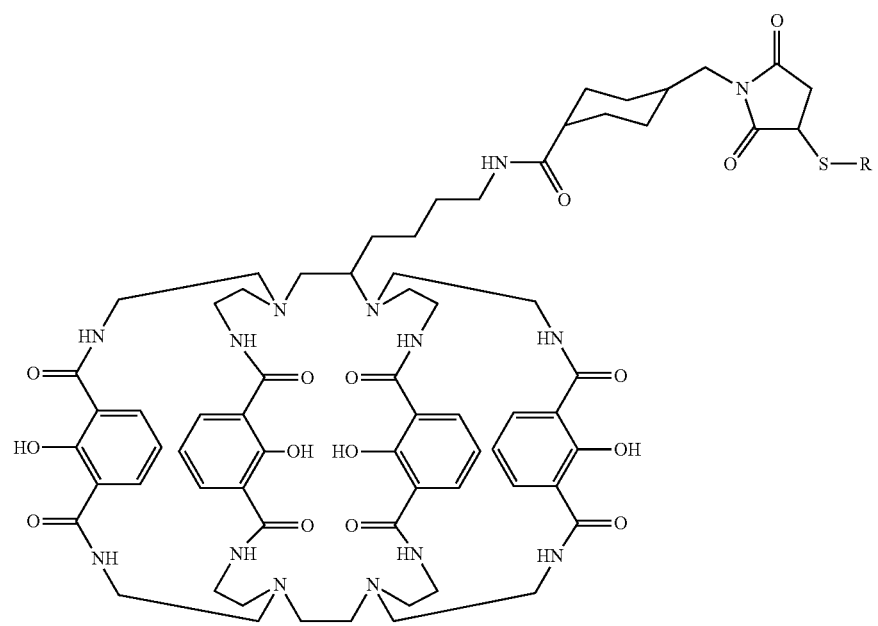

Another exemplary method for functionalizing $L^{11}$-X is described in Scheme 19.
Scheme 19
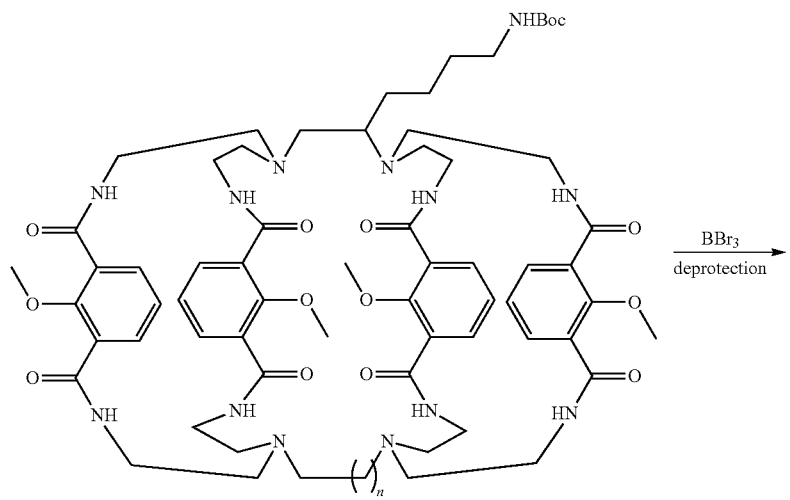
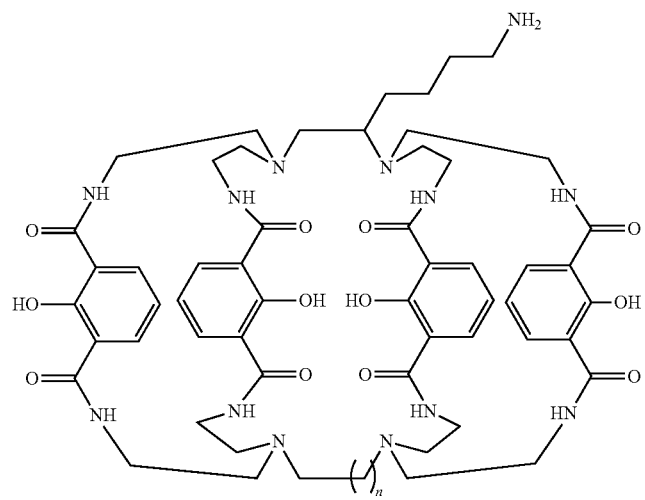

Another exemplary method for functionalizing $L^{11}$-X is described in Scheme 20. In this scheme, a phosphoramidite derivative of a compound of the invention is described for incorporation into an oligonucleotide chain.
Scheme 20
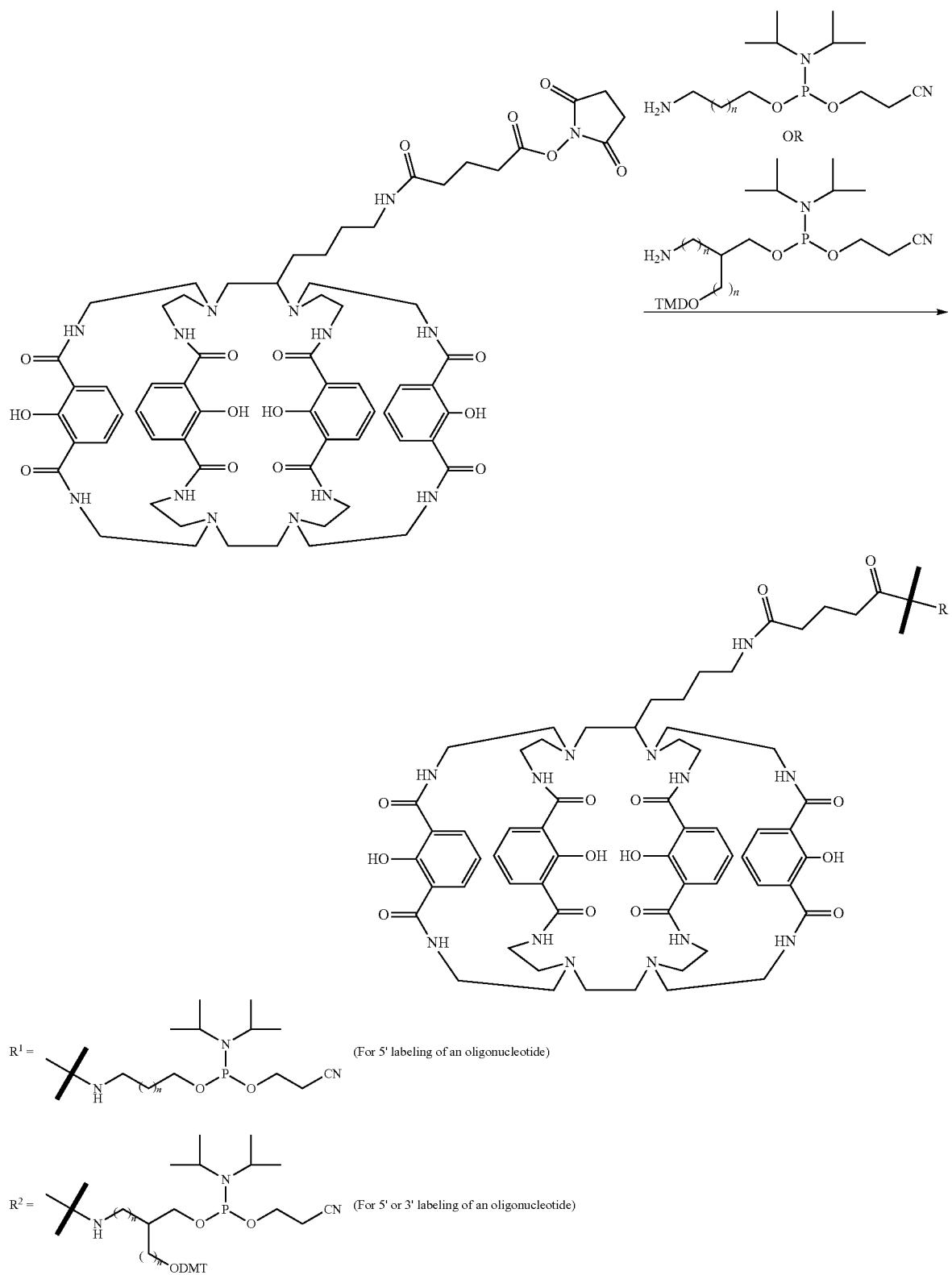

Another exemplary method for functionalizing $L^{11}$-X is described in Scheme 21. In this scheme, a carbohydrate-conjugated compound of the invention is described.
Scheme 21
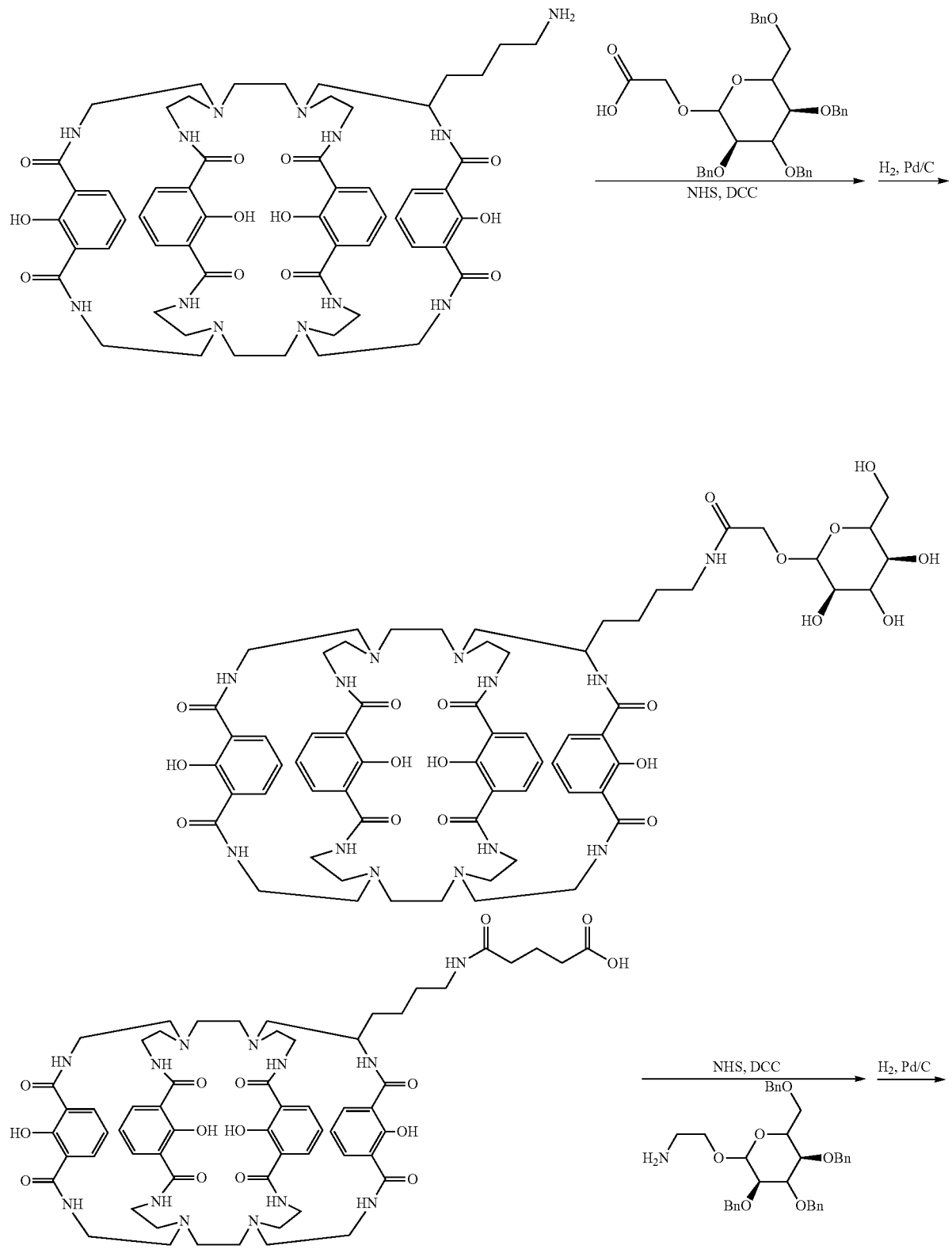

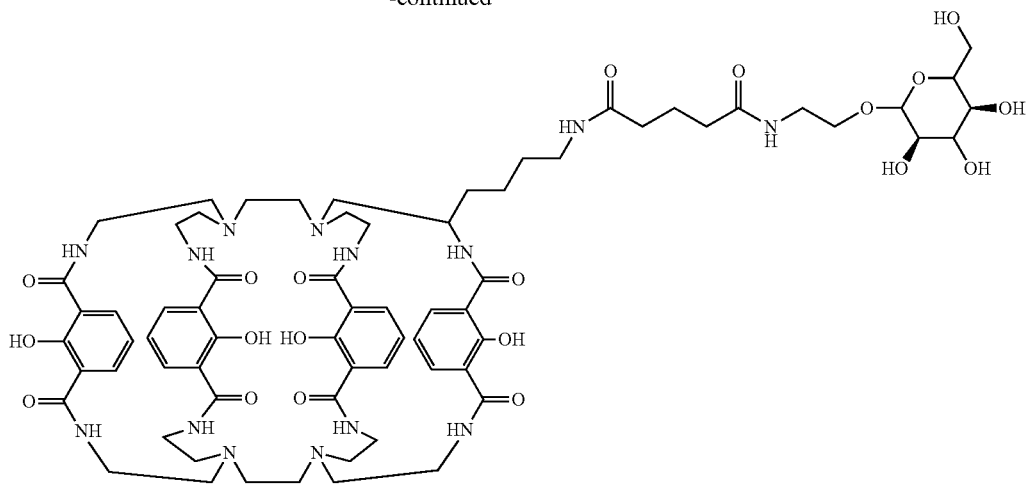

The hydroxy groups in saccharides or polysaccharides can be easily protected with acetoxy or benzyl groups. The protected carbohydrates can be derivatized with carboxyl or amino groups. Typical examples are:

Scheme 22

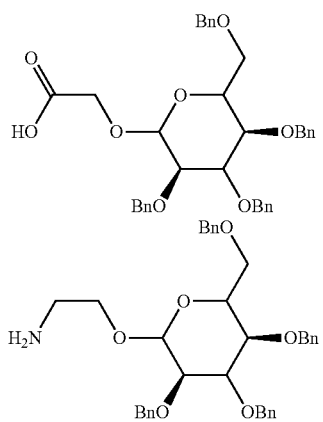

The above-recited synthetic schemes are intended to be exemplary of certain embodiments of the invention, those of skill in the art will recognize that many other synthetic strategies for producing the ligands of the invention are available without resort to undue experimentation.

The substituents on the isophthalamidyl group and the on the capping molecules joining the isophthalamidyl groups can themselves comprise chelating agents other than a hydroxyisophthalamidyl group. Preferably, these chelators comprise a plurality of anionic groups such as carboxylate or phosphonate groups. In a preferred embodiment, these non-PL chelating agents are selected from compounds which themselves are capable of functioning as lanthanide chelators. In another preferred embodiment, the chelators are aminocarboylates (i.e. EDTA, DTPA, DOTA, NTA, HDTA, etc. and their phosphonate analogs such as DTPP, EDTP, HDTP, NTP, etc).

Many useful chelating groups, crown ethers, cryptands and the like are known in the art and can be incorporated into the compounds of the invention. See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279-312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370-387; Kasina et al., *Bioconjugate Chem.*, 9: 108-117 (1998); Song et al., *Bioconjugate Chem.*, 8: 249-255 (1997).

In other embodiments substituents on the isophthalamidyl group or on the backbone are luminescence sensitizers. Exemplary sensitizers include rhodamine 560, 575 and 590 fluoresceins, 2- or 4-quinolones, 2 or 4-coumarins, or derivatives thereof e.g. coumarin 445, 450, 490, 500 and 503, 4-trifluoromethylcoumarin (TFC), 7-diethyl-amino-cumarin-3-carbohyddzide, etc., and especially carbostyril 124 (7-amino-4-methyl-2-quinolone), coumarin 120 (7-amino-4-methyl-2-coumarin), coumarin 124 (7-amino-4-(trifluoromethyl)-2-coumarin), aminomethyltrimethylpsoralen, napthalene and the like.

Complexes

In a second aspect, the invention provides complexes formed between at least one metal ion and a compound of the invention. In one exemplary embodiment, the metal is a member selected from the lanthanide group. Exemplary lanthanides include neodynium (Nd), samarium (Sm), europium (Eu), terbium (Tb), dysprosium (Dy) and ytterbium (Yb), of which europium and terbium are preferred. Other lanthanide ions, such as erbium (Er), lanthanum (La), gadolinium (Gd) and lutetium (Lu) are useful, but generally less preferred. In another preferred embodiment, the complexes of the invention are luminescent.

After the complexing agent is formed and purified, the metal complex can be synthesized by any of a wide range of art-recognized methods, including, for example, by incubating a salt of the chelate with a lanthanide salt such as the lanthanide trihalide, triacetate, and the like.

Luminescence Modifying Groups (Donor and Acceptor Moieties)

The luminescent compounds of the invention can be used with a wide range of energy donor and acceptor molecules to construct luminescence energy transfer pairs, e.g., fluorescence energy transfer (FET) probes. Fluorophores useful in conjunction with the complexes of the invention are known to those of skill in the art. See, for example, Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); Wang et al., *Anal. Chem.* 67: 1197-1203 (1995).

A non-limiting list of exemplary donor or acceptor moieties that can be used in conjunction with the luminescent complexes of the invention, is provided in Table 1.

TABLE 1

Suitable Moieties Useful
as Donors or Acceptors in FET Pairs 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
coumarin
    7-amino-4-methylcoumarin (AMC, Coumarin 120)
    7-amino-4-trifluoromethylcouluarin (Coumaran 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
    fluorescein isothiocyanate
    QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:

TABLE 1-continued

Suitable Moieties Useful
as Donors or Acceptors in FET Pairs pyrene
    pyrene butyrate
    succinimidyl 1-pyrene butyrate
quantum dots
Reactive Red 4 (Cibacron ™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
rhodamine X isothiocyanate
    sulforhodamine B
    sulforhodamine 101
sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
lanthanide chelate derivatives There is practical guidance available in the literature for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970). The literature also includes references providing exhaustive lists of luminescent and chromogenic molecules and their relevant optical properties, for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via readily available reactive groups that can be added to a molecule.

The diversity and utility of chemistries available for conjugating fluorophores to other molecules and surfaces is exemplified by the extensive body of literature on preparing nucleic acids derivatized with fluorophores. See, for example, Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a small molecular bioactive material, nucleic acid, peptide or other polymer.

In a FET pair, it is generally preferred that an absorbance band of the acceptor substantially overlap a luminescence emission band of the donor. When the donor (fluorophore) is a component of a probe that utilizes luminescence resonance energy transfer (LRET), the donor luminescent moiety and the quencher (acceptor) of the invention are preferably selected so that the donor and acceptor moieties exhibit luminescence resonance energy transfer when the donor moiety is excited. One factor to be considered in choosing the fluorophore-quencher pair is the efficiency of luminescence resonance energy transfer between them. Preferably, the efficiency of LRET between the donor and acceptor moieties is at least 10%, more preferably at least 50% and even more preferably at least 80%. The efficiency of LRET can easily be empirically tested using the methods both described herein and known in the art.

The efficiency of LRET between the donor-acceptor pair can also be adjusted by changing ability of the donor and acceptor to dimerize or closely associate. If the donor and acceptor moieties are known or determined to closely associate, an increase or decrease in association can be promoted by adjusting the length of a linker moiety, or of the probe itself, between the two luminescent entities. The ability of a donor and an acceptor in a pair to associate can be increased or decreased by tuning the hydrophobic or ionic interactions, or the steric repulsions in the probe construct. Thus, intramolecular interactions responsible for the association of the donor-acceptor pair can be enhanced or attenuated. Thus, for example, the association between the donor-acceptor pair can be increased by, for example, utilizing a donor bearing an overall negative charge and an acceptor with an overall positive charge.

In addition to fluorophores that are attached directly to a probe, the fluorophores can also be attached by indirect means. In some embodiments, a ligand molecule (e.g., biotin) is preferably covalently bound to the probe species. The ligand then binds to another molecule (e.g., streptavidin), which is either inherently detectable or covalently bound to a signal system, such as a luminescent compound of the invention, or an enzyme that produces a luminescent compound by conversion of a non-luminescent compound. Useful enzymes of interest as labels include, for example, hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc., as discussed above. For a review of various labeling or signal producing systems that can be used, see, U.S. Pat. No. 4,391,904.

Means of detecting luminescent labels are well known to those of skill in the art. Thus, for example, luminescent labels can be detected by exciting the fluorophore with the appropriate wavelength of light and detecting the resulting luminescence. The luminescence can be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product.

Methods

The compounds and complexes of the invention are useful as probes in a variety of biological assay systems and diagnostic applications. An overview of assay systems, such as competitive assay formats, immunological assays, microarrays, membrane binding assays and enzyme activity assays, is given e.g., in U.S. Pat. No. 6,864,103 to Raymond et al., which is incorporated herein in its entirety for all purposes. It is within the ability of one of skill in the art to select and prepare a probe that includes a complex of the invention, and which is suitable for each assay system. In an exemplary embodiment, the luminescent probe molecule is used to detect the presence or absence of an analyte in a sample.

Thus, in one aspect, the invention provides a mixture of a complex of the invention and an analyte.

In a another aspect, the invention provides a method of detecting the presence or absence of an analyte in a sample. The method comprises (a) contacting the sample and a composition including a complex of the invention; (b) exciting the complex; and (c) detecting luminescence from the complex. The presence or absence of the analyte can be indicated by the absence or presence of luminescence from the complex.

In a further aspect, the invention provides a method of detecting the presence or absence of an analyte in a sample. The method comprises (a) contacting the sample and a composition comprising a complex of the invention, and a luminescence modifying group, wherein energy can be transferred between the complex and the luminescence modifying group when the complex is excited, and wherein the complex and the luminescence modifying group can be part of the same molecule or be part of different molecules; and (b) exciting said complex; and (c) determining the luminescent property of the sample, wherein the presence or absence of the analyte is indicated by the luminescent property of the sample.

In an exemplary embodiment, the analyte, if present in said sample, competes with a probe molecule that includes a complex of the invention, for binding to a binding site located on a recognition molecule. In another exemplary embodiment, the analyte displaces the probe molecule from the binding site located on a recognition molecule, by binding to the binding site. In a further exemplary embodiment, the probe molecule is a complex of the invention.

Hence, in one aspect, the invention provides a kit including a recognition molecule and a compound or a complex of the invention. Exemplary recognition molecules include biomolecules, such as whole cells, cell-membrane preparations, antibodies, antibody fragments, proteins (e.g., cell-surface receptors, such as G-protein coupled receptors), protein domains, peptides, nucleic acids, and the like.

Analytes

The compounds, complexes and methods of the invention can be used to detect any analyte or class of analytes in any sample. A sample may contain e.g., a biological fluid (e.g., blood of a patient) or tissue. Other samples can e.g., include solutions of synthetic molecules or extracts from a plant or microorganism (e.g., for drug screening efforts). Exemplary analytes are pharmaceutical drugs, drugs of abuse, synthetic small molecules, biological marker compounds, hormones, infectious agents, toxins, antibodies, proteins, lipids, organic and inorganic ions, carbohydrates and the like. (see e.g., U.S. Pat. No. 6,864,103 to Raymond et al. for additional examples of analytes).

The following examples are provided to illustrate selected embodiments of the invention and are not to be construed as limiting its scope.

EXAMPLES

Example 1

Methyl 2-methoxy-3-methylbenzoate (E-1)

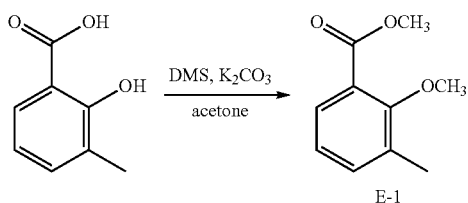

To a mixture of 3-methyl-salicylic acid (200 g, 1.32 mol), anhydrous potassium carbonate (500 gram, 3.6 mol) and dry acetone (3.5 L) in a 5 liter round bottle flask, dimethylsulfate (DMS, 210 mL, 2.2 mol) was added in several portions. After stirring at room temperature overnight, the mixture was heated at reflux, and the reaction was monitored by TLC. In order to complete the etherification, further additions of DMS and $K_2CO_3$ may be necessary. When TLC indicated the completion of the reaction, the mixture was refluxed 4 more hours to destroy any remaining DMS. The mixture was filtered, and the filtrate was evaporated to remove the solvents. A pale yellow thick oil was obtained as the raw product, yield 215 g (91%).

$^1$H NMR (500 MHz, $CDCl_3$, 25° C.) δ: 2.26 (s, 3H, $CH_3$), 3.78 (s, 3H, $OCH_3$), 3.85 (s, 3H, $OCH_3$), 6.98 (t, J=7.5, 1H, ArH), 7.27 (d, J=7.5, 1H, ArH), 7.58 (d, J=7.5, 1H, ArH); $^{13}$C NMR (500 MHz, $CDCl_3$, 25° C.) δ: 15.7, 51.8, 61.1, 123.2, 124.3, 128.8, 132.4, 134.8, 158.1, 166.6.

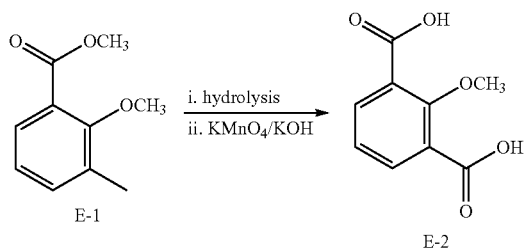

2-Methoxy-isophthalic Acid (E-2)

To a solution of compound E-2 (215 g, 1.19 mol) in a mixture of methanol (2 L) and water (0.5 L), potassium hydroxide pellets (100 gram, 1.5 mol) were added with cooling. The mixture was refluxed overnight, and then evaporated to dryness; the residue was then dissolved in water (0.5 L) and acidified with 6N HCl. 2-Methoxy-3-methylbenzoic acid precipitated as white crystals; yield 189 grams, 95%.

$^1$H NMR (500 MHz, $CDCl_3$, 25° C.) δ: 2.23 (s, 3H, $CH_3$), 3.71 (s, 3H, $OCH_3$), 7.06 (t, J=7.5, 1H, ArH), 7.36 (d, J=7.5, 1H, ArH), 7.49 (d, J=7.5, 1H, ArH).

To a mixture of 2-methoxy-3-methylbenzoic acid (75 gram, 0.45 mol) and water (4 L) in a 5 liter flask equipped with a mechanic stirrer and a heating mantle, sodium hydroxide (20 g, 0.5 mol) was added, and the mixture turned to be a clear solution. The solution was heated to 75° C., and potassium permanganate (158 g, 1 mol) was added in several batches during 6 hrs. The resulting brown slurry was stirred overnight; in the meantime, the temperature of the reaction mixture was kept in the range of 80-85° C.

The oxidation process was monitored by proton NMR (in $D_2O$-NaOD). If the characteristic peak of 3-methyl at 2.06 ppm in NMR was still recognizable, several grams more of potassium permanganate may be added to ensure the completion of the oxidation reaction. The slurry was then filtered to remove the large amount of $MnO_2$ and the filtrate was acidified with conc. HCl. It is noted that the precipitation of the crystalline product is slow. Pure product was obtained as snow-white crystals and was collected by filtration yield 75 grams, 85%. $^1$H NMR (500 MHz, DMSO-$d_6$, 25° C.) δ: 3.79 (s, 3H, $CH_3$), 7.24 (t, J=7.5, 1H, ArH), 7.79 (d, J=7.5, 2H, ArH).

2-Methoxy-isophthalic acid chloride (E-3)

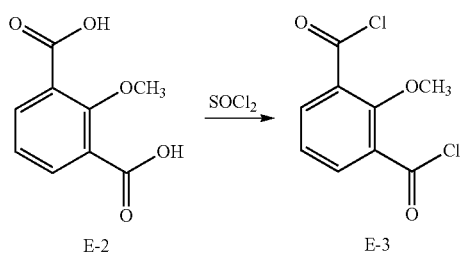

To a solution of 2-methyoxyisophthalic acid E-2 (75 g, 0.41 mol) in dry dioxane, thionyl chloride (119 g, 1 mol) and a drop of DMF were added with stirring. The mixture was refluxed overnight under $N_2$, then all the volatiles were removed by reduced pressure distillation, the residue was dried under vacuum (0.1 mm Hg) for at least 8 h. This moisture sensitive compound is pure enough for the next reaction step.

2-Methoxy-bis(2-mercaptothiazolide)isophthalamide (E-4)

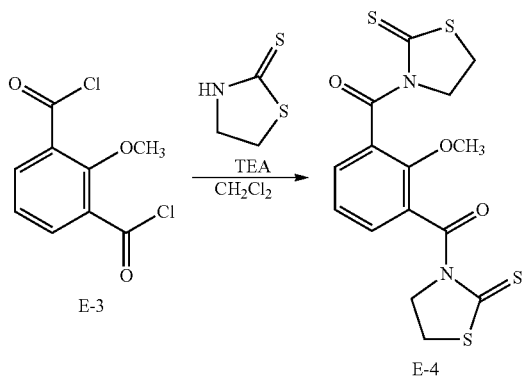

To the ice cooled solution of 2-mercaptothiozaline (107 g, 0.9 mol) and 150 mL of triethylamine in 350 mL dry THF was added a solution of compound E-3 (made from 75 g of 2-methoxy-isophthalic acid) in 300 mL dry THF drop-wise with stirring. A thick yellow slurry was produced which was stirred overnight and then filtered. The yellow filter cake was washed thoroughly with water, air dried and re-crystallized from 2-propanol to give 106.7 g of pure product. The filtrate was evaporated to dryness, dissolved in $CH_2Cl_2$, extracted with 1N HCl and 1N KOH successively, then purified by flash chromatography to give additional 31 g of product, total yield 137.7 g, 84%. $^1$H NMR (500 MHz, $CDCl_3$, 25° C.) (FIG. 7) δ: 3.419 (t, J=7.5, 2H, $CH_2$), 3.897 (s, 3H, $OCH_3$), 4.589 (t, J=7.5, 2H, $CH_2$), 7.137 (t, J=7.5, 1H, ArH), 7.433 (d, J=7.5, 1H, ArH). $^{13}$C NMR (500 MHz, $CDCl_3$, 25° C.) δ: 29.2, 55.6, 62.9, 123.1, 128.1, 131.9, 154.7, 167.1, 200.8. Anal. Calcd (Found) for $C_{15}H_{14}N_2O_3S_4 \cdot H_2O$(352.427): C, 43.25 (43.02); H, 3.87 (3.78): N, 6.72 (6.81).

Additional methods for functionalizing the isophthalamidyl moiety are described herein concerning functionalization at the (dd) and (ee) positions of FIG. 2.

Example 2

H(2,2)-amine or PENTEN (E-5)

Compound E-5 was synthesized by a slight modification of the reported procedure (Bianke K. Wagnont and Susan C. Jackels, *Inorg. Chem.* 1989, 28, 1923-1927):

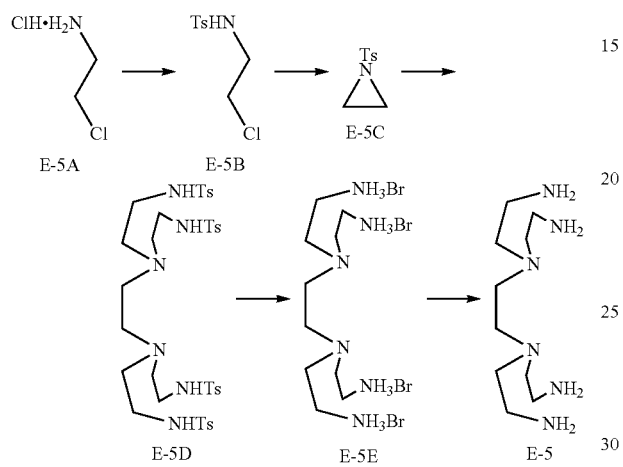

CIEtNHTs (E-5B)

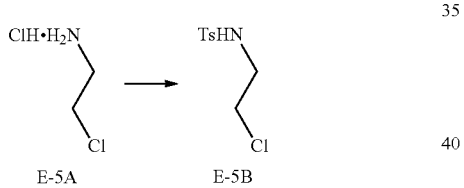

2-Chloroethylamine hydrochloride (E-5A) 70% aqueous solution (1 mol) and $K_2CO_3$ (1.2 mol) were dissolved in distilled water (4 Liter). TsCl (1 mol) was added slowly with stirring. The reaction mixture was stirred at room temperature for about 24 h. The pH of the reaction mixture was adjusted to 9 by slow addition of 4 M KOH solution and the mixture kept stirring until TLC indicated all the TsCl were quenched. The resulting precipitate was collected by using suction filtration, washed with distilled water, and dried in vacuo (220 g, 95% yield). mp: 77-78° C. $^1$H NMR (CDCl$_3$): δ 2.4 (3 H, s), 3.28 (2 H, q), 3.52 (2 H, t), 5.2 (1 H, s), 7.4 (2 H, dd), 7.9 (2 H, dd).

Tosylaziridine (E-5C)

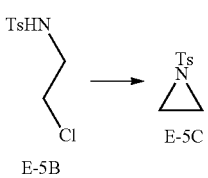

ClEtNHTs (100 g, 0.4 mol) was added to a stirred solution of NaOH (1200 mL, 1.4 M) in a salt/ice bath, and stirring was continued for about 1.5 h. The precipitate was then allowed to settle for overnight at 10° C. The product was collected, washed with cold distilled water, and dried in vacuo (180 g, 92% yield). mp: 51-52° C. $^1$H NMR (CDCl$_3$): δ 2.3 (4 H, s), 2.4 (3 H, s), 7.3 (2 H, dd), 7.8 (2 H, dd).

Penten-4-Ts (N,N,N',N'-tetrakis(tetrakis(2-((p-tolyl-sulfonyl)amino)-ethyl))ethylenediamine) (E-5D)

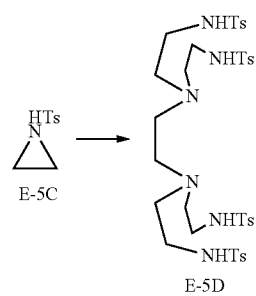

Tosylaziridine (80.8 g, 0.41 mol) was dissolved in dry toluene (160 mL) and acetonitrile (80 mL). A solution of ethylenediamine (6 g, 0.1 mol) in acetonitrile (80 mL) was added dropwise over a period of 1 h. The mixture was then heated at 60-65° C. overnight with stirring. After cooling, penten-4-Ts was collected as white fine crystals, washed with acetonitrile and vacuum dried at room temperature, yield 90%.

$^1$H NMR (CDCl$_3$): δ 2.41 (s, 12H, CH$_3$), 2.50 (s, 8H, CH$_2$), 2.95 (s, 12H, CH$_2$), 5.95 (br, 4H, NHTs), 7.2-7.9 (m, 16H, aromH).

Penten.6HBr (E-5E)

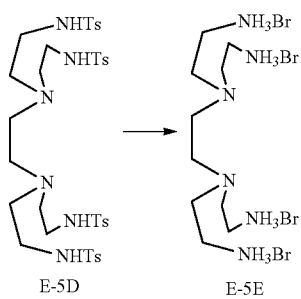

Compound E-5D (42.5 g, 0.5 mol) was dissolved in a mixture of HBr (300 mL) and acetic acid (200 mL) in a 1 L round-bottom flask. The flask was fitted with a condenser and heated to reflux for 48 h and then placed in an ice bath. The resulting precipitate was collected, washed with methanol and dried in vacuo (36 g, 95% yield).

$^1$H NMR (D$_2$O): δ 2.53 (8 H, d), 2.60 (2 H, d), 2.63 (2 H, d), 2.66 (8 H, m), 4.1 (8 H, s).

Penten (E-5)

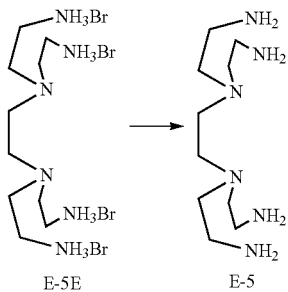

Penten (E-5) was prepared from the hydrobromide salt by ion-exchange chromatography. Dowex 1×8 resin in the basic (OH⁻) form was regenerated by using a 1% NaOH wash, followed by washes with $CO_2$-free water penten.6HBr (4.0 g, 0.4 mol) in $CO_2$-free water (40 mL) was loaded on the regenerated Dowex resin column (100 mL bed volume). The column was eluted with water, and fractions testing basic were collected. The collected fractions were evaporated to produce an oil (1.2 g, 95% yield). $^1$H NMR ($D_2O$): d 2.05 (s, 4H), 2.16 (t, 8H), 2.45 (t, 8H), 4.15 (s, 8H).

Example 3

Synthesis of functionalized H(2,2)amine cap (E-4)

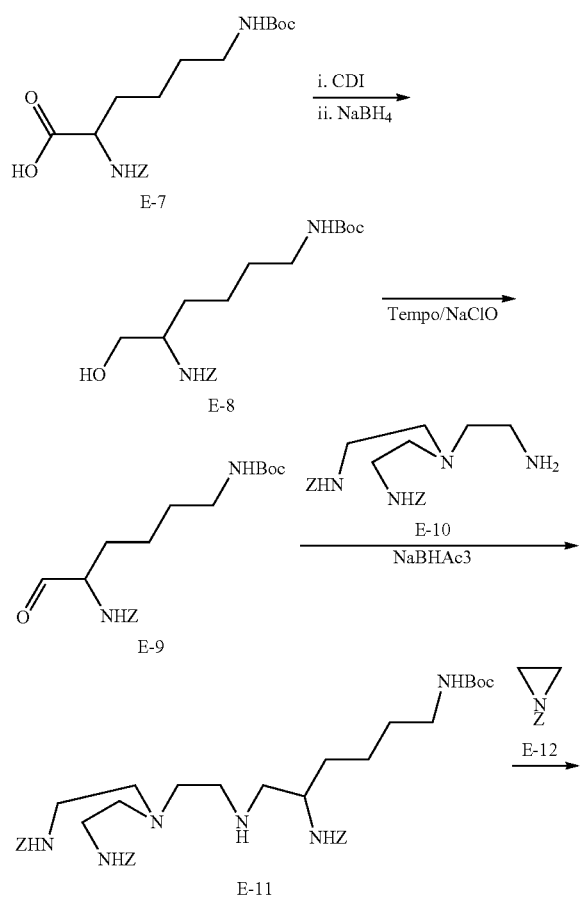

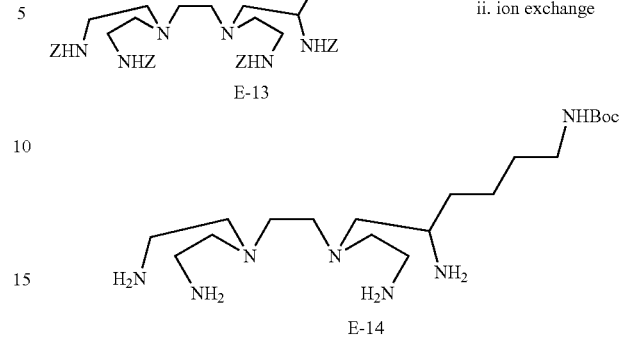

(5-Benzyloxycarbonylamino-6-hydroxy-hexyl)-carbamic acid tert-butyl ester (Cbz-Lys(Boc)-alcohol) (E-8)

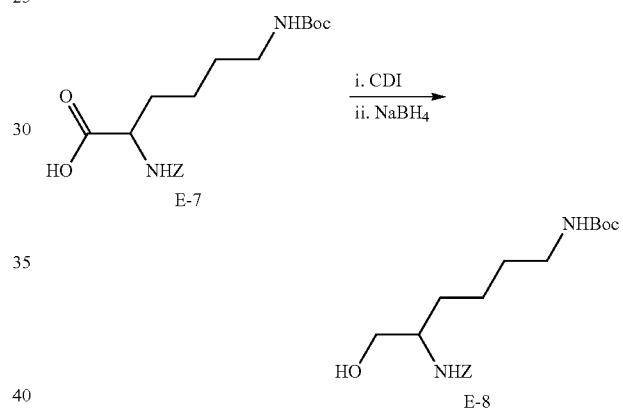

This compound was synthesized in 2001 in a 69% yield. Ripka, et al., *Org. Lett.,* 2001, 3(15), 2309. We found the routinely used mixed anhydride method (G. Kototos, *Synthesis,* 1990, 299) did not provide pure product, but the general CDI procedure (Kim et al., *Synlett,* 1999, 1239) can provide pure product with satisfactory yield. This procedure was modified slightly as follows:

To a stirred solution of 2-benzyloxycarbonylamino-6-tert-butoxycarbonylamino-hexanoic acid (Cbz-Lys(Boc)-OH) (Chem-Impex International, 3.8 g, 10 mmol) in THF (25 mL) in a 100 mL round flask was added 1,1'-carbonyldiimidazole (CDI) (1.7 g, 10.5 mmol) at room temperature. After 20 minutes, the THF solution was transferred via a Teflon canula (φ=2 mm) to a stirred solution of sodium borohydride (0.75 g, 20 mmol) in water (10 mL) in a 1 L round flask immersed in a water bath at 5-10° C. The addition caused a strong evolution of hydrogen gas and the mixture was stirred for a couple of hours. The volatiles were then removed on a rotovap, and the residue was dissolved in ethyl acetate (150 mL). The ethyl acetate solution was extracted successively with cold 1 N HCl (2×50 mL), saturated sodium bicarbonate solution (2×50 mL), brine (100 mL), and was dried with anhydrous sodium sulfate. The dried ethyl acetate solution was then pass through a one inch flash pad of silica gel, and concentrated to provide a colorless solid (3.3 g, 91%), TLC $R_f$=0.24 (95:5:2 EtOAc:MeOH:$H_2O$).

$^1$H NMR (500 MHz, CDCl$_3$, 25° C.): δ 1.34-1.59 (m, 6H, Lys CH$_2$), 1.42 (s, 9H, Boc CH$_3$), 2.29 (s, br, 1H, CH$_2$OH), 3.11 (m, 2H, CH$_2$), 3.63 (m, 3H, CH+CH$_2$), 4.60 (s, 1H, BocNH), 5.08 (s, 2H, CH$_3$), 5.10 (s, 1H, CbzNH), 7.32 (m, 5H, ArH). $^{13}$C NMR (500 MHz, CDCl$_3$): δ, 22.66, 28.41, 29.89, 39.73, 52.98, 64.82, 66.77, 79.28, 128.09, 128.12, 128.52, 136.47, 156.42, 156.79. MS (FAB, NBA) C$_{19}$H$_{30}$N$_2$O$_5$: [M+H]$^+$367.2.

(5-Benzyloxycarbonylamino-6-oxo-hexyl)-carbamic acid tert-butyl ester (Cbz-Lys(Boc)-aldehyde) (E-9)

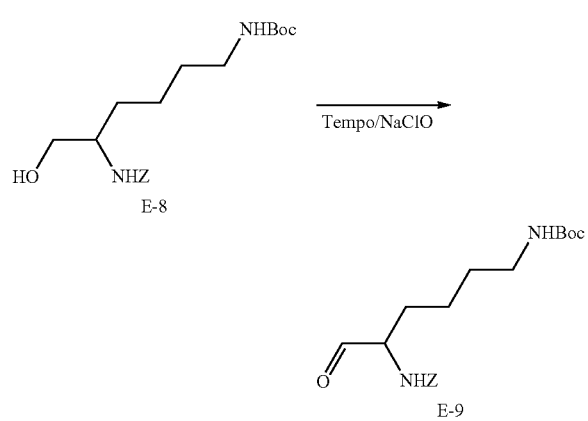

This aldehyde was synthesized in 1990 (McConnell, et al., J. Med. Chem. 1990, 33, 86-93) by treating Cbz-Lys(Boc)-methyl ester with diisobutylaluminum hydride. (Rich et al., J. Org. Chem., 1978, 43, 3624). In our laboratory, the corresponding alcohol was converted to the corresponding amino aldehyde via oxammonium oxidation (Leanna, et al., Tet. Lett. 1992, 32(35), 5029).

A 500 mL 3-necked Morton flask containing Cbz-Lys(Boc)-alcohol (3.66 g. 0.01 mol), TEMPO free radical (0.014 g. 0.0001 mol), and NaBr (1.1 g. 0.011 mol) in a bi-phasic mixture of toluene (30 mL)/ethyl acetate (30 mL) and water (5 mL) was immersed in a 0° C. ice water bath. With rapid mechanical stirring (1200 rpm), an aqueous solution made from mixing 6% commercial bleach (Cholorox$^{ultra}$) (14 mL), water (20 mL) and KHCO$_3$ (2.5 g, 0.025 mol) was added through a Teflon tube with a glass capillary tip over a period of 1 h and stirred for an additional 10 min. The aqueous layer was separated and washed with toluene (10 mL). The combined organic layers were washed with a solution of KI (0.1 g) dissolved in 10% aqueous KHSO$_4$ (15 mL). The iodine-colored organic layer was then washed successively with 10% aqueous sodium thiosulfate (10 mL), pH 7 phosphate buffer (0.2 M, 20 mL) and saturated brine. Drying with anhydrous Na$_2$SO$_4$, filtration and concentration gave 3.1 g (85%) of raw aldehyde (E-9) as colorless thick oil, which was purified by flash chromatography (5-20% EtOAc in CH$_2$Cl$_2$). The appropriate fractions were combined and the solvents were removed under vacuum, to leave white solid as product. The pure compound retained reactivity if stored in a freezer over months.

$^1$H NMR (500 MHz, CDCl$_3$, 25° C.): δ 1.32-1.86 (m, 6H, Lys CH$_2$), 1.41 (s, 9H, Boc CH$_3$), 3.10 (s, br, 2H, CH$_2$), 4.27 (m, 1H, CH), 4.58 (s, br, 1H, BocNH), 5.10(s, 2H, CH$_3$), 5.53 (d, 1H, J=6 Hz, CbzNH), 7.31 (m, 5H, ArH), 9.57 (s, 1H, aldehydeH). MS (FAB, NBA) C$_{19}$H$_{28}$N$_2$O$_5$: [M+H]$^+$365.2.

{2-[(2-Amino-ethyl)-(2-benzyloxycarbonylamino-ethyl)-amino]-ethyl}-carbamic acid benzyl ester (BisCbzTREN) (E-10)

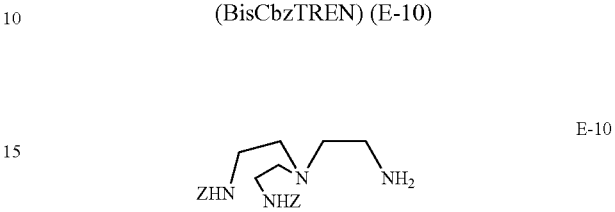

This is also a known compound, (Jap. Pat. No. 11302243, Takayanagi, Hisao, Mitsubishi Chemical Industries). The patent reported a multi-step synthesis using ethylenediamine as a starting material. We found that compound E-10 can be prepared in a one step reaction under mild conditions:

Benzyl Phenyl Carbonate* (Pittelkow, et al., Synthesis, 2002, 2195) (4.56 g, 20 mmol) was added to a stirring solution of TREN (1.46 g, 10 mmol) in absolute EtOH (50 mL) while cooling with an ice bath. The reaction mixture was stirred over night at room temperature. The volatiles were removed in vacuo, dissolved in minimum amount of CH$_2$Cl$_2$ and loaded onto a flash silica column; compound E-10 was separated by gradient chromatography with 3-10% CH$_3$OH+1% TEA in CH$_2$Cl$_2$. The isolated appropriate fractions were combined and pass through a strong basic alumina plug, and concentrated to afford pure BisZ-TREN as a thick colorless oil at 75% yield.

$^1$H NMR (500 MHz, CDCl$_3$, 25° C.): δ 2.48 (t, 2H, J=5.5 Hz, CH$_2$), 2.56 (s, br, 4H, CH$_2$), 2.67 (t, 2H, J=5.5 Hz, CH$_2$), 3.23 (s, br, 4H, CH$_2$), 5.06 (s, 2H, CH$_2$), 5.72 (s, 2H, CbzNH), 7.04 (m, 10H, ArH). $^{13}$C NMR (500 MHz, CDCl$_3$): δ, 38.91, 39.35, 53.82, 52.69, 66.28, 127.78, 127.82, 136.58, 156.70. MS (FAB, NBA) C$_{22}$H$_{30}$N$_4$O$_4$: [M+H]$^+$415.

*Carbonic Acid Benzyl Ester Phenyl Ester (Benzyl Phenyl Carbonate) (Pittelkow, et al., Synthesis, 2002, 2195)

This compound is a known compound, but it is not commercially available. It was prepared by following a published procedure. (Rich et al., J. Org. Chem., 1978, 43, 3624). To a mixture of benzyl alcohol (freshly distilled, 69.2 g, 0.64 mol), pyridine (64 mL) and CH$_2$Cl$_2$ (115 mL) in a 500 mL 3-necked flask equipped with a condenser, mechanical stirring and an addition funnel was added phenyl chloroformate (100 g, 0.64 mol) over a period of 1 h. The reaction mixture was stirred for an additional 3 h, and H$_2$O (160 mL) was added. The organic phase was washed with aqueous H$_2$SO$_4$ (2 M; 150 mL), dried over anhydrous Na$_2$SO$_4$, filtered and concentrated in vacuo. The crude product was distilled in vacuum 127-131° C./0.1 mm Hg to give the desired compound as colorless oil, Yield: 108 g (94%) (literature yield: 79%).

¹H NMR (500 MHz, CDCl₃, 25° C.): δ 5.37 (s, 2H, CH₂), 7.18-7.48 (m, 10 H, ArH). MS (FAB): m/z=372.1 (MH⁺).

(5-Benzyloxycarbonylamino-6-{2-[bis-(2-benzyloxycarbonylamino-ethyl)-amino]-ethylamino}-hexyl)-carbamic acid tert-butyl ester (TrisCbzLysBocTREN) (E-11)

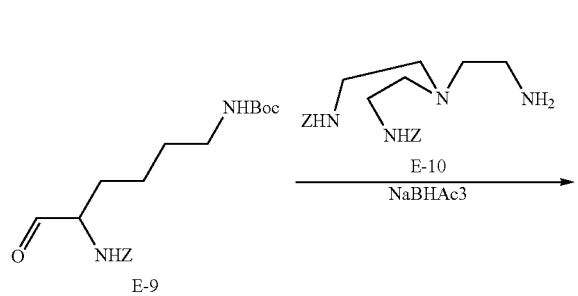

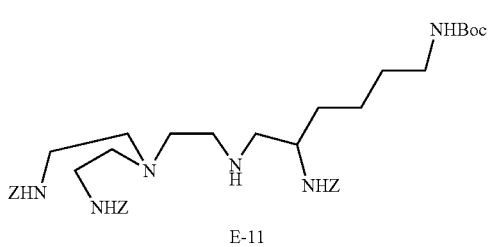

BisCbz-TREN (E-10) (4.14 g, 10 mmol) and Cbz-Lys(Boc)-aldehyde (E-9) (3.64 g, 10 mmol) were mixed in THF (50 mL) at room temperature under N₂. The mixture was stirred for 3 hrs with 0.2 g of activated 4 Å molecular sieves, then sodium triacetoxyborohydride (3.18 g, 15 mmol) was added and the mixture stirred at room temperature under a N₂ atmosphere for 24 h. Aqueous 1 N NaOH was added to quench the reaction mixture, and the mixture was extracted with dichloromethane (3×50 mL). The dichloromethane extract was loaded onto a flash silica gel column. The appropriate fractions of a gradient elution (3-10% methanol in dichloromethane) were collected and evaporated to dryness to give a pale beige thick oil, which solidified upon standing, yield: 6.27 g, 82%.

¹H NMR (500 MHz, CDCl₃, 25° C.): δ 1.17 (s, br, 2H, Lys CH₂), 1.24-1.89 (m, 4H, Lys CH₂), 1.41 (s, 9H, Boc CH₃), 2.53 (s, br, 8H, Tren CH₂), 3.03 (s, 2H, BocNHCH₂), 3.14 (s, 2H, CbzNHCH₂), 3.20 (s, 2H, CbzNHCH₂), 3.64 (s, br, 1H, Lysine chiral CH), 4.54 (s, 1H, BocNH), 5.05 (m, 6H, CbzCH₂), 7.27 (m, 15H, ArH).

¹³C NMR (500 MHz, CDCl₃): δ, 22.80, 28.33, 29.54, 32.52, 39.40, 39.97, 47.41, 50.85, 53.77, 54.34, 66.45, 78.93, 79.27, 127.92, 128.06, 128.35, 136.59, 156.01, 156.68, 156.86. MS (FAB, NBA) C₄₁H₅₈N₆O₈: [M+H]⁺763.5.

[5-Benzyloxycarbonylamino-6-((2-benzyloxycarbonylamino-ethyl)-{2-[bis-(2-benzyloxycarbonylamino-ethyl)-amino]-ethyl}-amino)-hexyl]-carbamic acid tert-butyl ester (E-13)

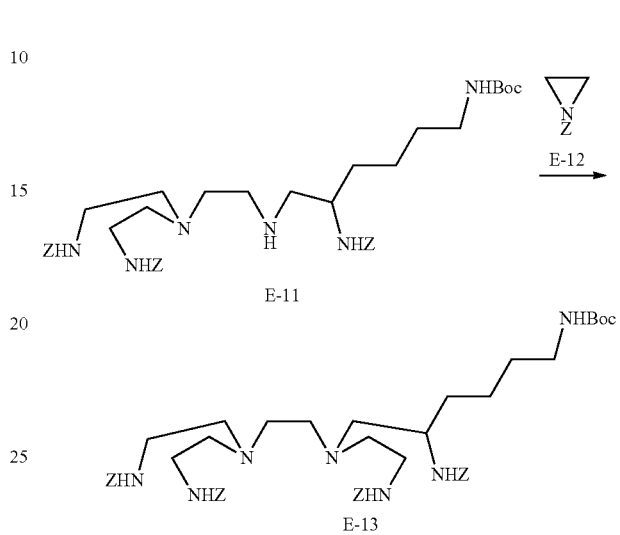

TrisCbzLysBocTREN (E-11) (3.81 g, 5 mmol) and Cbz-aziridine*(E-12) (1.24 g, 7 mmol) were mixed in tert-butanol (50 mL) at room temperature under N₂. The mixture was stirred under a N₂ atmosphere at 80° C. for 16 hrs until TLC indicated that the reaction had reached completion. The volatiles were removed under vacuum and the residue was dissolved in dichloromethane. The appropriate fractions of a gradient flash silica gel column (1-7% methanol in dichloromethane) were collected and evaporated to dryness to give a pale beige thick oil; yield: 3.98 g, 84.7%.

¹H NMR (500 MHz, CDCl₃, 25° C.): δ 1.24-1.87 (m, 6H, Lys CH₂), 1.42 (s, 9H, Boc CH₃), 2.26 (s, br, 2H, CH₂), 2.47 (m, br, 6H, CH₂), 2.58 (s, br, 2H, CH₂), 2.93-3.35 (m, br, 8H, CH₂), 5.05 (m, 8H, CbzCH₂), 7.27 (m, 20H, ArH).

¹H NMR (300 MHz, DMSO-d₆, 25° C.): δ 1.12-1.55 (m, 6H, Lys CH₂), 1.34 (s, 9H, Boc CH₃), 2.60 (m, 2H, CH₂), 2.43 (s, 8H, CH₂), 2.85 (m, 2H, CH₂), 3.01 (s, 6H, CH₂), 3.43 (s, 1H, CH), 4.98 (s, 8H, CbzCH₂), 6.71 (t, 1H, J=8 Hz, Amide H), 6.92 (d, 1H, J=8 Hz, Amide H), 7.01 (t, 1H, J=8 Hz, Amide H), 7.07 (t, 2H, J=8 Hz, Amide H), 7.31 (s, br, 20H, ArH). ¹³C NMR (500 MHz, CDCl3): δ, 22.78, 28.37, 29.65, 31.15, 32.96, 38.54, 38.67, 40.09, 49.36, 52.09, 52.31, 59.35, 66.47, 69.10, 78.94, 127.94, 127.97, 128.02, 128.11, 128.36, 128.38, 136.57, 136.64, 156.01, 156.68. MS (FAB, NBA) C₅₁H₆₉N₇O₁₀: [M+H]⁺940.5.

* Aziridine and its CBZ or Boc Derivatives

Aziridine or ethylenimine is a well-known compound. It can be prepared from 2-haloethylamine hydrohalides with strong base such as silver oxide; sodium or potassium hydroxide in aqueous solution. Synthesis of aziridine by treating 2-aminoethyl hydrogen sulfate with sodium hydroxide was recommended by Organic Synthesis (Allen, et al., "*Organic Synthesis*", V. 30, John Wiley and Son, Inc., New York, N.Y., 1950, pp. 38-40) and is the most common preparation method. Due to its high tendency to polymerize, the yield of preparation is low. A yield of 37% of aziridine was reported by *Organic Synthesis* and is considered a good yield.

Since aziridine is not commercially available now, the literature method (Reeves et al., *J. Amer. Chem. Soc.*, 1951, 73, 3522) was adopted with slight modifications to synthesize this compound. The key issue of the synthesis is to generate and vaporize the aziridine instantaneously and distill rapidly to reduce undesirable polymerization.

A 5-Liter, 3-neck flask fitted with a giant magnetic stir bar, a 250 mL dropping funnel and a prolonged condenser (composed of three condensers) arranged for distillation with a heating mantle was set in a well-ventilated hood (FIG. 5). 100 mL of 14% sodium hydroxide solution was placed in the 5-Liter flask, and was heated in a metal heater controlled by a regulator. The solution was heated at full capacity until the distillation was proceeding at a rapid rate. A cool solution made from 63 g 2-aminoethyl hydrogen sulfate, 78 g of sodium hydroxide and 270 mL water was added to the distillation flask through the dropping funnel at a rate such that the amount of liquid in the flask remained about constant. The superheated distillate that came over at 100 to 115° C. was collected in a receiving flask and which was immersed in an ice-bath. The flask has a side arm connected to an amine gas trap filled with dilute sulfuric acid.

In the literature, the distillate was treated with a huge amount of sodium hydroxide to salt out the raw aziridine, and it was redistilled to ensure the purity of the product. A large quantity of toxic, strongly basic waste would be generated and the re-distillation of the highly toxic and volatile aziridine is not advisable. Because the boiling point of aziridine and its dimer, the major contaminant, are 56-58° and 126-127.5° C. respectively, it is possible to control the purity of aziridine by only collecting the distillate that boils at 50-115° C. The distilled dilute aziridine solution was used directly for preparing Boc-aziridine and CBZ-aziridine without further treatment. The yield of aziridine was estimated around 60%. For characterization, a fraction of the distillate was saturated with excess sodium hydroxide, and the aziridine was separated as a thick oil. Its purity was confirmed by NMR spectroscopy.

$^1$H NMR (500 MHz, CDCl$_3$, 25° C.): δ, 0.56 (s, br, 1H, NH), 1.56 (s, 4H, CH$_2$). $^{13}$C NMR (500 MHz, CDCl$_3$): δ, 18.03.

Aziridine-1-carboxylic acid benzyl ester (Cbz-aziridine E-12)

E-12

The aziridine concentrations in the distillate calibrated by acid-base titration were in the range of 0.1 to 0.2 M. The solutions were used directly for preparation of Cbz-aziridine and Boc-aziridine.

To a stirred, distilled aziridine solution (500 mL, 0.1 mol) in a round-bottom flask cooling with an ice bath, three equivalents of potassium carbonate were added. After all of the solid dissolved, benzyl chloroformate (1.5 equivalents) in ethyl ether (150 mL) was added over 2 h. The solution was stirred overnight and warmed to room temperature, and the aqueous phase was extracted with methylene chloride (5×30 mL). The organic phases were combined and passed through a flash silica gel pad and concentrated to afford the Cbz-aziridine as colorless thick oil, yield: 7.2 g, 81%.

$^1$H NMR (500 MHz, CDCl$_3$, 25° C.): δ 2.22 (s, 4H, CH$_2$), 5.14 (s, 2H, CH$_2$), 7.34 (m, 5H, ArH). $^{13}$C NMR (500 MHz, CDCl$_3$, 25° C.): δ, 20.51, 65.93, 127.3, 127.4, 128.7, 140.9, 159 4.

[5-Amino-6-((2-amino-ethyl)-{2-[bis-(2-amino-ethyl)-amino]-ethyl}-amino)-hexyl]-carbamic acid tert-butyl ester (BocLys-H(2,2)amine) (E-14)

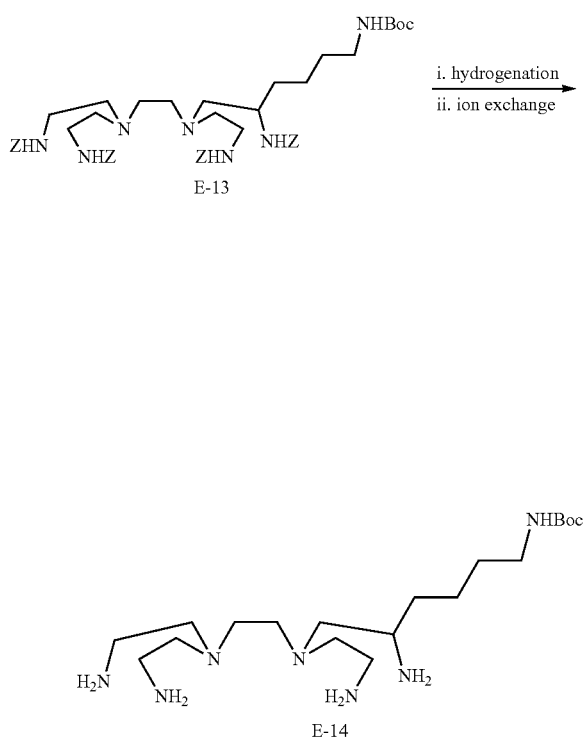

To a glass hydrogenation container with 200 mg of wet 5% Pd/C catalyst, 5 mL of methanol was carefully added along the glass wall to cover the catalyst (Caution: the catalyst is ignitable in the air). A solution of tetraCbzBocLys-H(2,2) amine (E-13) (0.94 g, 1 mmol) in methanol (30 mL) was added to the container. The container was put in a Parr bomb and hydrogenated at 500 psi pressure overnight. TLC showed no starting material remained, and the solvent was removed in vacuo. The BocLys-H(2,2)amine was obtained in its carbonate form as a clear colorless thick oil. The raw yield was 90%.

$^1$H NMR (500 MHz, CDCl$_3$, 25° C.): δ 1.24-1.87 (m, 6H, Lys CH$_2$), 1.42 (s, 9H, Boc CH$_3$), 2.41-2.82 (m, br, 10H, CH$_2$), 2.82-3.23 (m, br, 9H, CH$_2$), 3.29 (s, br, 1H, CH), 5.48 (s, 1H, BocNH), 8.52 (s, 3H, CarbonateNH). $^{13}$C NMR (500 MHz, CDCl$_3$): δ, 22.63, 28.39, 29.47, 31.11, 37.00, 39.93, 49.79, 51.99, 68.79, 78.62, 156.19, 168.99. MS (FAB, NBA) C$_{51}$H$_{69}$N$_2$O$_{10}$: [M+H]$^+$404.3722.

It was proved that this raw amine can not be used directly for successful cyclization reaction that leads to a macrotricycle IAM ligand. This raw product was passed though a Dowex 1×8 strong basic anion exchange resin to remove the carbonate. The resulted free amine was used for the next step, the cyclization reaction.

Example 4
Me4H(2,2)IAM-tetrathiazolide (E-6)
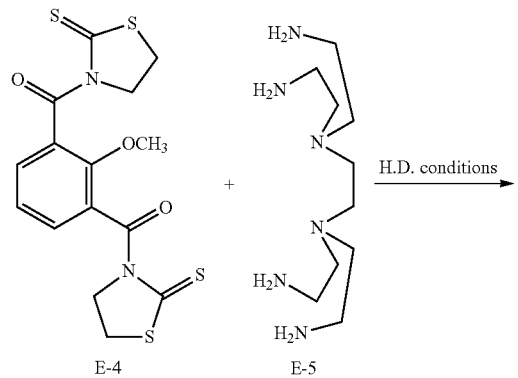
E-6

To a solution of E-4 (100 g, 0.25 mol) in CH$_2$Cl$_2$ (3 L), a solution of compound E-5 (1 g, 4 mmol) in 300 mL of CHCl$_3$ was added drop-wise over a period of 24 h. The reaction mixture was applied onto a flash silica gel column packed with CH$_2$Cl$_2$ and eluted with 3-5% 2-propanol in CH$_2$Cl$_2$ to separate the unreacted 1. The appropriate fractions of the successive gradient elution (5-20% iso-propanol in CH$_2$Cl$_2$) were combined and evaporated to dryness to give pure compound 6 as a yellow foam. Yield 4.5 g (83%).

$^1$H NMR (500 MHz, CDCl$_3$, 25° C.): δ 2.70 (s, 4H, CH$_2$), 2.76 (t, J=6.2 Hz, 8H, CH$_2$), 3.43 (t, J=7.2 Hz, 8H, CH$_2$), 3.53 (q, 8H, J=6.0 Hz, CH$_2$), 3.85 (s, 12H, OCH$_3$), 4.64 (t, J=7.5, 8H, CH$_2$), 7.17 (t, J=8.2 Hz, 4H, ArH), 7.79 (t, J=5.4 Hz, 4H, ArH), 8.63 (d, J=7.5, 1H, ArH). $^{13}$C NMR (500 MHz, CDCl$_3$, 25° C.) δ: 29.2, 37.9, 50.6, 53.5, 55.7, 63.1, 124.3, 127.2, 129.1, 132.0, 133.9, 155.6, 164.9, 167.3, 201.4. Anal. Calcd (Found) for C$_{58}$H$_{64}$N$_{10}$O$_{12}$S$_8$.H$_2$O(1367.73): C, 50.93 (51.02); H, 4.86 (4.98): N, 10.24 (10.01).

Example 5

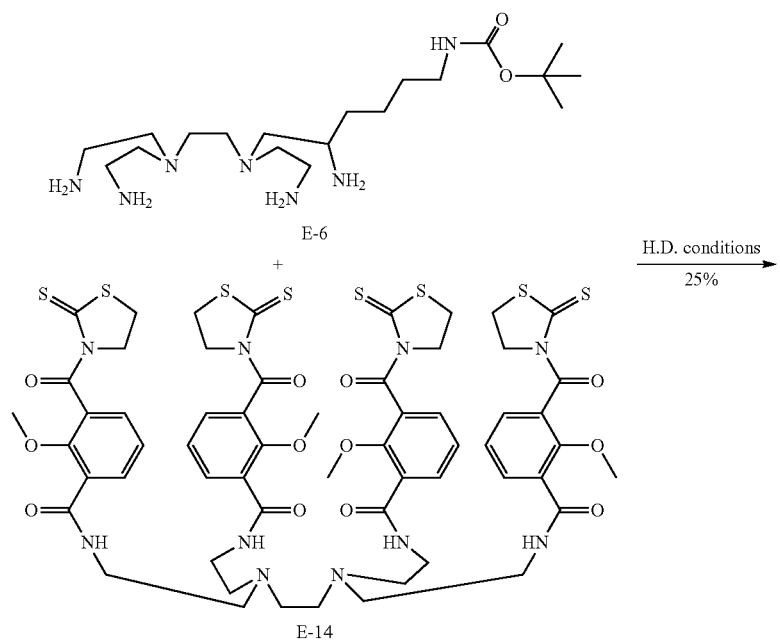

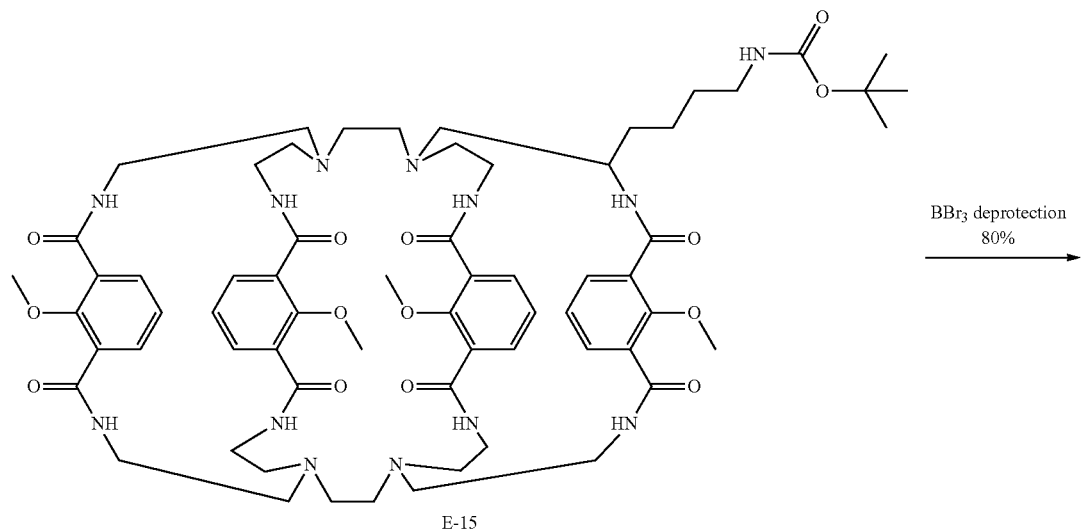

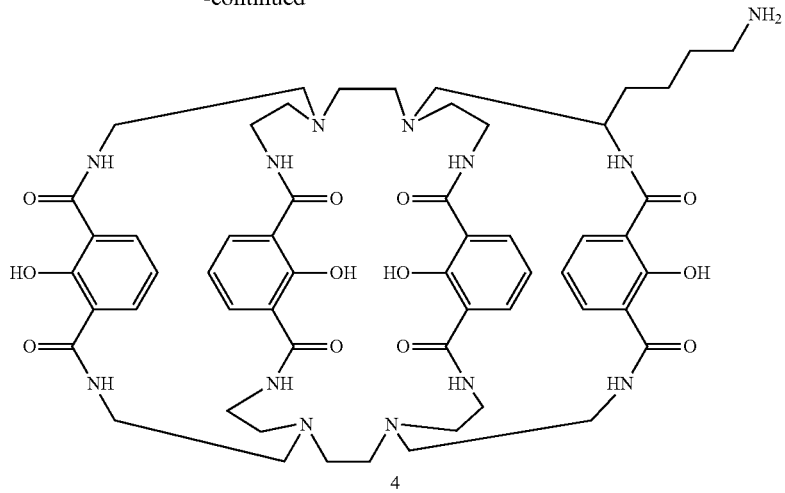

4

Me$_4$BocLysBH(2,2)IAM (E-15)

This pendant trimacrocycle E-15 was synthesized under high dilution conditions. The free amine (E-6) (1.2 g, 3 mmol), 5 mL of triethylamine and 10 mL of iso-propanol were mixed to form a homogeneous solution and dissolved in 950 mL of chloroform in a 1 L round bottom flask. On the other hand, H(2,2)IAMtetrathiazolide (E-14) (4.05 g, 3 mmol) was dissolved in 950 mL of chloroform in a separate 1 L round bottom flask. The solutions of the E-6 and E-14 (c.a. 3-4 mM) were added simultaneously via a homemade "Teflon tube-glass capillary slow addition system" to a 12 L three-neck round flask containing 8 liter of dichloromethane and 2 mL of triethylamine. The addition rates were adjusted to about 100-120 mL per 24 h for each reactant for 8-10 days, yielding a pale yellow color in the main reaction flask. It is necessary to keep the high dilution condition in order to minimize polymeric by-products. After all the reactants were consumed, the reaction mixture was stirred an additional 8 hours. TLC reveals the reaction mixture is a complicated mixture. Since there are many possible isomers coexisting for this asymmetric molecule, these isomers appear as different spots on the TLC plate. The reaction mixture was then passed through a flash silica plug (200 g) to recycle the solvents; the product and by-product remaining on the plug were washed down with a mixture of 20% isopropanol in $CH_2Cl_2$ containing 1% triethylamine. To simplify the purification and separation process, the washing solution containing the macrocycle E-15 and other by-products was treated with a basic alumina column then a flash silica gel column, the appropriate fractions of gradient (3-7% MeOH in $CH_2Cl_2$) elution of the flash silica column were combined, evaporated to provide compound E-15 at 25-30% yield. HPLC reveals that the purity of the raw product is about 90%. Further column purifications are needed to provide pure product.

Two main fractions with very different $R_f$ values (0.58 and 0.76, developed with a mixture of $AcOH/MeOH/CH_3CN/CH_2Cl_2$ in a ratio of 0.5/8/10/90) in about equal amount were isolated; Mass spectra revealed that both fractions are the desired macrocycle (E-15).

$^1$H NMR (500 MHz, DMSO-d$_6$, 25° C.): δ 1.24-1.55 (m, 15H, Boc CH$_3$+Lys CH$_2$), 2.52-2.95 (m, br, 24H, NCH$_2$), 3.21-3.62 (m, br, 16H, NHCH$_2$), 3.65-3.7 (m, 12H, CH$_3$), 6.78(s, 1H, BocNH), 7.01-7.15 (m, 8H, ArH), 7.50-7.62 (m, 16H, ArH), 8.15-8.30 (m, br, 8H, amideH). $^{13}$C NMR (500 MHz, CDCl$_3$): δ 23.12, 28.25, 28.27, 29.76, 31.06, 37.09, 38.36, 46.01, 50.12, 52.68, 53.48, 62.53, 62.73, 62.85, 78.73, 124.84, 126.61, 133.42, 133.82, 154.89, 155.91, 156.01, 164.69, 165.01, 165.28. MS [(+)-FAB, NBA)] $C_{65}H_{89}N_{13}O_{14}$: m/Z [M+H]$^+$1276.7.

LysBH(2,2)IAM (4)

Me$_4$BocLysBH(2,2)IAM (E-15) (0.22 g, 0.17 mmol) was dissolved in 20 mL of $CH_2Cl_2$ in a Schlenk flask with a Teflon stopcock. Under a flow of N$_2$, the solution was cooled to −10° C. before 1 mL BBr$_3$ was injected. The slurry was stirred for 5 days before pumping off the excess BBr$_3$ and $CH_2Cl_2$. The remaining light yellow solid was dissolved in methanol (100 mL) with cooling. The methanol solution was gently refluxed and left uncapped to allow the release of volatile boron compounds for 6 hrs. The solution was then evaporated to dryness. The residue was dissolved in methanol (10 mL) and diluted into water (50 mL). The mixed solution was boiled until the volume reduced to c.a. 10 mL and then was cooled, affording a white solid as product. It was collected by centrifugation and vacuum dried at 40° C. Yield: 150 mg (53%).

Compared to the un-functionalized highly symmetric molecule BCH(2,2)IAM, the NMR of compound 4 is complicated, probably due to the fact that this molecule is asymmetric and there are several conformers co-existing.

$^1$H NMR (500 MHz, D$_2$O—NaOD, 25° C.): δ 0.78-1.25 (m, 6H, LysCH$_2$), 2.15-2.30 (m, 2H, CH$_2$), 2.40-2.92 (m, 26H, NCH$_2$), 3.00-3.45 (m, 14H, NHCH$_2$), 3.66 (s, br, 1H, CH), 6.08-6.52 (m, 4H, ArH), 7.35-7.90 (m, 8H, ArH). MS [(+)-FAB, TG/G)] $C_{56}H_{73}N_{13}O_{12}$: m/Z 1120.5 [MH$^+$]. Anal. Calcd. (Found) for $C_{56}H_{73}N_{13}O_{12}$.5HBr.8 H$_2$O (1668.95): C, 40.30 (40.29); H, 5.68 (5.68); N, 10.91 (10.65).

Example E-6
Syntheses of macrotricyclic products (compounds 19, 20, 21)
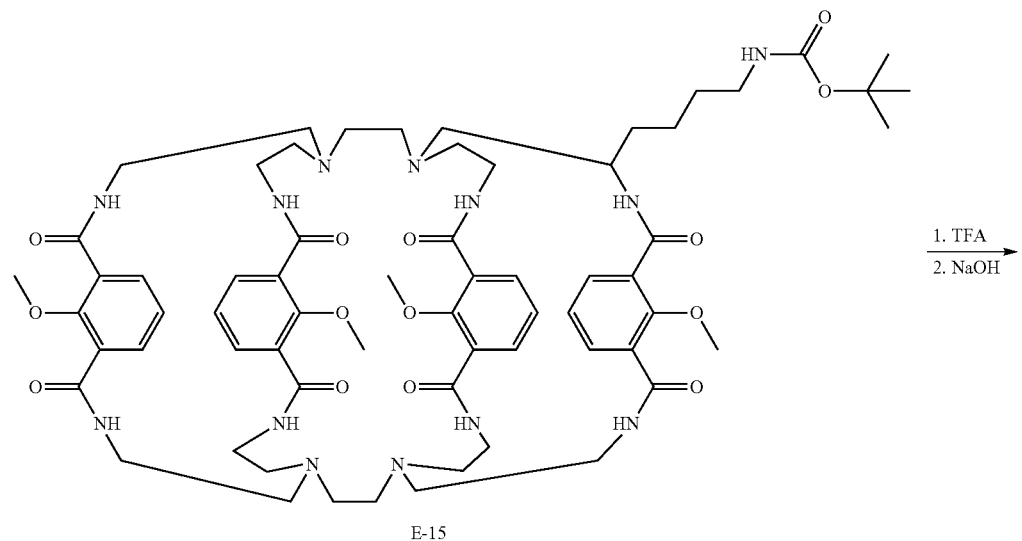
E-15
1. TFA
2. NaOH
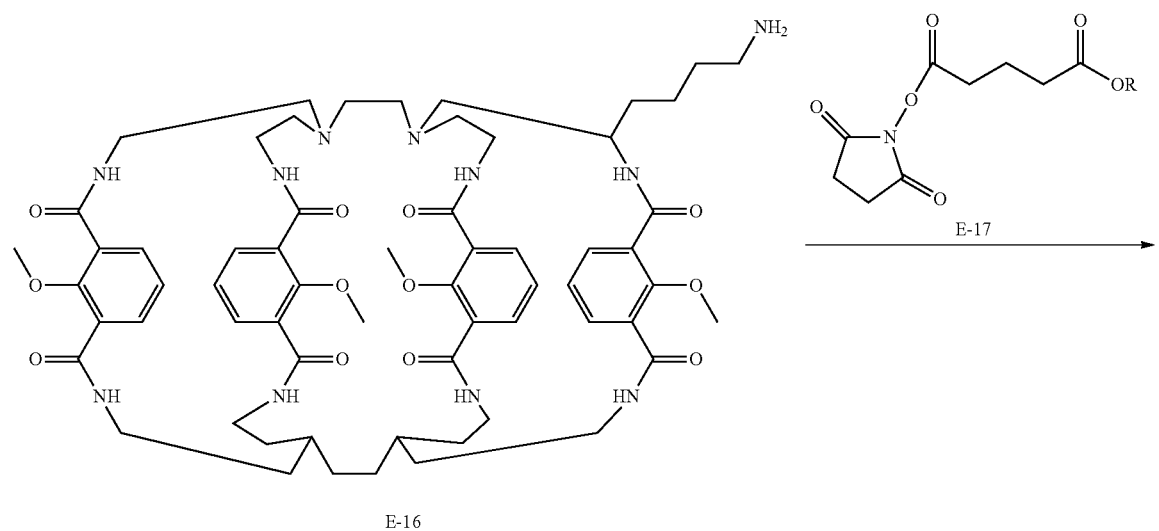
E-16
E-17
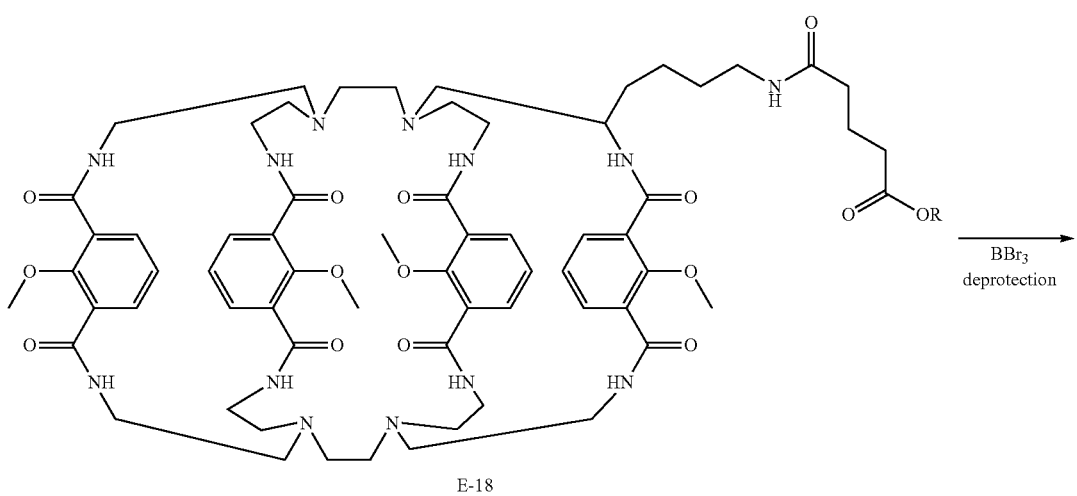
E-18
BBr$_3$ deprotection

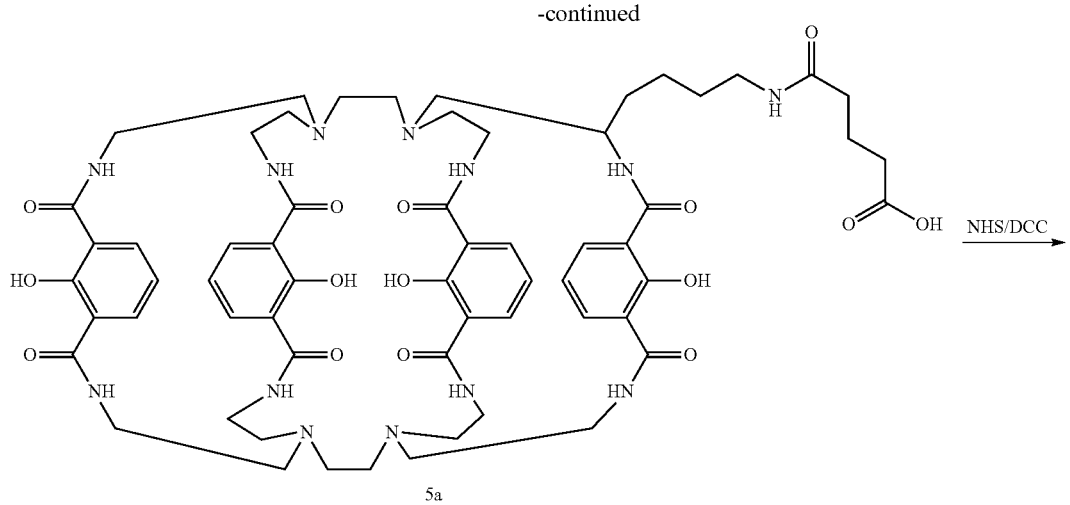

5a

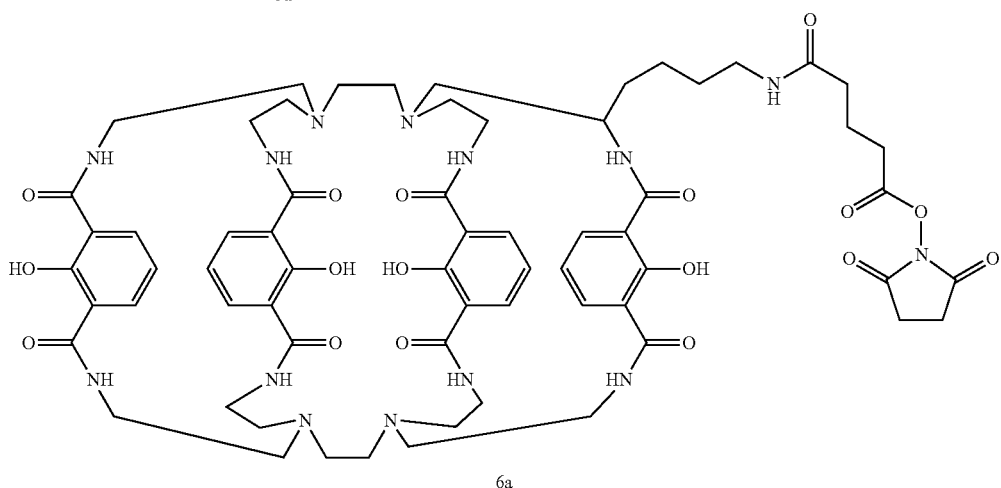

6a

Me₄EtGlutarBocLysBH(2,2)IAM (E-18)

Compound E-15 (0.25 g, 0.2 mmol), was taken up in a 1:1 mixture of dichloromethane and trifluoroacetic acid (10 mL); the solution was allowed to stir for 3 hr. After evaporation, the residue was dissolved in methanol, and the pH of the solution was adjusted to 11 with 0.1 N KOH in methanol solution. This basic solution was loaded onto a basic alumina plug and eluted with 10% methanol in dichloromethane to remove the TFA salt and excess base. After removing the solvent, the de-Boced macrocycle E-16 was used directly for next step reaction.

The raw compound E-18 was dissolved in dry DMAA (2 mL) and mixed with excess (2 equiv.) of ethyl glutarate NHS ester in dry dichloromethane solution (10 mL). The reaction mixture was stirred at room temperature for 4 h; the resulted macrocycle E-18 was purified by gradient flash silica chromatography (2-7% MeOH in $CH_2Cl_2$).

$^1$H NMR (500 MHz, DMSO-$d_6$, 25° C.): δ 1.14(t, 3H, $CH_3$), 1.20-1.60 (m, 6H, $CH_2$), 2.05 (m, 2H, $CH_2$), 2.26 (m, 2H, $CH_2$), 2.52-2.80 (m, br, 23H, NCH+ $NCH_2$), 3.21-3.62 (m, br, 16H, $NHCH_2$), 3.65-3.7 (m, 12H, $CH_3$), 4.03(m, 2H, $CH_2$), 5.73(s, 1H, amideH), 7.01-7.15 (m, 4H, ArH), 7.32(d, 1H, amideH), 7.50-7.65 (m, 8H, ArH), 7.75(m, 1H, amideH), 7.95(m, 1H, amideH),8.10-8.20 (m, 4H, amideH), 8.26(m, 1H, amideH). $^{13}$C NMR (500 MHz, CDCl$_3$): δ 13.7, 20.5, 22.6, 24.8, 28.5, 32.6, 32.9, 34.7, 37.3, 38.4, 45.5, 50.8, 52.8, 53.1, 59.8, 62.0, 62.3, 62.6, 124.0, 127.5, 133.5, 155.0, 155.1, 164.9, 165.4, 172.0, 172.7. MS [(+)-FAB, NBA]: $C_{67}H_{91}N_{13}O_{15}$: m/Z 1318.8 [MH$^+$].

GlutarLysBH(2,2)IAM (5a)

Compound 18 (0.4 g, 0.3 mmol) was deprotected with BBr$_3$ as described for compound 4, the deprotected compound 5a was collected by centrifugation and vacuum dried at 40° C. to yield a beige solid was as product. Yield: 150 mg (53%).

$^1$H NMR (500 MHz, D$_2$O—NaOD, 25° C.): δ 0.78-2.25 (m, 10H, CH$_2$), 2.40-2.92 (m, 26H, NCH$_2$), 3.00-3.85 (m, 17H, NHCH$_2$), 6.08-6.52 (m, 4H, ArH), 7.35-7.90 (m, 8H, ArH). Anal. Calcd. (Found) for $C_{61}H_{79}N_{13}O_{15}$.3HBr.5.5H$_2$O (1576, 184): C, 46.48 (46.44); H, 5.96 (5.98); N, 11.55 (11.39). MS [(+)-FAB, TG/G]] $C_{61}H_{79}N_{13}O_{15}$: m/Z 1234.5 [MH$^+$].

GlutarLysBH(2,2)IAM-NHS ester (6a)

To a solution of GlutarLysBH(2,2)IAM (16 mg, 0.01 mmol) in dry DMF (2 mL), excess of NHS (3 equiv.) and a catalytic amount of DMAP (2 mg) was added. The solution was stirred for 30 min, and DCC (2 equiv.) was added. After the reaction mixture was stirred for 4 h, another equivalent amount of DCC was added, the solution was stirred overnight under nitrogen. The mixture was divided into a 1:1 mixture of cyclohexane and 2-propanol (5 mL) and stirred for 30 min. then centrifuged to separate the precipitate from the mother liquor. The precipitate was suspended in 5 mL 2-propanol with vigorous stirring to wash away any low molecular weight impurities and then centrifuged. Such washing-centrifuging process was repeated 3 times and the precipitate was dried under vacuum. FAB(+) Mass spectrum showed the MH+ ion (1331) without showing the un-activated molecular ion peak (1234). No effort has been made to further characterize this compound yet. New evaluation methods for these activated compounds are being developed.

Method of Making the Linker

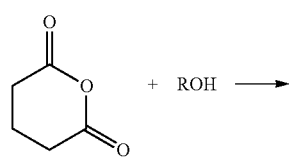 + ROH ⟶

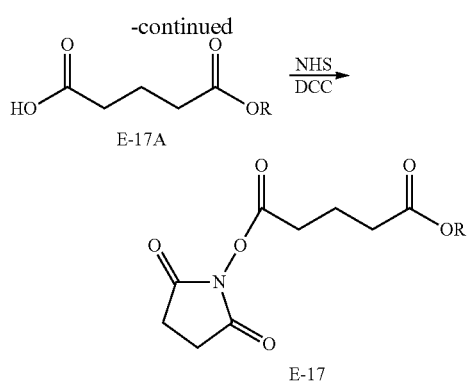

Example 7

Functionalizing the Macrocyclic Ligand (5)

Compound 5 was synthesized by coupling compound 4 with diglycolic anhydride according to Scheme 23 below.

Scheme 23

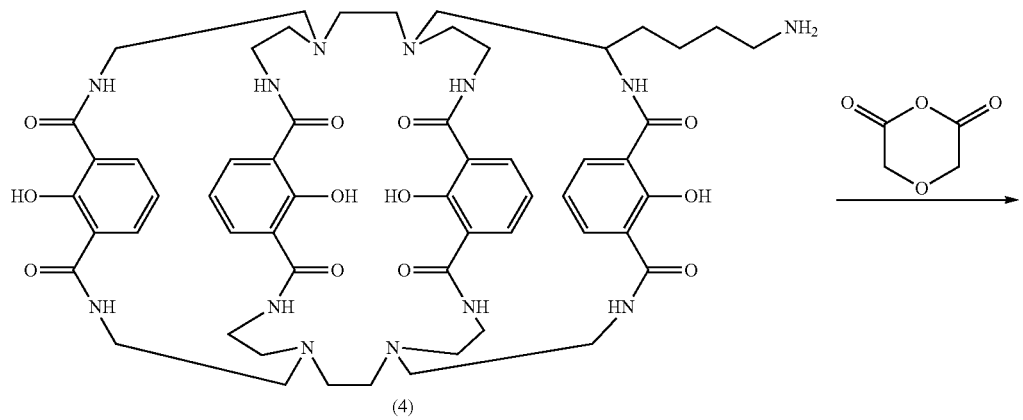

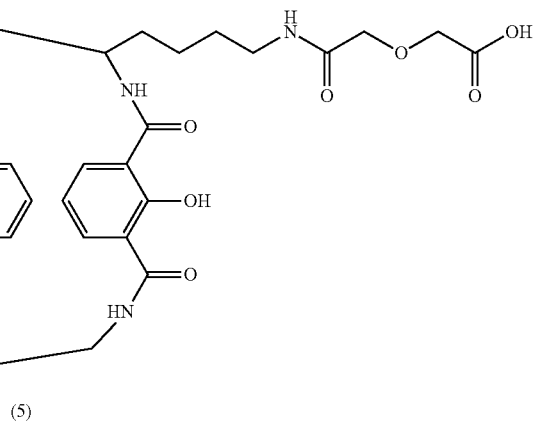

Example 8

Non-specific Interaction with Protein (Streptavidin)

It was previously observed that certain ligands such as 2 exhibit non-specific interactions with proteins, and the addition of a small amount of non-ionic detergent such as Tween-20 seemed to stabilize the luminescence of Tb-2 for short periods relative to solutions containing no Tween-20. However, the presence of detergents is undesirable in many applications.

It was therefore important to determine the tendency of the novel ligands to non-specifically interact with proteins. Sulfo-NHS ester and NHS ester derivatives of compound 5 were synthesized and conjugated to streptavidin. For comparison, the NHS ester of ligand 2 was also conjugated to streptavidin. Streptavidin was equilibrated in carbonate buffer, pH 9, at a concentration of approximately 130 µM. A DMF solution of the activated esters of each ligand was added to the protein at a final concentration of approximately 1 mM. The mixtures were allowed to incubate at 4° C. for 1 h. The metal is added either before or after conjugation of the ligand to the protein. Non-conjugated ligand was separated from conjugated protein using a G50 gel filtration centrifugal spin column technique (Penefsky, H. S, *Methods Enzymol* 1979, 56:527-30). This technique dilutes protein solutions to a lesser extent than conventional gel filtration techniques. Consecutive spin columns were run on a single protein sample solution to evaluate the extent of non-specific absorption of ligand. Following a single gel filtration separation, most of the excess ligand is removed and left at the top of the gel bed. A second spin column treatment should leave no further ligand at the top of the second column unless non-covalent association of the ligand with the protein occurs.

Results

A significant amount of ligand 2 was left at the top of the gel bed of the second and even third consecutive gel filtration spin columns as visualized by a high degree of residual luminescence. On the other hand, the residual luminescence for activated 4 (both sulfo-NHS and NHS) was close to background. Thus, the separation of unconjugated 4 from conjugated streptavidin was efficient and non-specific binding of those ligands to streptavidin was found to be minimal.

These experiments demonstrated that the characteristic non-specific association with proteins observed for the acyclic ligand 2 is largely reduced and almost eliminated with the macrocyclic ligand 4. These results may be explained by the greater susceptibility of the acyclic ligands to open, when compared to the macrocycle, which has fewer degrees of freedom. The more constrained nature of the macrocycle may render the hydrophobic moieties less accessible and limit non-specific interactions of those groups with proteins.

The macrocyclic ligand 4 was conjugated to a variety of proteins other than streptavidin including protein A and several antibodies; the amount of non-covalent association of the ligand with these proteins was found to be insignificant compared to the levels observed for ligand 2.

Example 9

Stability of Terbium (Tb) Complexes
Stability of Tb Complexes in the Presence of Acid or EDTA To evaluate the stability of the macrocyclic complexes, the complexes were exposed to fairly harsh conditions such as 1% acetic acid and 5 mM EDTA solutions. 10% acetic acid is often used in the fixing and staining of gels, while EDTA is a commonly used preservative often used at a concentration of 1 mM.

Results

Studies revealed that Tb-3 complexes (at µM concentrations) exhibit strong Tb emission in 1% AcOH lasting longer than 1 h, whereas Tb-1 complexes lose their characteristic luminescence immediately upon dilution with 1% AcOH. Similarly, the luminescence of Tb-3 at µM concentrations is stable for greater than 1 h in 5 mM EDTA, while Tb-1 luminescence dissipates in less than 5 min. The reluctance of ligand 3 to release the $Tb^{3+}$ ion in the presence of a large excess of EDTA indicates a much higher kinetic stability at neutral pH (in addition to fairly acidic conditions) as compared to ligand 1. High complex stability is crucial when developing applications requiring the use of isophthalamide complexes at relatively dilute concentrations in complex aqueous solutions ($<1\times10^{-8}$ M) where the complex is exposed to a variety of molecules and materials. Without high stability at high dilution, reproducibility is poor and confidence in quantitative results decreases.

Comparison of Kinetic Stability for Different Tb Complexes in Various Media

In order to investigate the stability of macrocyclic ligands further, the stabilities of different Tb-complexes were determined using a variety of different media, including 1% acetic acid and 1 mM EDTA. Stock solutions of Tb complexes of compounds 1, 3 and 5a (1 uM) were prepared in TBST, 50 mM Tris, 150 mM NaCl, 0.05% Tween-80, pH 7.6. Each stock solution was then diluted 200× into different test solutions in polypropylene microcentrifuge tubes to a final concentration of 5 nM Tb-complex. Each test solution also contained 0.05% Tween-80. The test solutions were allowed to incubate at room temperature. Samples were taken at indicated time points, evaluated in triplicate and luminescence was recorded using standard time-resolved luminescence settings and 340 nm and 490 excitation and emission filters, respectively. Results are summarized in FIG. 1 (compound 1), FIG. 2 (compound 3) and FIG. 3 (compound 5a). The results demonstrate a significant increase in stability for terbium complexes derived from macrocyclic ligands (3 and 5a) when compared to a comparable, "non-restrained" ligand (1). The results further demonstrate that substitution of the macrocyclic ligand (3) can further increase the stability in certain media.

Stability of Tb Complexes during SDS-PAGE

The protein conjugated ligands described in Example 3 were evaluated by SDS-PAGE. All samples were boiled at 95° C. for 5 min after being mixed 1:1 with 2× reducing or non-reducing SAB. Bufferless Phastsystem gels (GE Healthcare) were loaded according to the manufacturer's instructions.

Experimental Results

Visible $Tb^{3+}$ luminescence was observed for all labeled protein samples following sample heating to 95° C. and exposure to SDS. These results demonstrate that the Lanthanide complexes of the present invention are unexpectedly stable under the tested conditions. Time-resolved CCD-based imaging systems would be useful to further assess the signal-to-noise differences in the obtained images. The use of a cutoff filter that removes the excitation light would improve image quality further.

Example 10

Figure 4:
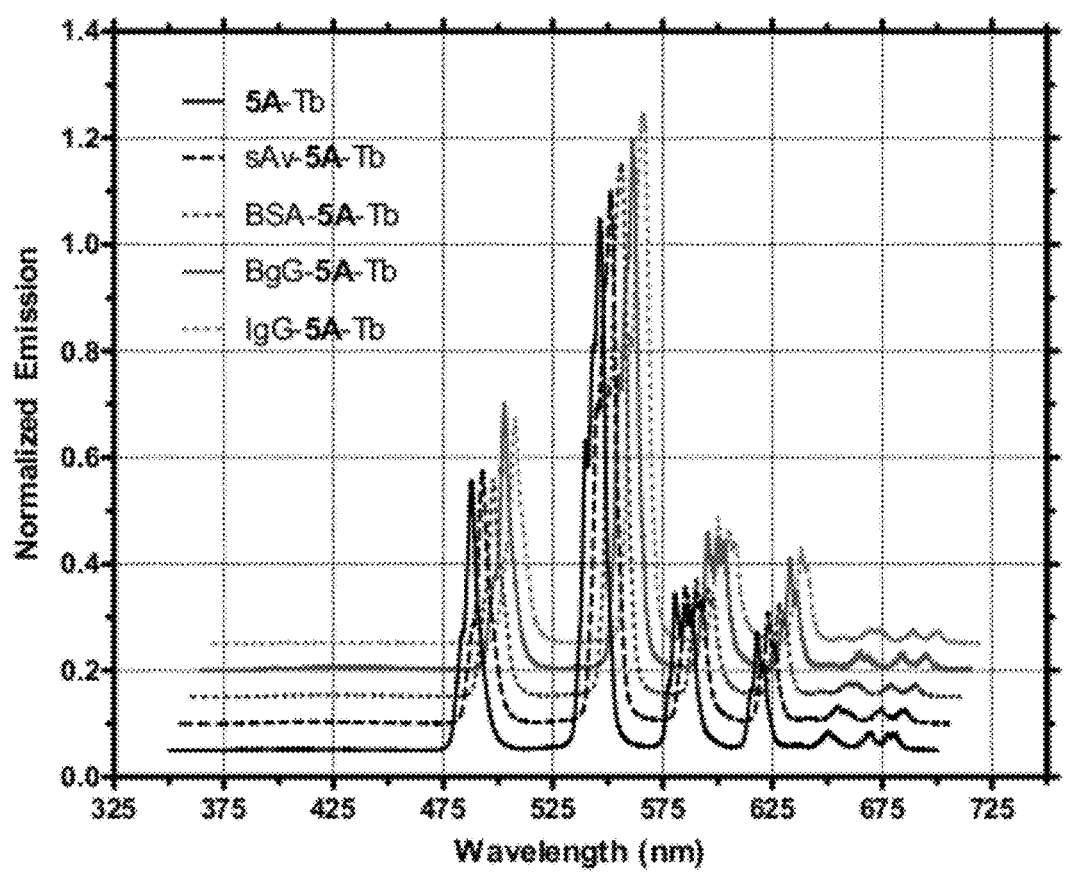
FIG. 4 is a chart indicating that the emission spectrum of unconjugated 5a-Tb is comparable to the emission spectra obtained for different protein conjugates of 5a-Tb.

Steady-state emission spectra were recorded to compare the emission of compound 5a-Tb when unconjugated and conjugated to various proteins. The emission spectrum of unconjugated 5a-Tb is comparable to the emission spectra obtained for different protein conjugates of 5a-Tb (FIG. 4).

Protein conjugates of 5a-Tb were prepared with streptavidin (sAv), bovine serum albumin (BSA), bovine gamma globulin (BgG), and immunoglobulin G (IgG). Briefly, the sulfo-NHS ester of 5a was prepared in situ by mixing 5a, EDC and sulfo-NHS in dry DMF and for one hour. The sulfo-NHS ester of 5a was then added dropwise to a stirring protein solution equilibrated in 100 mM carbonate, pH=9.0 and cooled to 4°. Reactions were allowed to proceed until an average of three to five 5a-Tb molecules were covalently bound per protein molecule. Luminescence measurements were recorded in Tris-buffered saline, pH 7.6. Excitation was carried out at 340 nm. Plots are displayed with a layered offset for clarity.

Figure 5:
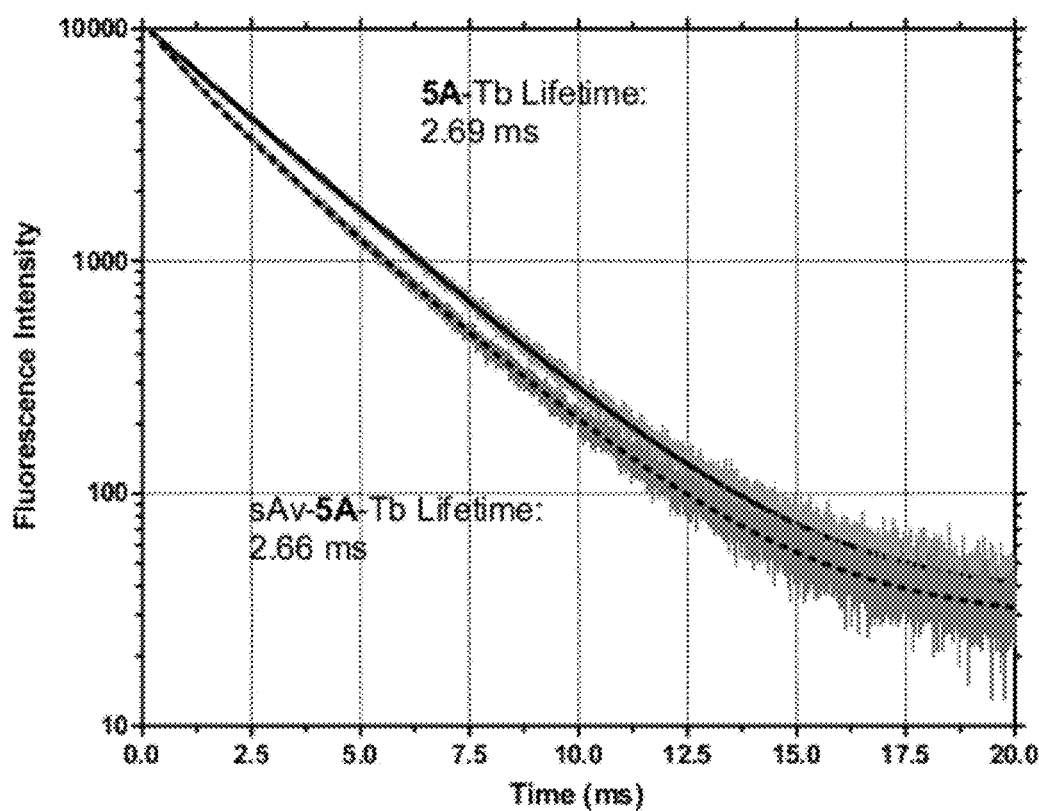
FIG. 5 is a chart comparing the luminescence decay lifetimes of unconjugated and streptavidin conjugated 5a-Tb.

Comparison of the luminescence decay lifetimes of unconjugated and streptavidin conjugated 5a-Tb show that the luminescence emission lifetimes are essentially the same (FIG. 5). Measurements were conducted on a Fluorolog-3 from Jovin Yvon incorporating a xenon flash lamp and decay lifetime detection hardware.

Figure 6:
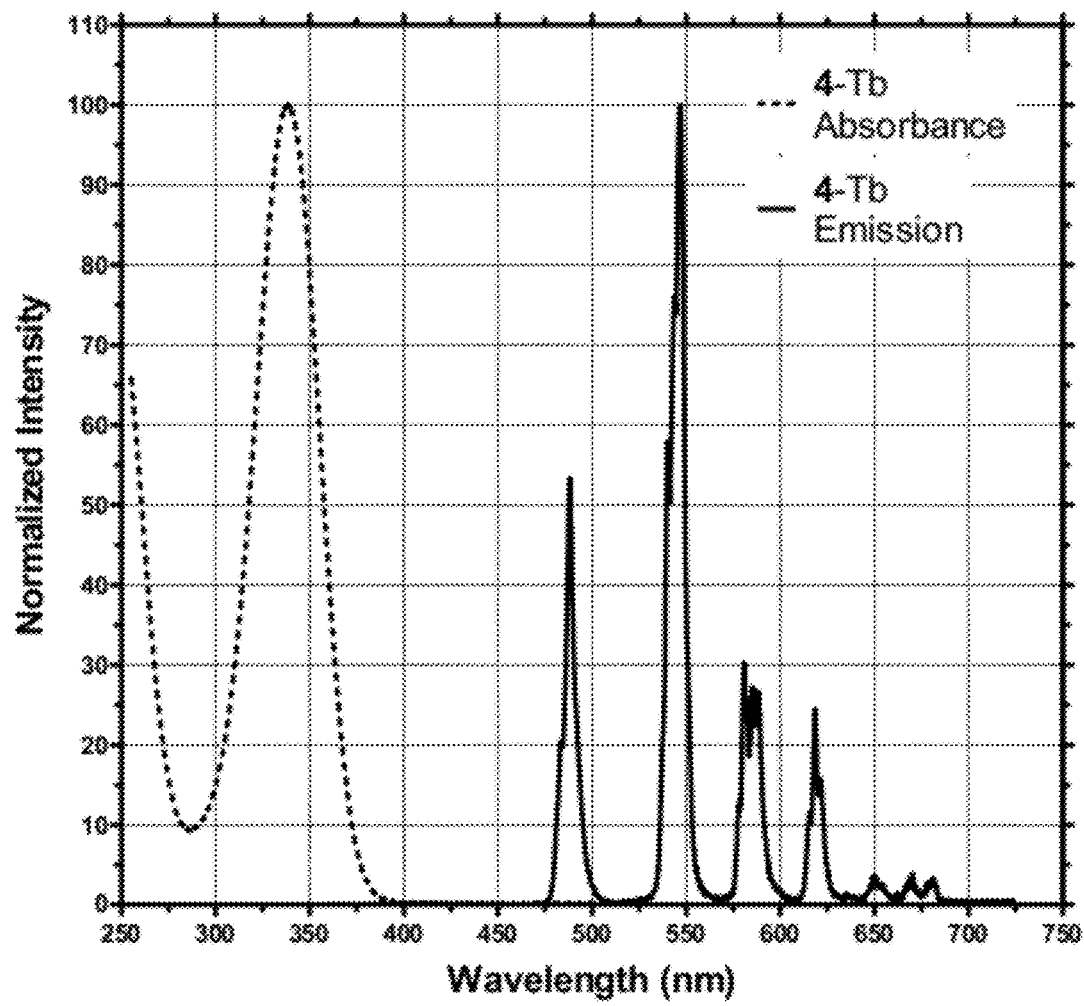
FIG. 6 is a chart indicating steady-state absorption and emission spectra which were recorded for compound 4-Tb.

Steady-state absorption and emission spectra were recorded for compound 4-Tb (FIG. 6). A broad absorption peak centered at 340 nm is characteristic of the sensitizing 2-hydroxyisophthalamide chelating units. The emission spectrum was recorded by exciting at 340 nm and is characteristic of luminescent terbium complexes with emission peaks centered at 488 nm, 545 nm, 585 nm and 618 nm.

It is understood that the examples and embodiments described herein are for illustrative purposes only and that various modifications or changes in light thereof will be suggested to persons skilled in the art and are to be included within the spirit and purview of this document and scope of the appended claims. All publications, patents, and patent applications cited herein are hereby incorporated by reference for all purposes.

What is claimed is:

1. A compound having a structure according to Formula III:

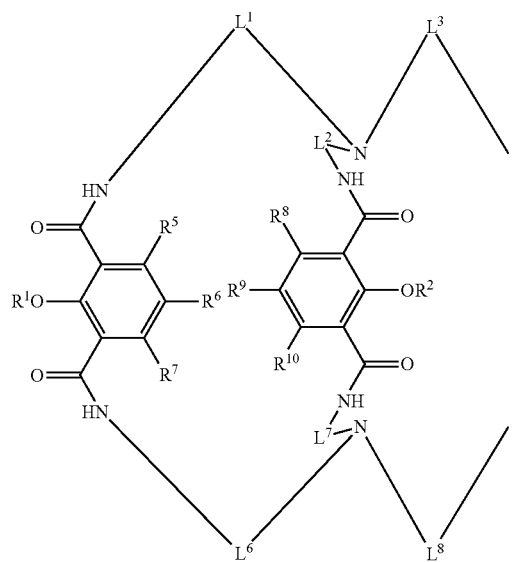

(III)

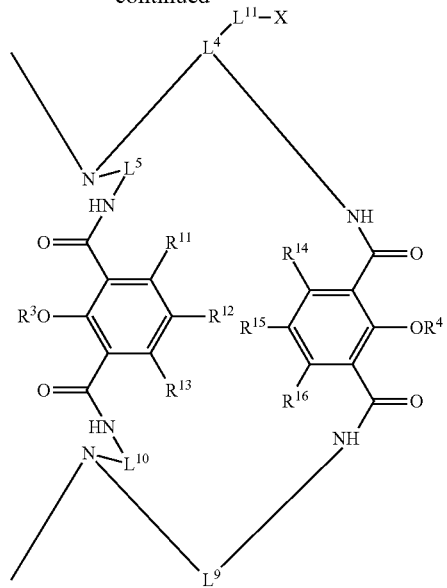

wherein
$L^1, L^2, L^3, L^4, L^5, L^6, L^7, L^8, L^9$ and $L^{10}$ are linker groups independently selected from substituted or unsubstituted ethyl;
$R^1$, $R^2$, $R^3$ and $R^4$ are members independently selected from H, an enzymatically labile group, a hydrolytically labile group, a metabolically labile group and a single negative charge;
$R^5, R^6, R^7, R^8, R^9, R^{10}, R^{11}, R^{12}, R^{13}, R^{14}, R^{15}$ and $R^{16}$ are H;
$L^{11}$ is a linker moiety selected from substituted or unsubstituted heteroalkyl and substituted or unsubstituted alkyl; and
X is a reactive functional group selected from an amine, a carboxylic acid, a maleimidyl, a thiazolidyl, a substituted or unsubstituted NHS ester, a sulfonated NHS ester, a succinimidyl, an isocyanate, and an isothiocyanate moiety.

2. The compound according to claim 1, wherein $L^{11}$-X is a member selected from

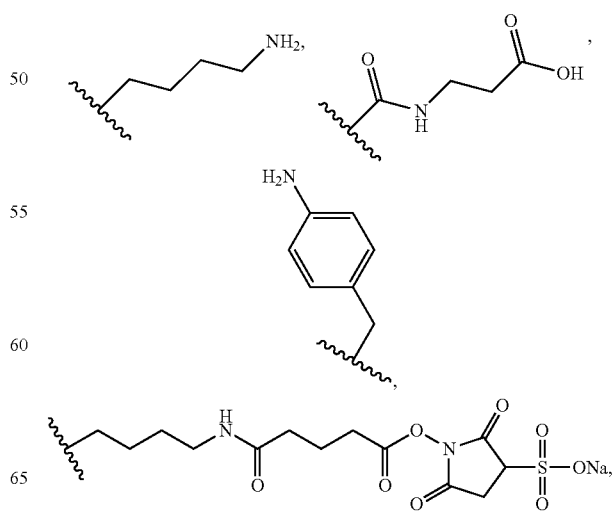

-continued
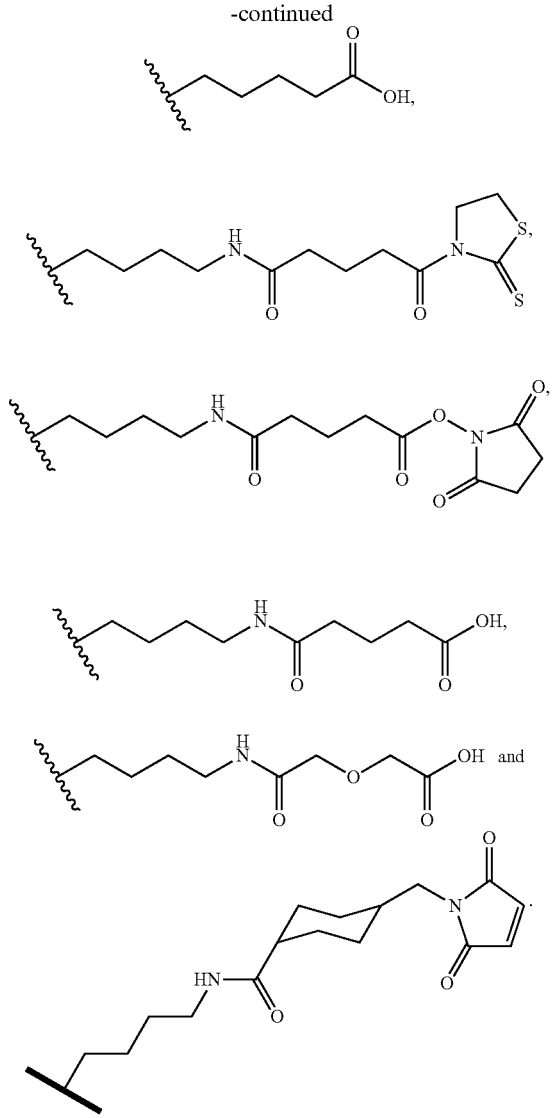
3. The compound according to claim 1, wherein $L^{11}$-X is a member selected from
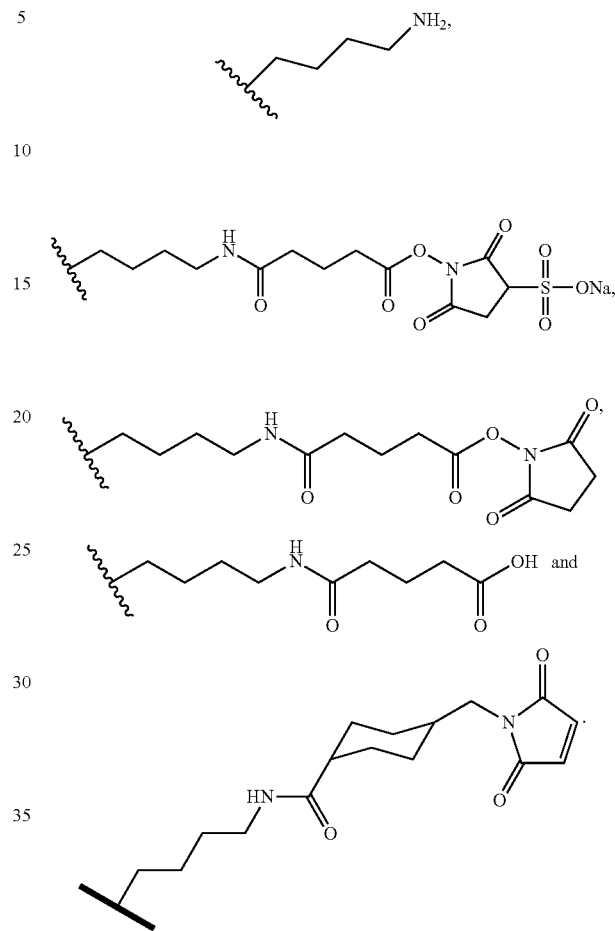
4. The compound according to claim 1, having a structure which is a member selected from:
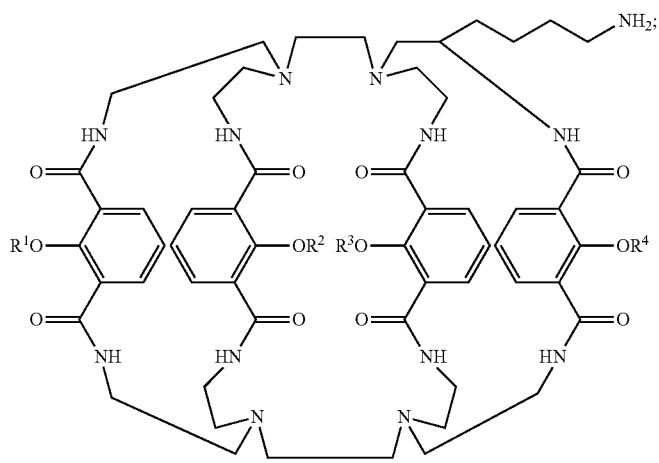

-continued
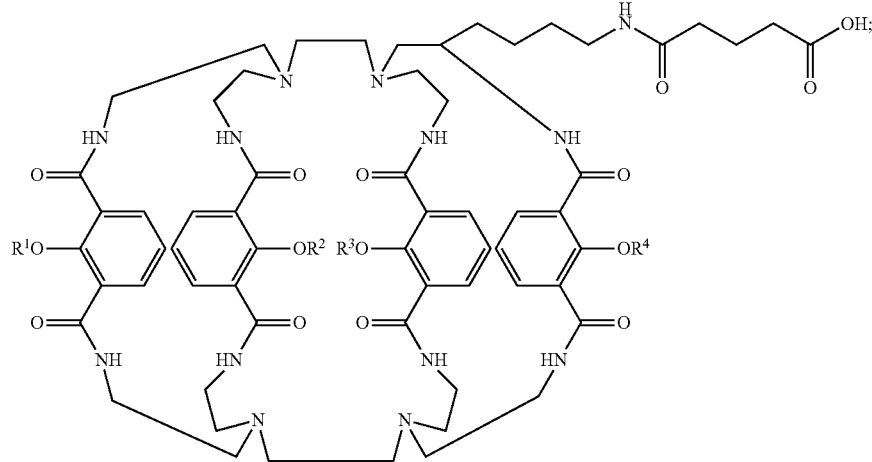
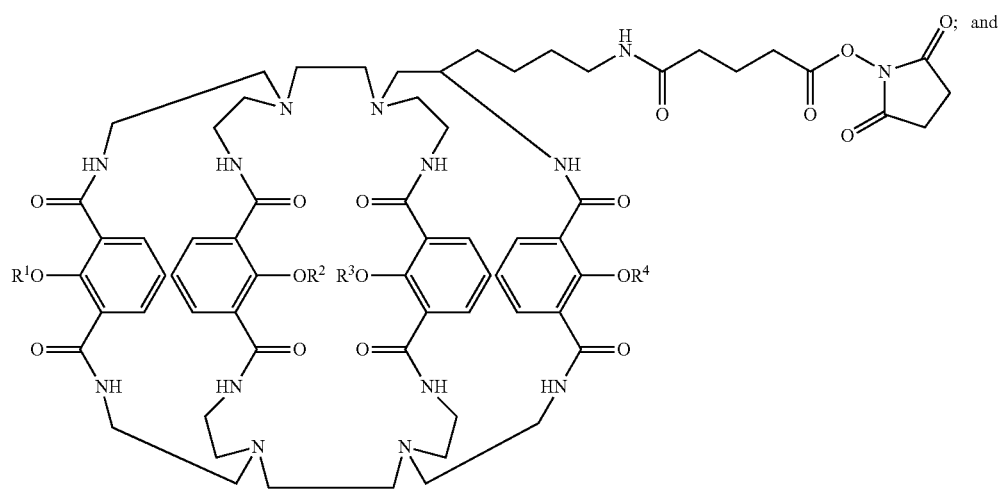
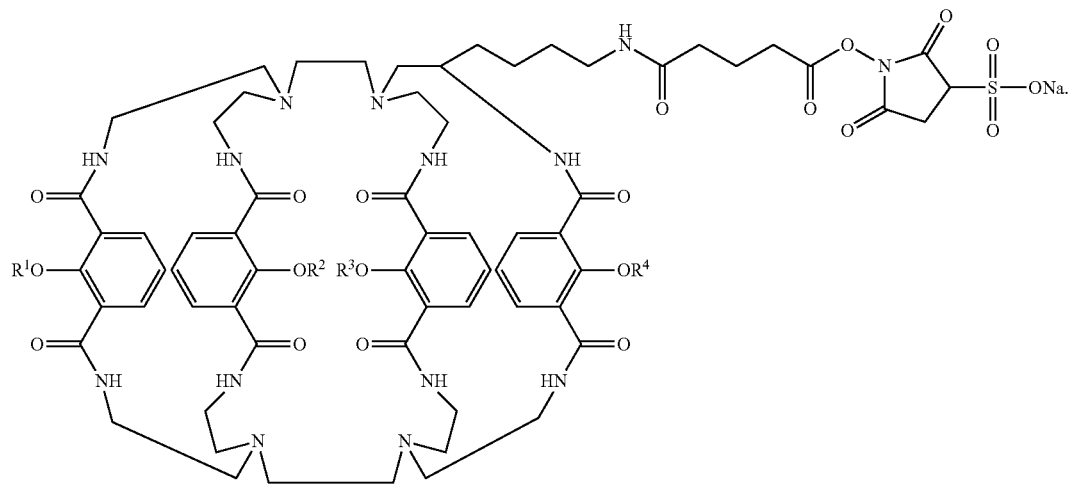

5. The compound according to claim 1, having a structure which is a member selected from:
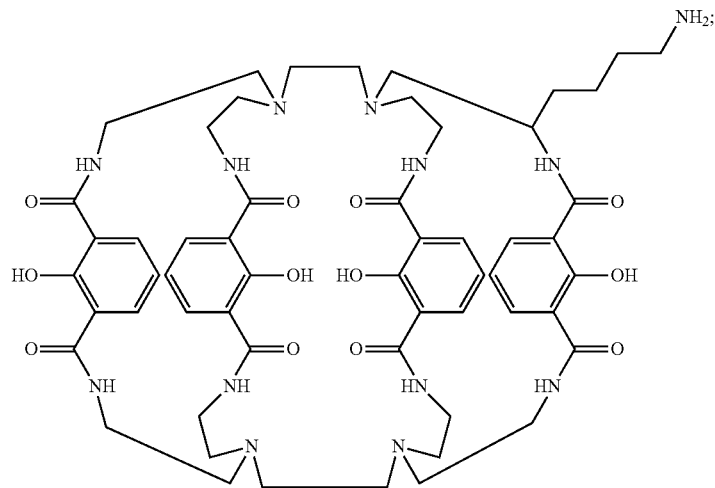
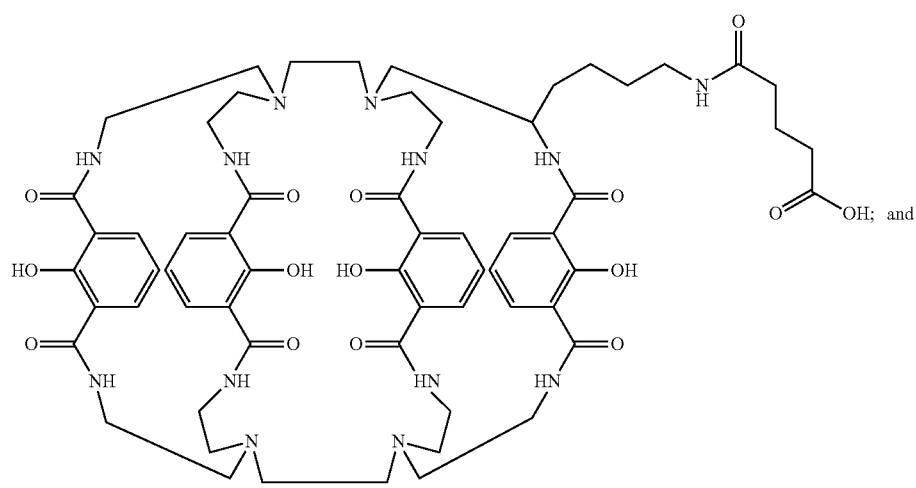
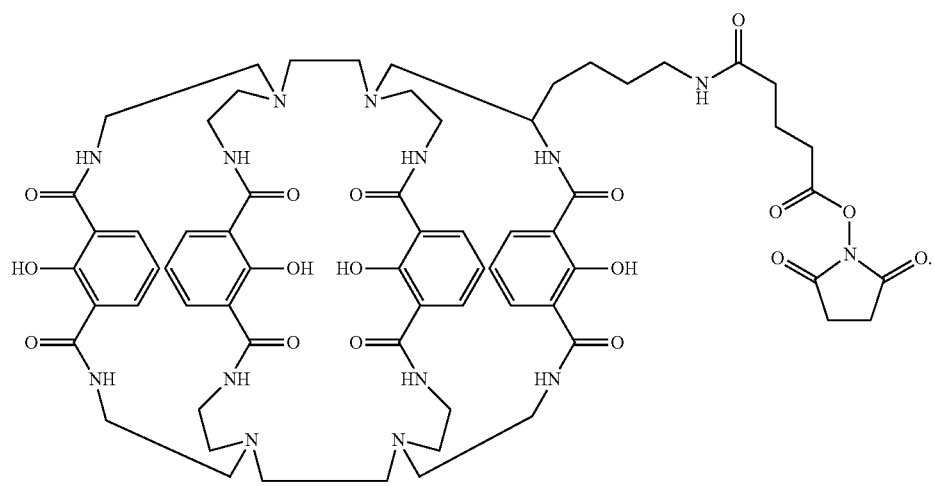

6. The compound according to claim 1, wherein $L^{11}$ comprises a polyether.

7. The compound according to claim 6, wherein said polyether is a member selected from polyethylene glycol (PEG) and derivatives thereof.

8. The compound according to claim 7, wherein said polyether has a molecular weight of about 50 to about 10,000 daltons.

9. The compound according to claim 8, wherein X is a maleimidyl or an unsubstituted NHS ester moiety.

10. The compound according to claim 1, wherein $L^{11}$ is substituted heteroalkyl or substituted alkyl; and X is an isothiocyanate moiety.

11. A luminescent complex formed between at least one metal ion and a compound according to claim 1.

12. The luminescent complex according to claim 11, wherein said metal ion is a lanthanide ion.

13. The luminescent complex according to claim 12, wherein said lanthanide is a member selected from neodymium (Nd), samarium (Sm), europium (Eu), terbium (Tb), dysprosium (Dy) and ytterbium (Yb).

14. A method of detecting the presence of an analyte in a sample, said method comprising:
　(a) contacting said sample and a composition comprising a luminescent complex according to claim 11,
　(b) exciting said complex; and
　(c) detecting luminescence from said complex.

15. A method of detecting the presence of an analyte in a sample, said method comprising:
　(a) contacting said sample and a composition comprising a luminescent complex according to claim 11 and a luminescence modifying group, wherein energy can be transferred between said luminescent complex and said luminescence modifying group when said complex is excited, and wherein said complex and said luminescence modifying group can be part of the same molecule or be part of different molecules;
　(b) exciting said complex; and
　(c) determining the luminescent property of said sample, wherein the presence of said analyte results in a change in said luminescent property.

16. The method according to claim 15, wherein said analyte, if present in said sample, binds to an antibody, wherein said antibody is covalently linked to a member selected from a luminescence modifying group and a luminescent complex according to claim 11.

17. The method according to claim 16, wherein said analyte is a lipid.

* * * * *